United States Patent
Ogden et al.

(10) Patent No.: US 12,037,706 B2
(45) Date of Patent: Jul. 16, 2024

(54) METHODS AND COMPOSITIONS FOR PROTEIN DETECTION

(71) Applicant: Manifold Biotechnologies, Inc., Allston, MA (US)

(72) Inventors: Pierce Ogden, Jamaica Plain, MA (US); Gleb Kuznetsov, Boston, MA (US); Shane Lofgren, Boston, MA (US); Kathleen Nudel, Jamaica Plain, MA (US); Hoong Chuin Lim, Newton Center, MA (US); Karen Duffy, Somerville, MA (US); Jeffrey Chang, Somerville, MA (US)

(73) Assignee: Manifold Biotechnologies, Inc., Boston, MA (US)

( * ) Notice: Subject to any disclaimer, the term of this patent is extended or adjusted under 35 U.S.C. 154(b) by 0 days.

(21) Appl. No.: 17/718,275

(22) Filed: Apr. 11, 2022

(65) Prior Publication Data
US 2023/0134754 A1    May 4, 2023

Related U.S. Application Data

(63) Continuation of application No. 17/518,221, filed on Nov. 3, 2021.

(51) Int. Cl.
| | | |
|---|---|---|
| C40B 40/08 | (2006.01) | |
| C07K 16/00 | (2006.01) | |
| C07K 16/18 | (2006.01) | |
| C07K 17/02 | (2006.01) | |
| C12N 15/10 | (2006.01) | |

(52) U.S. Cl.
CPC ............ C40B 40/08 (2013.01); C07K 16/005 (2013.01); C07K 16/18 (2013.01); C07K 17/02 (2013.01); C12N 15/1037 (2013.01); C07K 2317/55 (2013.01)

(58) Field of Classification Search
None
See application file for complete search history.

(56) References Cited

U.S. PATENT DOCUMENTS

2017/0260534 A1    9/2017  Koseki

FOREIGN PATENT DOCUMENTS

| WO | WO-2008/156789 A2 | 12/2008 |
|---|---|---|
| WO | WO-2013/143026 A1 | 10/2013 |
| WO | WO-2015/095355 A2 | 6/2015 |
| WO | WO-2017/190138 A1 | 11/2017 |
| WO | WO-2020/097254 A1 | 5/2020 |

OTHER PUBLICATIONS

Egloff, P. et al., Engineered Peptide Barcodes for In-Depth Analyses of Binding Protein Ensembles, Nat. Methods, 16(5):421-428 (2019).
(Continued)

*Primary Examiner* — Christian C Boesen
(74) *Attorney, Agent, or Firm* — Choate, Hall & Stewart LLP; Brenda Herschbach Jarrell; Margo R. Monroe

(57) ABSTRACT

Methods and systems for quantification of an abundance of one or more payloads (e.g. proteins) in a mixture (e.g. a complex mixture (e.g. in vivo)) using barcodes (e.g. peptide barcodes), binders (e.g. polypeptide binders), and binding agents (e.g. phage) are provided herein.

7 Claims, 26 Drawing Sheets
Specification includes a Sequence Listing.

(56) References Cited

OTHER PUBLICATIONS

Elshal, M. F. and McCoy, J. P., Multiplex Bead Array Assays: Performance Evaluation and Comparison of Sensitivity to Elisa, Methods, 38(4):317-323 (2006).

Engvall, E. and Perlmann, P., Enzyme-linked immunosorbent assay, Elisa: 3. Quantitation of specific antibodies by enzyme-labeled anti-immunoglobulin in antigen-coated tubes, Journal of Immunology, 109(1):129-135 (1972).

Holliger, P. et al., "Diabodies": Small Bivalent and Bispecific Antibody Fragments, Proc. Natl. Acad. Sci. U.S.A., 90:6444-6448 (1993).

Mohan, D. et al., PhIP-Seq Characterization of Serum Antibodies Using Oligonucleotide Encoded Peptidomes, Nat. Protoc., 13(9):1958-1978 (2018).

Poljak, R. J., Production and Structure of Diabodies, Structure, 2:1121-1123 (1994).

Pollock, S. B. et al., Highly multiplexed and quantitative cell-surface protein profiling using genetically barcoded antibodies, Proc. Natl. Acad. Sci. U.S.A., 115(11):2836-2841 (2018).

Shendure, J. et al., Accurate multiplex polony sequencing of an evolved bacterial genome, Science, 309(5741):1728-1732 (2005).

Towbin, H. et al., Electrophoretic transfer of proteins from polyacrylamide gels to nitrocellulose sheets: procedure and some applications, Proc. Natl. Sci. U.S.A., 76(9):4350-4354 (1979).

Trads, J. B. et al., Site-Selective Conjugation of Native Proteins with DNA, Acc. Chem. Res., 50(6):1367-1374 (2017).

Xu, G. J. et al., Comprehensive serological profiling of human populations using a synthetic human virome, Science, 348(6239):11 pages (2015).

International Search Report for PCT/US2022/079134, 8 pages, mailing date Apr. 19, 2023.

Written Opinion for PCT/US2022/079134, 8 pages, mailing date Apr. 19, 2023.

Matsuzaki, Y. et al., Peptide barcoding for one-pot evaluation of sequence-function relationships of nanobodies, Sci Rep., 11(1):21516 (2021).

No Author Listed, Could protein barcodes speed up drug development?, Manifold Bio scores $5.4M to find out, Fierce Biotech, Retrieved from the Internet: https://www.fiercebiotech.com/biotech/could-protein-barcodes-speed-up-drug-development-manifold-bio-scores-5-4-million-to-find, retrieved on Feb. 8, 2023.

No Author Listed, Manifold Bio's molecular 'barcodes' could breakthrough pharma's in vivobottleneck, retrieved from the Internet: https://techcrunch.com/2022/07/14/manifold-bios-molecular-barcodes-could-break-through-pharmas-in-vivo-bottleneck/, retrieved on Feb. 8, 2023.

Wroblewska, A. et al., Protein Barcodes Enable High-Dimensional Single-Cell CRISPR Screens, Cell, 175(4):1141-1155 (2018).

METHODS AND COMPOSITIONS FOR PROTEIN DETECTION

CROSS REFERENCE TO RELATED APPLICATIONS

The present application is a continuation of U.S. application Ser. No. 17/518,221, filed Nov. 3, 2021, the entire contents of which are hereby incorporated by reference in its entirety.

BACKGROUND

Assessments of binding agents (e.g., phages, polypeptide binders, antibodies, etc.) are central to much of molecular and pharmaceutical biology.

SEQUENCE LISTING

The present specification makes reference to a Sequence Listing submitted electronically (as a .txt file named 2013703-0002_Sequence_Listing.txt) on Apr. 13, 2022. The .txt file was generated on Dec. 14, 2021, and is 5,592,163 bytes in size. The entire contents of the Sequence Listing are herein incorporated by reference.

SUMMARY

The present disclosure provides insights and technologies that achieve improved or otherwise desirable assessment of agents (e.g., binding agents, therapeutic agents, and/or in some embodiments polypeptide agents such as antibody agents).

Among other things, the present disclosure appreciates that many current technologies for assessing, and in particular for determining presence and/or abundance of, one or more agents of interest, typically rely on mass spectroscopy and/or affinity (e.g., immuno-) detection. The present disclosure appreciates that many available affinity detection technologies are slow and/or costly to perform or implement; many such technologies must be performed one at a time and many are constrained, for example, by availability of fluorogenic substrates (e.g., that may be assessed by relevant technologies—e.g., light microscopy).

The present disclosure further appreciates that certain other technologies, such as DNA barcoding technologies, that are sometimes utilized to assess agents of interest, can also suffer disadvantages. DNA barcodes, for example, can lack stability and/or display undesirable immunogenicity, e.g., when utilized in vivo. The present disclosure appreciates that such technologies therefore can encounter problems, particularly for assessing agents (e.g., protein agents) in complex environments (e.g., in vivo)

Among other things, the present disclosure encompasses the recognition of the source of certain problems with available technologies typically utilized to assess agents of interest, and in particular to assess protein agents and/or binding agents (i.e., agents which participate in one or more binding interactions of interest). In particular, the present disclosure identifies the source of certain problems encountered by such technologies for assessment (e.g., detection and/or measurement of quantity, such as concentration) of multiple agents, and in particular when such agents are present in a complex system (e.g., in a complex solution and/or in vivo).

Furthermore, the present disclosure provides certain technologies that achieve such assessments, in some embodiments with surprisingly high accuracy. Those skilled in the art will appreciate that a number of contexts exist in which detection and/or measurement (e.g., of a precise amount), of a plurality of agents within a complex system is desirable; moreover, those skilled in the art will appreciate the benefit of high accuracy in many such contexts.

Among other things, the present disclosure provides technologies that achieve detection and/or measurement (e.g., highly accurate and/or otherwise precise measurement) of one or more, and in some embodiments of a plurality, of agents (e.g., protein agents), including in complex systems (e.g., in vivo). In some embodiments, detected agent(s) may be or comprise proteins (i.e., polypeptides) and/or forms thereof (e.g., aggregated; complexed; covalently modified such as by disulfide bond formation, glycosylation, pegylation, phosphorylation; truncated such as by proteolytic cleavage, etc.).

In some embodiments, provided technologies are particularly useful or effective for assessment of therapeutic agents. For example, in some embodiments, provided technologies may be particularly useful for the assessment of one or more features (e.g. properties (e.g., concentration, localization, persistence, affinity, etc)) of agent(s) of interest; in some such embodiments, relevant agent(s) may be characterized by one or more attributes appropriate or desirable for therapeutic use. For example, in some embodiments, provided technologies may be used to screen potential therapeutic agents (e.g. polypeptide entities) for one or more features (e.g. properties, attributes) suitable for therapeutic use. In some embodiments, each feature of potential therapeutic agent(s) may be measured one at a time. In some embodiments, two or more features of potential therapeutic agent(s) may be measured simultaneously. For example, in some embodiments, one or more therapeutic agents may be screened for an affinity to a target protein—yet other desirable properties for example molecular stability in a physiologically relevant environment are not yet known. In some embodiments, for example, one or more therapeutic agents may be screened for an affinity to a target protein, along with other desirable properties, for example molecular stability in a physiologically relevant environment.

The present disclosure appreciates that many current methods of protein measurement rely on determining the abundance of light of a certain wavelength, or overall luminescence, such as western blot or ELISA (Towbin 1979, Engvall 1972). Due to constraints of visible light wavelength, these methods allow for only a small number of different proteins, often fewer than 4, to be measured at a single time within a single reaction (Elshal, 2006). The present disclosure appreciates that many applications, including drug discovery applications, would benefit from (and, in some cases, require) dramatically higher throughput.

The present disclosure further appreciates that nucleic acid sequencing technologies (e.g., DNA sequencing technologies) have been developed that can analyze billions of individual DNA molecules in a single experiment (Shendure, 2005). Various strategies have been developed to try to apply this massive throughput achievable with nucleic acid sequencing techniques to protein detection and measurement, in particular by tagging proteins with an attached piece of DNA (typically referred to as a "DNA barcode"), which may then be sequenced to indirectly detect the protein (Trads 2017) or one or more features of the protein.

The present disclosure appreciates the power of applying high-throughput nucleic acid sequencing technologies to assessment of other agents, and in particular of protein agents, but also identifies the source of certain problems associated with many approaches utilized to study proteins by attachment of DNA barcodes. For example, the present disclosure appreciates that modification of a protein by attachment of a DNA barcode can often alter its functionality (Trads 2017), which can defeat the purpose of using the DNA barcode to assess the protein.

Known techniques to quantify barcoded proteins include those as presented in Egloff et al. (2019), that use mass spectrometry to determine the presence or absence of a protein sequence in a mixture (Egloff 2019). The present disclosure identifies the source of a problem with such approaches, however, and moreover provides certain advantages relative to them, including, for example, by using nucleic acids (e.g. DNA) for amplification of the original signal; approaches such as those described in Egloff et al. fail to include (or to benefit from) such a feature. Furthermore, as may be appreciated by a person of ordinary skill in the art, reading the present disclosure, mass spectrometry only reads out the mass-to-charge ratio of an associated sequence; thus methods using mass spectrometry are limited in their total throughput, since different sequences can have the same mass-to-charge ratio. By comparison, the present invention is not limited by such disadvantages since the nucleic acid sequence associated with one or more binding agents in turn associated with each barcode is sequenced and measured to determine and quantify the barcoded protein.

Other techniques available in the art use antibodies displayed on phage (Fab-phage) to determine presence of endogenous proteins expressed on cell surfaces (Pollock 2018). In such methods, one Fab-phage is generated per endogenous protein (i.e. target protein to be assessed) and no barcodes are utilized. In contrast, the present technology envisions the use of engineered barcode sequences that are generalizable, such that they can be used to mark any protein, whether endogenous or exogenous to the context in which it is applied, and subsequently measured using one or more binding agents to which each barcode, and therefore each barcoded protein, is uniquely associated with (i.e. 'barcode fingerprint' as described elsewhere in this disclosure). Such complex association of one or more binding agents with a barcode is then measured and precise quantification of the associated protein is achieved, e.g., using a complex algorithm (i.e. 'decoding' as described elsewhere in this disclosure).

The present disclosure recognizes the ability of antigens displayed on phages to determine epitopes of antibodies within the blood to which the phages are able to bind (Mohan 2018). However, this method is not able to determine the sequence of the antibody to which the antigen binds, and thus only provides limited information on any antibodies that specifically bind to the antigens displayed on phage. However, the present disclosure provides systems, compositions, and methods that provide the advantage of using generic barcodes with known affinities to one or more binders or binding agents, that can be used to tag any target(s) of interest in a complex mixture, including but not limited to blood, to determine and quantify the target(s).

The present disclosure, among other things, provides technologies that can achieve assessment (e.g. detection and/or quantification) of multiple agents (e.g., multiple protein agents) within a pool of such agents, using DNA sequencing without requiring (direct or indirect) covalent association of the DNA with the assessed agent, or otherwise constraining the assessed agent.

Described herein are peptide barcodes (also known as "barcodes") and technologies to make and/or utilize them. In some embodiments, barcodes are utilized to mark payloads. Among other things, such an approach can achieve pooled measurement of protein payloads without amending non-protein identifiers. In some embodiments, a peptide barcode is an amino acid polypeptide sequence. In some embodiments, a peptide barcode is contained within a protein (e.g. a protein (e.g. an antibody) to be measured; i.e. is endogenous to a protein to be measured). In some embodiments, a peptide barcode is not contained with a protein (e.g. a protein (e.g. an antibody) to be measured; e.g. is exogenous to a protein to be measured). In some embodiments, a barcode, for example, is sequence (e.g. a designed sequence) contained within a protein (e.g. a protein to be measured). In some embodiments, a barcode is associated (e.g. bound (e.g. covalently)) to the N terminus of a protein (e.g. a protein to be measured). In some embodiments, a barcode is associated (e.g. bound (e.g. covalently)) to the C terminus of a protein (e.g. a protein to be measured). In some embodiments, a barcode is associated (e.g. bound (e.g. covalently)) proximal to the N terminus (e.g. internal to a protein (e.g. a loop region that is proximal to the N terminus)) of a protein (e.g. a protein to be measured). In some embodiments, a barcode is associated (e.g. bound (e.g. covalently)) proximal to the C terminus e.g. internal to a protein (e.g. a loop region that is proximal to the C terminus)) of a protein (e.g. a protein to be measured).

The methods disclosed herein may use peptide barcodes that are designed to have varying lengths. In some embodiments, a peptide barcode may have a length ranging between 1-100, 5-50, 8-25, 9-25, or 9-15 amino acids. In some embodiments, a peptide barcode may have a length of at least 25 amino acids. In some embodiments, a peptide barcode may have a length of at most 8 amino acids. In some embodiments, a peptide barcode may have a length of 10 amino acids.

Barcode sequences as described herein may be reused, so as to be able to quantify different payloads (e.g. proteins of interest) or mixture of payloads (mixture of proteins of interest to be measured). In some embodiments, a barcode is generated such that it can be easily reused between several different payload (e.g. proteins to be measured) molecules across different experiments.

Among other things, barcodes described herein are designed to be distinct/unique. In some embodiments, a barcode is designed to have a distinct sequence (e.g. distinct from another barcode). For example, each barcode is designed to be distinct (e.g. unique) from every other barcode used in an experiment, such that each payload (e.g. protein to be measured) is attached to at least one barcode, and each barcode (e.g. barcode with a specific sequence) is only attached to one payload. As may be understood by a person of ordinary skill in the art, the diversity of barcodes contained within a pool is limited only by the possible diversity of amino acid sequences for a given barcode length. For example, for a barcode length 'N', there exists $20^N$ distinct amino acid barcode sequences of length N.

Methods described herein relate to the detection of one or more barcodes using a binding agent. In some embodiments, a barcode is contacted with a binding agent that is associated with or comprises a detectable nucleic acid. For example, in some embodiments, a binding agent may be or comprises a phage, a ribosome, mRNA, DNA etc. In some embodiments, a binding agent is a phage with a binding motif on its surface (e.g. a polypeptide binder as described herein). In some embodiments, a binding agent comprises a detectable nucleic acid. In some embodiments, a binding agent expresses a detectable nucleic acid. In some embodiments, a binding agent expresses a detectable nucleic acid on (e.g. on a surface of) the binding agent (e.g. a binder). In some embodiments, a binder is polypeptide. In some embodiments, a binder associates with a barcode (e.g. with known specificity and affinity). In some embodiments a binder associates with one or more barcodes (e.g. with different known specificities and affinities). In some embodiments, a binder is an antibody (e.g. expressed on a surface of a binding agent). In some embodiments, for example, to detect the presence of a specific (e.g. distinct) barcode, the present disclosure envisions the association of a distinct detectable nucleic acid (e.g. a DNA sequence, an RNA sequence, etc.) to a specific barcode. This is achieved through the contact of a binder, which may be expressed on (e.g. on a surface of) a binding agent that comprises the distinct detectable nucleic acid.

Described herein are binders. In some embodiments, a binder, is a polypeptide. In some embodiments, for example, a binder is generated to have known specificity and affinity for a given barcode. In some embodiments, a binder is generated to have known specificity and affinity for one barcode. In some embodiments, a binder is generated to have known specificity and affinity for multiple (e.g. two or more, three or more, etc.) barcodes. In some embodiments, a binder is generated to have known specificity and affinity for at least one barcode. In some embodiments, a binder, for example, is expressed on the surface of a binding agent (e.g. a phage, a ribosome, etc.) using methods known to those skilled in the art.

Among other things, systems and methods described, for example, as described herein, identify the advantages of nucleic acid sequencing techniques and apply them effectively to protein detection and measurement methods. For example, methods described herein may use several binders, with known specificities and affinities to different barcodes, which can be expressed on binding agents and mixed together in a single pool. Upon mixing with a pool of barcoded proteins (i.e. proteins, each associated with a barcode as described herein), a binder expressed on a binding agent binds to any given barcode in the pool with known but varying affinities. Such a spectrum of affinities of a binder to various barcodes is termed herein as a 'Binder Fingerprint'. Conversely, a barcode may bind to any given binder in a pool of binders with known but varying affinities. Such a spectrum of affinities of a barcode to various binders is termed herein as a 'Barcode Fingerprint'. Thus, the presence of specific barcoded proteins can be detected, for example, in a complex solution, by extracting and sequencing the associated nucleic acid (e.g. detectable nucleic acid (e.g. DNA sequence, RNA sequence, etc.)) of the population of binding agents (e.g. phage) that bound to the barcodes associated with the proteins.

Other methods to use binders to identify protein sequences have been developed. However, these methods encounter a number of challenges, including difficulty in generating and characterizing binders, and effectively decoding their binding to specifically identify proteins. Another limitation with previously developed binders is their non-specific binding that results in bad signal to noise ratios, thereby negatively affecting the accuracy of detection. In contrast, the present technology generates many binders rapidly (e.g., in about a week, about 2 weeks, about 3 weeks, about 4 weeks, about 1 month, about 2 months, about 3 months, about 4 months, about 5 months, about 6 months, or about 1 year). In some embodiments, for example, between about 100 to about 1000 binders may be generated rapidly. In some embodiments, between about 10 to about 1000 binders may be generated rapidly. In some embodiments, between about 10 to about 10,000 binders may be generated rapidly. In some embodiments, at least about 10.000 binders may be generated rapidly.

Binders as described herein are robust. Binders can bind to barcodes (e.g. with robust affinities to one or more barcodes) as described herein in a variety of conditions and/or environments. For example, binders as described herein can bind to barcodes (e.g. with robust affinities to one or more barcodes) in various complex environments (e.g. in blood, tissue, serum, plasma, etc.). Thus, binders of the present disclosure may be used to detect targets (e.g. proteins of interest) in varying conditions (e.g. physiological conditions).

Analogously, barcodes, as described herein, may be generated in a rapid and robust manner. In some embodiments, barcodes as described herein are specific to binders as described herein. In some embodiments, for example, between about 100 to about 2000 barcodes may be generated rapidly (e.g. in about a week, about 2 weeks, about 3 weeks, about 4 weeks, about 1 month, about 2 months, about 3 months, about 4 months, about 5 months, about 6 months, or about 1 year). In some embodiments, between about 10 to about 1000 barcodes may be generated rapidly. In some embodiments, between about 10 to about 10,000 barcodes may be generated rapidly. In some embodiments, at least about 10,000 barcodes may be generated rapidly.

Barcodes as described herein are robust. Barcodes can bind to binders (e.g. with robust affinities to one or more binders) as described herein in a variety of conditions and/or environments. For example, barcodes as described herein can bind to binders (e.g. with robust affinities to one or more binders) in various complex environments (e.g. in blood, tissue, serum, plasma, etc.). Thus, barcodes of the present disclosure may be used to detect targets (e.g. proteins of interest) in varying conditions (e.g. physiological conditions). The present disclosure, therefore corrects for the disadvantages and defects of existing methods (e.g. non-specific binding, variable binding in different environments, etc.) by generating large numbers of robust binders and barcodes rapidly, which may be used in combination with computational methods (e.g. deconvolution methods) described herein, to allow for specific, well-characterized binder-barcode binding/association and accurate detection methods.

The present disclosure also envisions the ability to modify the sequence(s) of one or more peptide barcode sequences such that they are optimally distinguishable from each other, and/or from potential background protein sequence. Analogously, present disclosure also envisions the ability to modify the sequence(s) of one or more polypeptide binder sequences such that they are optimally distinguishable from each other, and/or from potential background protein sequence.

Among other things, the present invention as described herein provides methods of testing 'n' distinct protein candidates where n≥1, in a single assay or animal model. In some embodiments, a protein candidate is a therapeutic protein candidate. In some embodiments, multiple protein candidates are designed and each distinct protein candidate is associated with its own unique peptide barcode as described herein. Such barcoding has many advantages, including but not limiting to injecting all protein candidates in a single injection in to an assay and/or an animal in a cost and time efficient manner. Subsequently, a sample (e.g. tissue sample, serum sample, blood sample, extracellular sample, single cell sample etc.) from an injected animal may be obtained and barcodes extracted. In some embodiments, such extracted barcodes provide a measure of the relative abundance of protein candidates originally injected. For example, one or more extracted barcodes may be identified by contacting them with a pool of binders (e.g. expressed on a binding agent) known to bind to the barcodes originally bound to the protein candidates. Following binding of barcodes and binders, bound binding agents (e.g. phage) are selected and their detectable nucleic acid (e.g. DNA sequence, RNA sequence, etc.) extracted. In some embodiments, extracted nucleic acids are subjected to sequencing (e.g. next generation sequencing). The sequenced nucleic acid may then be used to identify the one or more barcodes they were designed to bind to, which along with the previously established information on binding affinities between various binder-barcode pairs may be used to identify and determine the relative abundance of each protein originally injected.

Also described herein, are methods used to translate nucleic acid counts, for example from a sequencing experiment, to relative or absolute protein quantifications. In some embodiments, nucleic acid sequences are counted and in silico translated into protein sequences. As is described herein, a nucleic acid sequence corresponds to a binder sequence, with established and characterized affinity for every barcode given in a pool. In some embodiments, binder counts are compared to a database of known propensities for binding to a single barcode. In some embodiments, binder counts are compared to a database of known propensities for binding to multiple barcodes (e.g. two or more, three or more, etc.). In some embodiments, for example in a sequencing experiment, relative proportions of binder counts are compared directly in order to determine relative proportions of barcodes and/or proteins associated with barcodes. In some embodiments, as may be known to a person of ordinary skill in the art, sequences (e.g. control sequences or accessory sequences) of known abundance (e.g. count, quantification, concentration, etc.) are utilized (e.g. added in to the sequencing experiment) to determine an absolute abundance (e.g. count, quantification, concentration, etc.) for a given binder or binders, which may be used to estimate an absolute abundance (e.g. count, quantification, concentration, etc.) for a barcode or barcodes, and/or protein(s) associated with barcode(s) using either direct counts or a linear model as described herein.

In some embodiments, payloads is or comprise proteins. In some embodiments, payloads is or comprise therapeutic proteins. In some embodiments, payloads are associated (e.g. linked with) barcodes as described herein.

Among other things, the present disclosure provides a method of assessing barcodes, binders (e.g. binding agents (e.g. with binders expressed on a surface)), payloads, (e.g. barcoded payload (e.g. barcoded proteins)) as described herein. In some embodiments, a method comprises subjecting a population of barcoded payloads (e.g. barcoded proteins) to an assessment; separating those members of a population that satisfy an assessment from those that do not, so that either a positive population or a negative population, or both is identified; contacting a positive population, or a negative population, or each population separately from the other, with a set of binders which includes at least one particular binder specific for each barcode in a population; and determining which binders bind to separated members, thereby determining which barcoded payloads (e.g. barcoded proteins) are present in a contacted population(s).

The present disclosure provides a method comprising contacting a set of binders either with a first population, with a second population, or separately with each of a first and second populations, of barcoded payloads (e.g. barcoded proteins); and determining which binders of a set bind to a member of a first population, a second population, or both, thereby determining which barcoded payloads (e.g. barcoded proteins) are present in contacted population(s). In some embodiments, each binder binds specifically (e.g. with known affinities) to one or more barcodes. In some embodiments, a set of binders, collectively, includes at least one binder specific for each of the barcodes in first and second populations. In some embodiments, a first and second populations have been separated from one another based on performance in an assessment.

In some embodiments, a method further comprises determining differences between a first and second population, to determine a functional effect of a performance assessment. In some embodiments, a method comprises separating binders that bind to at least one payload (e.g. barcoded payload (e.g. barcoded protein)).

In some embodiments, a step of determining comprises quantifying a number of binders that bind to a barcoded payload (e.g. barcoded protein). In some embodiments, quantifying may be performed by decoding a nucleotide sequence of each binder that binds to a barcoded payload (e.g. barcoded protein). In some embodiments, quantifying a number of binders that bind to a payload (e.g. barcoded protein) provides measure of a payload (e.g. protein) in a population.

In some embodiments, a step of determining comprises amplifying nucleic acids of bound phage particles. In some embodiments, a step of determining comprises determining nucleotide sequences of amplified nucleic acids. In some embodiments, one or more of determined nucleotide sequences corresponds to a coding sequence of a binder. In some embodiments, a step of determining comprises detecting one or more payloads (e.g. proteins) from a population of barcoded payloads (e.g. barcoded proteins) using determined sequence(s) of a coding sequence of a binder. In some embodiments, a step of determining comprises identifying one or more barcoded payloads (e.g. barcoded proteins) as a therapeutic or a target to treat a disease, disorder, or condition.

In some embodiments, a step of determining comprises performing one or more of amplification, propagation, and sequencing (e.g. nucleic acid (e.g. DNA, RNA) amplification, propagation, and/or sequencing). In some embodiments, amplification may be performed using one or more of Polymerase Chain Reaction (PCR), Loop-mediated Isothermal Amplification (LAMP), Rolling Circle Amplification (RCA), or a similar known technique. In some embodiments, sequencing may be performed using one or more of Illumina, Next Generation Sequencing (NGS), nanopore sequencing, Pac Bio long read sequencing, or a similar known technique.

In some embodiments, a step of separating comprises purifying one or more barcoded payloads (e.g. barcoded proteins) from a sample. In some embodiments, barcoded payloads (e.g. barcoded proteins) are purified from a complex sample. In some embodiments, barcoded payloads (e.g. barcoded proteins) are purified from a complex mixture. In some embodiments, barcoded payloads (e.g. barcoded proteins) are purified using affinity purification methods (e.g. FLAG IP, protein G/A) or protein precipitation methods.

In some embodiments, a method further comprises injecting a population of barcoded payloads into an animal. In some embodiments, a method further comprises injecting a population of barcoded payloads (e.g. barcoded proteins)

into an animal. In some embodiments, each barcode is bound to a specific binder expressed on a phage. In some embodiments, a method further comprises obtaining a sample from an animal to subject to an assessment.

In some embodiments, a method as described herein comprises determining relative amounts of each binder present in a sample, thereby identifying a subset of an injected population of barcoded payloads (e.g. barcoded proteins) present in a sample. In some embodiments, a method as described herein comprises comparing relative amounts to a standard of known concentration to determine an absolute quantity of each binder present in a sample.

In some embodiments, a method as described herein comprises optionally, repeating steps one or more of method steps described herein using an identified subset of payloads (e.g. proteins).

In some embodiments, a method as described herein comprises identifying one or more payloads (e.g. proteins) as a therapeutic or a target to treat a disease, disorder, or condition.

In some embodiments, a method as described herein comprises removing any unassociated (e.g. unbound) binders. In some embodiments, removing may be performed by washing.

In some embodiments, barcoded payloads (e.g. barcoded proteins) are in a sample. In some embodiments, barcoded payloads (e.g. barcoded proteins) are in a complex sample. In some embodiments, barcoded payloads (e.g. barcoded proteins) are in a complex mixture. In some embodiments, barcoded payloads (e.g. barcoded proteins) are in a purified sample.

In some embodiments, a sample is or comprises one or more of serum, blood, tissue, or a tumor. In some embodiments, a sample is a control (e.g. positive control or negative control).

In some embodiments, a sample is a complex sample. In some embodiments, a complex sample is or comprises a tissue. In some embodiments, a complex sample is or comprises blood. In some embodiments, a complex sample is a complex mixture. In some embodiments, a complex sample is or comprises one or more of serum, blood, or tissue.

In some embodiments, a barcode is or comprises one or more amino acids. In some embodiments, a barcode is comprised in a Complementarity-Determining Regions (CDR) of a payload (e.g. a protein). In some embodiments, a barcode is synthetic. In some embodiments, a barcode is 1-100, 5-50, 8-25, 9-25, or 9-15 amino acids in length. In some embodiments, a barcode is 10 amino acids in length. In some embodiments, a barcode has relatively no effect on payload (e.g. a protein) function. In some embodiments, a barcode does not illicit an immune response. In some embodiments, barcodes are orthogonal to each other. In some embodiments, at least one barcode is linked with a polypeptide (e.g. a polypeptide binder, a payload) of interest.

In some embodiments, a barcode is attached to a payload (e.g. a protein). In some embodiments, a barcode is attached to an optimal position on a payload (e.g. a protein). In some embodiments, an optimal position is a N-terminus or a C-terminus.

In some embodiments, a binder is or comprises a binding moiety displayed on a phage. In some embodiments, each binder of a set of binders is expressed on a phage. In some embodiments, a binder is expressed on a surface of a phage particle.

In some embodiments, a phage is selected from a group consisting of M13, T4, T7, Lambda, and filamentous phage. In some embodiments, a phage is M13.

The present disclosure provides, among other things, a nucleic acid whose nucleotide sequence is or comprises a sequence encoding a peptide barcode. In some embodiments, a peptide barcode has a length within a range of 1 to 100, 5 to 50, 8 to 25, 9 to 25, or 9 to 15 amino acids. In some embodiments, a peptide barcode has a length of 8 to 25 amino acids. In some embodiments, a peptide barcode has a length of 10 amino acids. In some embodiments, a peptide barcode has been determined to bind specifically to a particular group of polypeptide binders within a set of binders.

In some embodiments, a peptide barcode has an amino acid sequence selected from a group consisting of SEQ ID NOs: 5347-8398. In some embodiments, an encoding sequence is selected from a group consisting of SEQ ID NOs: 1148-4199.

The present disclosure provides a library comprising a plurality of nucleic acids. In some embodiments, a plurality of nucleic acids together encodes a collection of peptide barcodes. In some embodiments, each nucleic acid comprises, in order from 5' to 3' or 3' to 5', one or more of: a) a first invariant sequence (e.g. a linker sequence or a payload sequence); b) a variant sequence that is at least 9 nucleotides long, and c) a second invariant sequence (e.g. a linker sequence, a stop codon, or a payload sequence).

In some embodiments, a variant sequence is at least 15, 24, 27, 45, 150, or 300, nucleotides long.

In some embodiments, a library further comprises one or more of: d) sequence contains short helical motif; e) sequence contains a disordered motif; f) an invariant sequence which links sequence to protein of interest.

In some embodiments, each peptide barcode of a collection binds specifically to a particular group of polypeptide binders within a set of binders. In some embodiments, each peptide barcode of a collection binds specifically to one or more polypeptide binders within a set of binders.

The present disclosure provides a nucleic acid whose nucleotide sequence is or comprises a sequence encoding a polypeptide binder moiety. In some embodiments, a polypeptide binder moiety has a length within a range of 10 to 400 amino acids. In some embodiments, a polypeptide binder moiety has been determined to bind specifically to a particular group of peptide barcodes within a collection of barcodes.

In some embodiments, a polypeptide binder moiety has an amino acid sequence selected from a group consisting of SEQ ID NOs: 4200-5346. In some embodiments, an encoding sequence is selected from a group consisting of SEQ ID NOs: 1-1147.

The present disclosure provides a library comprising a plurality of nucleic acids. In some embodiments, a plurality together encodes a set of polypeptide binder moieties. In some embodiments, each nucleic acid comprises, in order from 5' to 3' or 3' to 5': a) a first invariant sequence (e.g. an antibody germline sequence (e.g. IGHV/IGKV)); b) a first variant sequence that is at least 10 nucleotides long (e.g. a CDR (e.g. CDR3) sequence); and c) a second invariant sequence (e.g. an antibody germline sequence (e.g. IDHJ/IGKJ)).

In some embodiments, each nucleic acid further comprises one or more of: d) a stop codon (e.g. after a second invariant sequence); e) a linker sequence; f) a third invariant sequence (e.g. an antibody germline sequence (e.g. IGHV/IGKV)); g) a second variant sequence that is at least 10 nucleotides long (e.g. a CDR (e.g. CDR3) sequence); and h) a fourth invariant sequence (e.g. an antibody germline sequence (e.g. IDHJ/IGKJ)).

The present disclosure provides, among other things, a library of phage particles, each phage particle comprising one or more nucleic acids as described herein.

In some embodiments, a phage is selected from a group consisting of M13, T4, T7, Lambda, and filamentous phage. In some embodiments, a phage is M13.

The present disclosure provides a set of barcode and binders. In some embodiments, each barcode is a peptide between 1 to 100, 5 to 50, 8 to 25, 9 to 25, or 9 to 15 amino acids in length that binds specifically to a particular group of binders among binders in a set. In some embodiments, each binder is a polypeptide that binds specifically to at least one barcode among barcodes in a set.

In some embodiments, specific binding is observed when binders are expressed on phage that are contacted with barcodes. In some embodiments, each binder is expressed on a phage.

The present disclosure provides a kit comprising a set of binders, each of which is a polypeptide that binds specifically to at least a particular peptide barcode in a collection barcodes. In some embodiments, each binder is provided as a polypeptide, a nucleic acid encoding a polypeptide, or both. In some embodiments, one or more of binders is provided as a phage particle, or collection thereof, engineered to express a binder. In some embodiments, one or more of binders is provided as a nucleic acid in a phagemid vector, or as an insert suitable for cloning into a phage vector.

In some embodiments, a kit further comprises information designating peptide barcodes for each binder. In some embodiments, each binder has been determined to bind specifically to at least a particular peptide barcode within a collection of barcodes that each bind specifically to at least one binder in a set.

In some embodiments, a kit further comprises a set of instructions to perform sequencing of one or more phage particles bound to one or more barcodes. In some embodiments, a kit further comprises a computer readable program for decoding sequencing data. In some embodiments, a kit further comprises reagents to express a binder on a phage particle.

In some embodiments, a kit comprises nucleic acids that encode one or more barcodes. In some embodiments, a kit comprises nucleic acids that encode one or more binders.

The present disclosure provides a method of pharmacokinetic screening. In some embodiments, a method comprises injecting a set of barcoded therapeutic candidate proteins into an animal. In some embodiments, each barcoded therapeutic candidate protein comprises a specific peptide barcode. In some embodiments, a method comprises obtaining a sample from an animal; purifying one or more barcoded therapeutic candidate proteins from a sample; contacting a sample with a set of binders (e.g. binding agents with binders expressed on them) which includes at least one particular binder specific for each barcode in a sample; and determining relative amounts of each binder present in a sample to determine each barcoded therapeutic candidate proteins' pharmacokinetic properties or biodistribution.

In some embodiments, purified proteins may be a subset of barcoded therapeutic candidate proteins which are injected into an animal.

In some embodiments, multiple samples may be obtained from an animal.

In some embodiments, an animal is a mammal. In some embodiments, an animal is a human. In some embodiments, an animal is genetically modified to express barcoded payloads (e.g. barcoded proteins).

In some embodiments, an animal is a model for a disease, disorder, or condition. In some embodiments, a disease, disorder, or condition is cancer, autoimmune, neurodegenerative, or a pathogenic (e.g. viral/bacterial) disease, disorder, or condition.

In some embodiments, a step of determining comprises (i) sequencing nucleic acid from binding agents expressing a binder; (ii) decoding relative amounts of each barcode present thereby determining relative amounts of each therapeutic candidate protein; and/or (iii) performing one or more of FACS, or MACS (magnetic activated cell sorting), affinity based purification.

In some embodiments, a step of determining comprises quantifying number of binders that bind to a barcoded payload (e.g. barcoded protein (e.g. barcoded therapeutic protein)). In some embodiments, quantifying is performed by decoding a nucleotide sequence of each binder that binds to a barcoded payload (e.g. barcoded protein).

In some embodiments, a number of nucleotide sequences provides a measure of payload (e.g. target protein) in a population of barcoded payloads (e.g. barcoded proteins).

In some embodiments, a step of injecting comprises administering barcoded payloads (e.g. barcoded proteins, barcoded therapeutic candidate proteins, etc.) orally or intravenously. In some embodiments, barcoded payloads (e.g. barcoded proteins) are injected (e.g. delivered) by viral delivery or mRNA delivery.

The present disclosure provides a method of characterizing a collection of peptide barcodes comprising: providing: (i) a library of phage particles, wherein each phage particle is designed to express a polypeptide binder, and wherein each binder binds to one or more peptide barcodes; (ii) a collection of peptide barcodes; contacting each phage particle with each barcode to form bound phage-barcode particles; determining an amount of binding between each phage particle and barcode; and identifying phage-barcode pairs that bind specifically to each other among barcodes in a collection and phages in a library.

The present disclosure provides a method of characterizing a collection of peptide barcodes comprising: providing: (i) a set of binders, wherein each binder is a polypeptide that binds to one or more peptide barcodes; (ii) a collection of peptide barcodes; contacting each binder with each barcode to form bound binder-barcode particles; determining a relative amount of binding between each polypeptide binder and peptide barcode; and identifying binder-barcode pairs that bind specifically to each other among barcodes in a collection and binders in a set.

The present disclosure provides a database of amino acid or encoding nucleic acid sequences for a collection of peptide barcodes, which database is embodied in a computer readable format. In some embodiments, each barcode sequence has a length within a range of 1 to 100, 5 to 50, 8 to 25, 9 to 25, or 9 to 15 amino acids. In some embodiments, each barcode sequence has been determined to bind specifically to one or more polypeptide binders within a set of binders that each bind specifically to one or more of barcodes in a collection.

In some embodiments, a binding pattern of one or more polypeptide binders to a barcode is used to identify a peptide barcode.

The present disclosure provides a database of amino acid or encoding nucleic acid sequences for a set of polypeptide binders. In some embodiments, a database is embodied in a computer readable format. In some embodiments, each binder sequence has a length within a range of 10 to 400 amino acids. In some embodiments, each binder sequence has been determined to bind specifically to one or more peptide barcodes within a collection of barcodes that each bind specifically to one or more of binders in a set.

The present disclosure provides, among other things, a database of amino acid or encoding nucleic acid sequences for a set of barcode-binder associations, embodied in a computer readable format. In some embodiments, each barcode is a peptide between 1 to 100, 5 to 50, 8 to 25, 9 to 25, or 9 to 15 amino acids in length. In some embodiments, each binder is a polypeptide that binds specifically to one or more barcodes among barcodes in a set.

The present disclosure provides a set of barcode-binder association designations, embodied in a computer readable format. In some embodiments, each barcode is a peptide between 1 to 100, 5 to 50, 8 to 25, 9 to 25, or 9 to 15 amino acids in length. In some embodiments, each binder is a polypeptide that binds specifically to one or more barcodes among barcodes in a set.

In some embodiments, specific binding is observed when binders are expressed on a phage particle that are then contacted with barcodes.

The present disclosure provides a method of treatment using technologies described herein. In some embodiments, a method comprises administering a therapeutic protein that has been determined to satisfy an assessment. In some embodiments, satisfying an assessment may be by a process comprising steps of: a) subjecting a population of barcoded proteins to an assessment; b) separating those members of a population that satisfy an assessment from those that do not, so that either a positive population or a negative population, or both is identified; c) contacting a positive population, or a negative population, or each population separately from the other, with a set of binders which includes at least one particular binder specific for each barcode in a population; d) determining which binders bind to separated members, thereby determining which barcoded proteins are present in a contacted population(s); and e) identifying a therapeutic protein from barcoded proteins determined to be present in a contacted population(s).

The present disclosure provides a method of treatment comprising administering a therapeutic protein that has been determined to satisfy an assessment by a process comprising steps of: a) contacting a set of binders either with a first population, with a second population, or separately with each of a first and second populations, of barcoded proteins; b) determining which binders of a set bind to a member of a first population, a second population, or both, thereby determining which barcoded proteins are present in a contacted population(s); and c) identifying a therapeutic protein from barcoded proteins determined to be present in a contacted population(s). In some embodiments, each binder binds specifically to one or more barcode relative to other barcodes. In some embodiments, a set of binders, collectively, includes a binder specific for each barcode in a first and second populations. In some embodiments, a first and second populations have been separated from one another based on performance in an assessment.

These, and other aspects encompassed by the present disclosure, are described in more detail below and in the claims.

DEFINITIONS

Figure 1A:
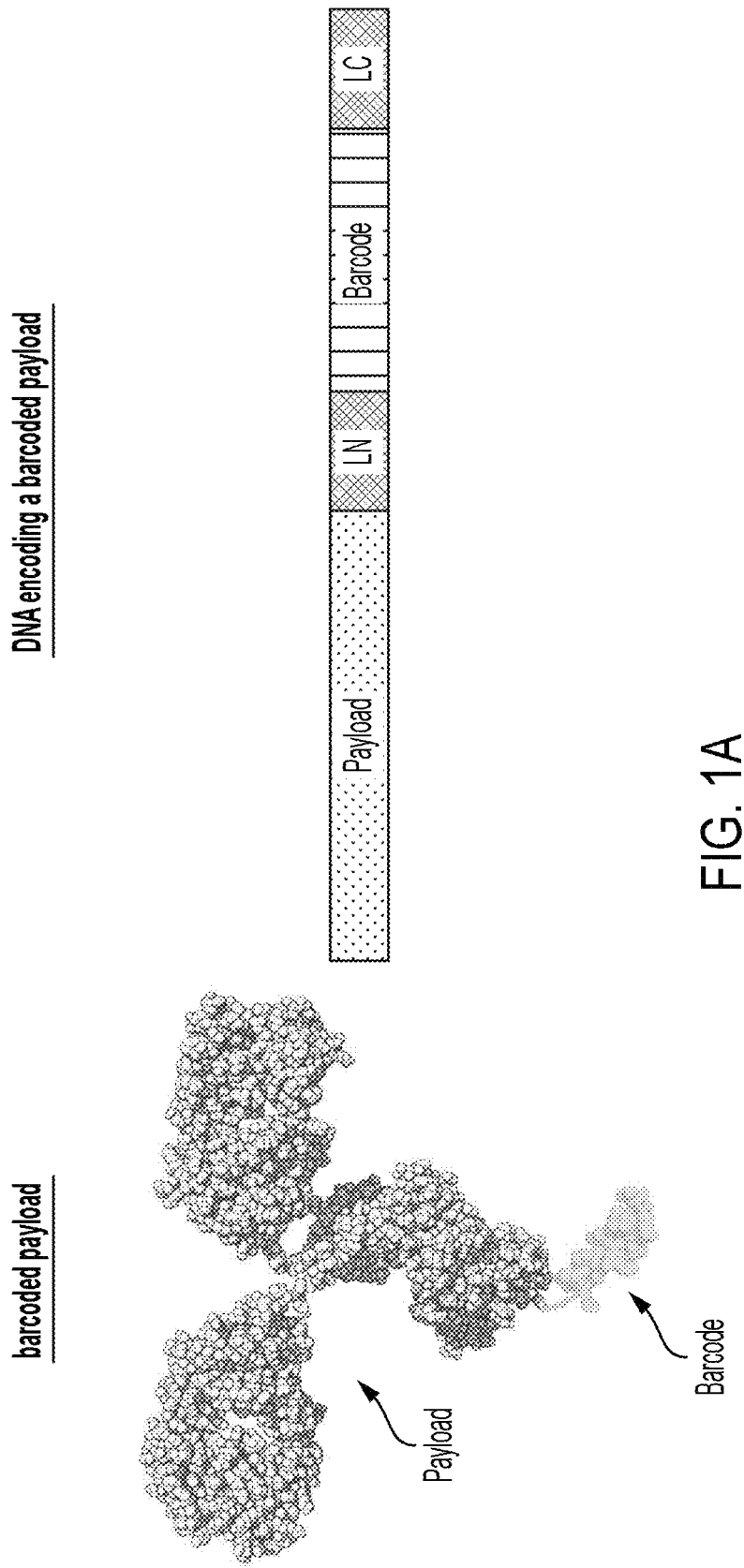
FIG. 1A is a schematic of barcoded payload as described herein, according to an illustrative embodiment. It illustrates a barcoded payload and the corresponding DNA encoding a barcoded payload. LN refers to "linker N terminus" and LC refers to "linker C terminus". In some embodiments, LN and LC sequences are constant and encode amino acids that connect the payload to the barcode. In some embodiments, LN and LC sequences are constant and are nucleic acid sequences used for modular cloning of barcodes with different payloads. In some embodiments, LN and LC sequences are flanked by Type IIS restriction site sequences.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Affinity: As is known in the art, "affinity" is a measure of the tightness with which two or more binding partners associate with one another. Those skilled in the art are aware of a variety of assays that can be used to assess affinity, and will furthermore be aware of appropriate controls for such assays. In some embodiments, affinity is assessed in a quantitative assay. In some embodiments, affinity is assessed over a plurality of concentrations (e.g., of binding partner at a time). In some embodiments, affinity is assessed in the presence of one or more potential competitor entities (e.g., that might be present in a relevant—e.g., physiological—setting). In some embodiments, affinity is assessed relative to a reference (e.g., that has a known affinity above a particular threshold [a "positive control" reference] or that has a known affinity below a particular threshold [a "negative control" reference]. In some embodiments, affinity may be assessed relative to a contemporaneous reference; in some embodiments, affinity may be assessed relative to a historical reference. Typically, when affinity is assessed relative to a reference, it is assessed under comparable conditions.

Agent: In general, the term "agent", as used herein, is used to refer to an entity (e.g., for example, a lipid, metal, nucleic acid, polypeptide, polysaccharide, small molecule, etc, or complex, combination, mixture or system [e.g., cell, tissue, organism] thereof), or phenomenon (e.g., heat, electric current or field, magnetic force or field, etc.). In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Amino acid: in its broadest sense, as used herein, refers to any compound and/or substance that can be incorporated into a polypeptide chain, e.g., through formation of one or more peptide bonds. In some embodiments, an amino acid has the general structure H$_2$N—C(H)(R)—COOH. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Animal: as used herein refers to any member of the animal kingdom. In some embodiments, "animal" refers to humans, of either sex and at any stage of development. In some embodiments. "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs®"); single chain or Tandem diabodies (TandAb®); VHHs; Anticalins®; Nanobodies® minibodies; BiTE®s; ankyrin repeat proteins or DARPiNs®; Avimers®; DARTs; TCR-like antibodies; Adnectins®; Affilins®; Trans-Bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs®"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins; Trans-Bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Associated: Two events or entities are "associated" with one another, as that term is used herein, if the presence, level, degree, type and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Barcode: As used herein, the term "barcode" refers to a peptide sequence, which associates with a binder with known specificity and affinity. In some embodiments, a barcode binds to a specific antibody-agent. In some embodiments, a barcode may be contained within a specific payload of interest. In some embodiments, a barcode may be terminal to a specific payload of interest. In some embodiments, a barcode may be synthetic. In some embodiments, a barcode may be designed. For example, a barcode sequence may be ordered as a DNA polynucleotide and cloned into the payload of interest using methods of molecular cloning known to a person of ordinary skill in the art.

Binder: As used herein, the term "binder" or "binder moiety" refers to a polypeptide sequence, which associates with a barcode with known specificity and affinity. In some embodiments, a binder is or comprises an antibody agent. In some embodiments, a binder is expressed on a surface of a binding agent. In some embodiments, a binder may bind to one or more barcodes.

Binding: It will be understood that the term "binding" or "bind", as used herein, typically refers to a non-covalent association between or among two or more entities. "Direct" binding involves physical contact between entities or moieties; indirect binding involves physical interaction by way of physical contact with one or more intermediate entities.

Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Binding agent: In general, the term "binding agent" is used herein to refer to any entity that binds to a target of interest as described herein (e.g. a barcode, a barcoded target, etc.). In many embodiments, a binding agent of interest is one that binds specifically with its target in that it discriminates its target from other potential binding partners in a particular interaction contact. In general, a binding agent may be or comprise an entity of any chemical class (e.g., polymer, non-polymer, small molecule, polypeptide, carbohydrate, lipid, nucleic acid, etc) or biological class (e.g. bacteria, phage, ribosome, mRNA. DNA, etc.). In some embodiments, a binding agent is a single chemical entity. In some embodiments, a binding agent is a complex of two or more discrete chemical entities associated with one another under relevant conditions by non-covalent interactions. For example, those skilled in the art will appreciate that in some embodiments, a binding agent may comprise a "generic" binding moiety (e.g., one of biotin/avidin/streptavidin and/or a class-specific antibody) and a "specific" binding moiety (e.g., an antibody or aptamers with a particular molecular target) that is linked to the partner of the generic biding moiety. In some embodiments, such an approach can permit modular assembly of multiple binding agents through linkage of different specific binding moieties with the same generic binding moiety partner. In some embodiments, binding agents are or comprise phages. In some embodiments, binding agents are or comprise polypeptides (including, e.g., antibodies or antibody fragments). In some embodiments, binding agents are or comprise small molecules. In some embodiments, binding agents are or comprise nucleic acids. In some embodiments, binding agents are or comprise aptamers. In some embodiments, binding agents are polymers; in some embodiments, binding agents are not polymers. In some embodiments, binding agents are non-polymeric in that they lack polymeric moieties. In some embodiments, binding agents are or comprise carbohydrates. In some embodiments, binding agents are or comprise lectins. In some embodiments, binding agents are or comprise peptidomimetics. In some embodiments, binding agents are or comprise scaffold proteins. In some embodiments, binding agents are or comprise mimeotopes. In some embodiments, binding agents are or comprise stapled peptides. In certain embodiments, binding agents are or comprise nucleic acids, such as DNA or RNA.

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow, blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

CDR: As used herein, "CDR" refers to a complementarity determining region within an antibody variable region. There are three CDRs in each of the variable regions of the heavy chain and the light chain, which are designated CDR1. CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

Comparable: As used herein, the term "comparable" refers to two or more agents, entities, situations, sets of conditions, that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Decoding: As used herein, the term "decoding", refers to a laboratory and/or bioinformatics process of identifying and quantifying a unique set of amino acids within a barcode. In some embodiments, such identification and quantification is achieved using nucleic acid (e.g. DNA) counts form a sequencing experiment and measuring an abundance of binder counts. In some embodiments, previously measured fingerprints (e.g. binder fingerprint or barcode fingerprint) are used to determine the relationship between an unknown barcode mixture, which is being decoded, for example, by comparing to a previously known mixture's binder counts, across binders with known and varying affinities to several barcodes within the pool.

Designed: As used herein, the term "designed" refers to an agent (i) whose structure is or was selected by the hand of man, (ii) that is produced by a process requiring the hand of man; and/or (iii) that is distinct from natural substances and other known agents.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Engineered: In general, the term "engineered" refers to the aspect of having been manipulated by the hand of man. For example, in some embodiments, a small molecule may be considered to be engineered if its structure and/or production is designed and/or implemented by the hand of man. Analogously, in some embodiments, a polynucleotide may be considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first sequence (e.g. coding sequence) but not in operative association with a second sequence (e.g. coding sequence), is linked by the hand of man so that it is operatively associated with the second sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, expression products of an engineered polynucleotide, and/or progeny of an engineered polynucleotide or cell are typically still referred to as "engineered" even though the actual manipulation was performed on a prior entity.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein, and/or (4) post-translational modification of a polypeptide or protein.

Fingerprint: As used herein, the term "fingerprint" refers to the counts of one or more unknown agents that a known agent may bind to or be associated with. In some embodiments, a fingerprint may be for a known barcode or barcode mixture. In some embodiments, a fingerprint may be for a known binder or binder mixture. For example, in some embodiments, a fingerprint (e.g. barcode fingerprint) may refer to the counts of one or more binders (e.g. determined through sequencing analysis) to bind specifically to a known barcode or barcode mixture. That is, in some embodiments, a fingerprint for a barcode refers to the counts of one or more binders, some of which may have high affinity for the barcode, and some of which may have low affinity for the barcode. In some embodiments, a fingerprint may be used in the decoding process, which process is used to determine the relative or absolute abundance of a given barcode within a pool of barcodes. As is understood to a person of ordinary skill in the art a fingerprint may be determined for a known barcode or barcode mixture, or for a known binder or binder mixture. For example, in some embodiments, a fingerprint (e.g. binder fingerprint) may refer to the counts of one or more barcodes (e.g. determined through sequencing analysis) that bind specifically to a known binder or binder mixture. That is, in some embodiments, a fingerprint for a binder refers to the counts of one or more barcodes, some of which may have high affinity for the binder, and some of which may have low affinity for the binder. Accordingly, a fingerprint may also be used in the decoding process, in some embodiments, to determine the relative or absolute abundance of a given binder within a pool of binders.

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the whole.

Human: In some embodiments, a human is an embryo, a fetus, an infant, a child, a teenager, an adult, or a senior citizen.

"Improve," "increase", "inhibit" or "reduce": As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Library: The term "library" as used herein refers to a mixture of one or more distinct molecules. In some embodiments, all elements of a library share one or more common components. In some embodiments, all elements of a library share no common components. In some embodiments, one or more elements of a library are distinguished by one or more unique components. In some embodiments, as may be apparent from the context, a library may refer to a mixture of binding agents. In some embodiments, a library may be a phage library. In some embodiments, for example, a phage library may consist of phage with distinct binders displayed on (e.g. on a surface) of the phage and encapsulating DNA encoding for this binder within the phage. In some embodiments, a library may refer to a mixture of barcoded payload proteins. In some embodiments, a library may refer to a mixture of barcodes (e.g. peptide barcodes).

Linker: as used herein, is used to refer to that portion of a multi-element agent that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger, P., et al. (1993) Proc. Natl. Acad. Sci. USA 90:6444-6448; Poljak, R. J., et al. (1994) Structure 2: 1 121-1123).

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide. In some embodiments, a nucleic acid has enzymatic activity.

Payload: As used herein, the term "payload" refers to a protein sequence, which may be associated to a peptide barcode through at least one covalent bond. In some embodiments, a payload is a protein that is to be detected in a pool of proteins. In some embodiments, a payload is an unmodified protein that is to be detected in a pool of proteins without attaching a peptide barcode. In some embodiments, a payload is a modified protein that is to be detected in a pool of proteins. In some embodiments, a payload may be associated with a barcode (e.g. peptide barcode). In some embodiments, a payload may not be associated with a barcode (e.g. peptide barcode).

Peptide: The term "peptide" as used herein refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Polypeptide: As used herein refers to any polymeric chain of residues (e.g., amino acids) that are typically linked by peptide bonds. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain l-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. In some embodiments, proteins are antibodies, antibody fragments, biologically active portions thereof, and/or characteristic portions thereof.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Sample: As used herein, the term "sample" typically refers to an aliquot of material obtained or derived from a source of interest. In some embodiments, as would be appreciated from the context by a person of ordinary skill in the art, the term "sample" may be used interchangeably with terms like "mixture", or "complex mixture", or "complex sample". In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a biological tissue or fluid may be or comprise cells, serum, extracellular matrix, CSF, and/or combinations or component(s) thereof. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., bronchoalveolar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

Specific: The term "specific", when used herein with reference to an agent having an activity, is understood by those skilled in the art to mean that the agent discriminates between potential target entities or states. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments specificity is evaluated relative to that of a reference non-specific binding agent. In some embodiments, the agent or entity does not detectably bind to the competing alternative target under conditions of binding to its target entity. In some embodiments, binding agent binds with higher on-rate, lower off-rate, increased affinity, decreased dissociation, and/or increased stability to its target entity as compared with the competing alternative target(s).

Subject: As used herein, the term "subject" refers to an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease. disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans. In some embodiments, a therapeutic agent is a therapeutic protein.

DETAILED DESCRIPTION

I. Barcoded Payloads

Methods and systems to generate and use barcodes and barcoded payloads are described herein. In some embodiments, methods disclosed herein are used to detect and/or characterize payloads. In some embodiments, methods disclosed herein are used to detect and/or characterize proteins. In some embodiments, methods disclosed herein are used to detect and/or characterize therapeutic proteins. In some embodiments, methods disclosed herein are used to detect and/or characterize or non-therapeutic proteins. In some embodiments, methods disclosed herein are used to detect and/or characterize proteins by tagging them with barcodes (e.g. barcoded proteins). In some embodiments, methods disclosed herein are used to detect and/or characterize proteins in vitro. In some embodiments, methods disclosed herein are used to detect and/or characterize proteins in vivo. In some embodiments, methods disclosed herein are used to detect and/or characterize a protein. In some embodiments, methods disclosed herein are used to detect and/or characterize multiple (e.g. two or more, three or more, four or more, etc.) proteins.

Barcodes:

In some embodiments, a barcode is or comprises an amino acid sequence. In some embodiments, a barcode is or comprises an amino acid sequence that occurs in nature. In some embodiments, a barcode is or comprises an amino acid sequence that does not occur in nature. In some embodiments, a barcode is or comprises an amino acid sequence that is synthetic. In some embodiments, a barcode comprises naturally occurring amino acids. In some embodiments, a barcode comprises non-naturally occurring amino acids (e.g. modified amino acids). In some embodiments, a barcode is or comprises a peptide barcode.

Barcodes of the present disclosure can be of varying lengths. For example, in some embodiments, a barcode may have a length ranging between 1 and 100 amino acids. In some embodiments, a barcode may have a length ranging between 5 and 50 amino acids. In some embodiments, a barcode may have a length ranging between 8 and 25 amino acids. In some embodiments, a barcode may have a length ranging between 9 and 25 amino acids. In some embodiments, a barcode may have a length ranging between 9 and 15 amino acids. In some embodiments, a barcode may have a length of 1, 2, 3, 4, 5, 6, 7, 8, 9, 10, 11, 12, 13, 14, 15, 16, 17, 18, 19, 20, 21, 22, 23, 24, or 25 amino acids. In some embodiments, a barcode may have a length of at least 5 amino acids. In some embodiments, a barcode may have a length of at most 100 amino acids.

Barcodes, as described herein may be available in a library in different formats. For example, in some embodiments a barcode as described herein may be described as a nucleic acid sequence. In other instance, a barcode as described herein may be described as an amino acid sequence. A person of ordinary skill in the art will appreciate that barcodes described in one format may be converted to another format using basic biological principles. Accordingly, barcodes described as nucleic acid sequences may be translated in to proteins, which may be used to detect the presence or absence of a payload (e.g. protein) in a mixture. Such a translated barcode is referred to herein as a peptide barcode.

Accordingly, barcodes of the present disclosure when described using nucleic acids may have lengths different from amino acid sequence lengths disclosed in the paragraph above. For example, in some embodiments, a barcode may have a length ranging between 3 and 300 nucleotides. In some embodiments, a barcode may have a length ranging between 15 and 150 nucleotides. In some embodiments, a barcode may have a length ranging between 24 and 75 nucleotides. In some embodiments, a barcode may have a length ranging between 27 and 75 nucleotides. In some embodiments, a barcode may have a length ranging between 27 and 45 nucleotides. In some embodiments, a barcode may have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 nucleotides. In some embodiments, a barcode may have a length of at least 15 nucleotides. In some embodiments, a barcode may have a length of at most 300 nucleotides.

Barcodes of the present disclosure may have one or more properties. In some embodiments, a barcode may be naturally occurring. In some embodiments, a barcode may not be naturally occurring (e.g. synthetic). In some embodiments, a barcode may have relatively no effect on payload function. For example, in some embodiments, tagging a payload (e.g. a protein) with a barcode as described herein does not alter or change relatively the function of the tagged payload. In some embodiments, a barcode may have an effect (e.g. positive or negative) on payload function. For example, in some embodiments, tagging a payload (e.g. a protein) with a barcode as described herein may alter or change relatively a function (e.g. half-life (e.g. longer half-life), enhance targeting to specific tissue, etc.) of the tagged payload. In some embodiments, a barcode may not illicit an immune response (e.g. an IgG response, a complement response, etc.). In some embodiments, barcodes are orthogonal to each other. In some embodiments, barcodes are not orthogonal to each other.

Barcodes of the present disclosure may be attached to various positions of a payload. For example, in some embodiments, a barcode may be attached to an optimal position on a payload. In some embodiments, a barcode may be attached to a non-optimal position on a payload. In some embodiments, a barcode may be attached to an optimal position on a protein. For example, in some embodiments, a barcode may be attached to an N-terminus of a protein. In some embodiments, a barcode may be attached to a C-terminus of a protein. In some embodiments, a barcode may be attached to a non-terminal position on a protein (e.g. side chain). In some embodiments, a barcode may be attached to a non-optimal position on a protein.

Among other things, barcodes (e.g. peptide barcodes or nucleic acids encoding peptide barcodes) of the present disclosure may be flanked by additional sequences (e.g. nucleic acid sequences, amino acid sequences, etc.). In some embodiments, a barcode may be flanked by additional sequences on a barcode's 5' end. In some embodiments, a barcode may be flanked by additional sequences on a barcode's 3' end. In some embodiments, a barcode may be flanked by additional sequences on a barcode's 3' and 5' end. In some embodiments, an additional sequence may be a primer binding site, a restriction endonuclease recognition sequence, a restriction enzyme site (e.g. a cleavage site), a sequence that encodes an amino acid sequence, a sequence that does not encode an amino acid sequence, an amino acid sequence, or a nucleic acid sequence. For example, in some embodiments, a barcode may be flanked by nucleic acid sequences encoding an amino acid sequence. In some embodiments, a barcode may be flanked by nucleic acid sequences that does not encode an amino acid sequence. In some embodiments, a barcode may be flanked by amino acid sequences. In some embodiments, a peptide barcode may be flanked by amino acid sequences (e.g. Glycine-Serine (GS)). Analogously, in some embodiments, a nucleic acid encoding a peptide barcode of the present disclosure may be flanked by additional sequences (e.g. nucleic acid sequences, amino acid sequences, etc.). In some embodiments, a nucleic acid encoding a peptide barcode may be flanked by nucleic acid sequences on a 5' end. In some embodiments, a nucleic acid encoding a peptide barcode may be flanked by nucleic acid sequences on a 3' end. In some embodiments, a nucleic acid encoding a peptide barcode may be flanked by nucleic acid sequences on a 3' and 5' end. In some embodiments, a nucleic acid encoding a peptide barcode may be flanked by nucleic acid sequences encoding an amino acid sequence comprising a Glycine-Serine (GS).

In some embodiments, a barcode may be flanked by restriction endonuclease recognition sequences. In some embodiments, a barcode may be flanked by restriction endonuclease recognition sequences on a barcode's 5' end.

In some embodiments, a barcode may be flanked by restriction endonuclease recognition sequences on a barcode's 3' end. In some embodiments, barcode may be flanked by restriction endonuclease recognition sequences on a barcode's 3' and 5' end. In some embodiments, a nucleic acid encoding a peptide barcode may be flanked by restriction endonuclease recognition sequences. In some embodiments, a nucleic acid encoding a peptide barcode may be flanked by restriction endonuclease recognition sequences on a 5' end. In some embodiments, a nucleic acid encoding a peptide barcode may be flanked by restriction endonuclease recognition sequences on a 3' end. In some embodiments, a nucleic acid encoding a peptide barcode may be flanked by restriction endonuclease recognition sequences on a 3' and 5' end. In some embodiments, a restriction endonuclease recognition sequence may be recognized by one or more restriction enzymes (e.g. BsaI, BsmBI, BbsI, SapI, etc.). In some embodiments, restriction endonuclease recognition sequences are Type I, Type II, or Type Its restriction endonuclease recognition sequences. Such recognition sequences, for example, may be used to produce universal overhangs that may be used in cloning peptide barcodes into different locations of various payload. Such flexibility allows a barcode to be used to detect different protein payloads in different experiments.

In some embodiments, a nucleic acid sequence encoding a barcode (e.g. a peptide barcode) may be associated with (e.g. attached to, linked to) a second nucleic acid sequence encoding a payload (e.g. a protein payload of interest). Such nucleic acid sequences, for example, may be translated to form barcoded payloads (e.g. barcoded proteins). In some embodiments, a nucleic acid sequence encoding a barcode (e.g. a peptide barcode) is separate from a second nucleic acid sequence encoding a payload (e.g. a protein payload of interest). For such nucleic acid sequences, for example, a nucleic acid sequence encoding a barcode may be translated separately from a second nucleic acid sequence encoding a payload, and subsequently attached using one or more methods known in the art to join distinct amino acid sequences (e.g. using linkers).

Barcodes of the present disclosure may be associated (e.g. directly or indirectly attached) to payloads so as to form barcoded payloads. For example, in some embodiments, each barcode sequence (e.g. peptide barcode sequence) may be associated to only one payload of interest (e.g. protein of interest) within a mixture. In some embodiments, each barcode sequence may be associated to more than one payload of interest (e.g. payloads with different sequences) within a mixture. In some embodiments, multiple (e.g. two or more, three or more, four or more, etc.) barcode sequences may be associated to one payload of interest within a mixture. For example, in some embodiments, one or more barcode sequences may be associated to various different positions on a given payload—such a setup may be useful in, for example, in studying and identifying the stability and/or cleavage of such barcoded payloads. In some embodiments, each payload in a mixture is a unique sequence (e.g. each payload has a different sequence from every other payload in the mixture). In some embodiments, each payload in a mixture is a non-unique sequence.

Various methods and parameters may be used to select suitable barcodes for a given payload. For example, stability of a barcoded payload is key in determining if a payload may be tagged by said barcode. In some embodiments, a barcode may be tagged to a specific payload across different experiments. In some embodiments, a barcode may be tagged to different payloads in different experiments. For example, in some embodiments, a barcode may be tagged to two or more, three or more, four or more, ten or more, 100 or more, 1000 or more, or 10,000 or more different payloads across different experiments.

In some embodiments, a barcode may be associated with only one payload in a given experiment. In some embodiments, a barcode may be associated with multiple payloads in a given experiment. For example, in some embodiments, one or more barcodes are associated with multiple payloads (i.e. a barcode is tagged to multiple payloads) in a mixture, such that each payload is associated with a unique set of barcodes within the mixture. That is, each payload may be associated with a unique "pattern" of barcodes in the mixture. Analogously, in some embodiments, several payloads may be associated with the same barcode.

Among other things, barcodes described herein are designed to have a distinct (i.e. unique) sequence. In some embodiments, a barcode is designed to have a distinct sequence (e.g. distinct from another barcode). For example, each barcode is designed to be distinct (e.g. unique) from every other barcode used in an experiment, such that each payload (e.g. protein to be measured) is attached to at least one barcode, and each barcode (e.g. barcode with a specific sequence) is only attached to one payload. As may be understood by a person of ordinary skill in the art, the diversity of barcodes contained within a pool is limited only by the possible diversity of amino acid sequences for a given barcode length. For example, for a barcode length 'N', there exists $20^N$ distinct amino acid barcode sequences of length N (if only unmodified/naturally occurring amino acids are used). That is, for a barcode length of 15, the theoretical limit is $20^{15}$, or $3.2768 \times 10^{19}$.

Example of barcodes according to various embodiments of the present disclosure are listed in Tables 1 and 2. In some embodiments, a barcode (e.g. peptide barcode) is or comprises an amino acid sequence selected from SEQ ID NOs: 5347-8398. In some embodiments, a barcode (e.g. peptide barcode) is encoded by a sequence that is or comprises a nucleic acid sequence selected from SEQ ID NOs: 1148-4199.

Payload:

Methods and systems disclosed herein are may be used for detection of one or more payloads as described herein. In some embodiments, a payload is a protein of interest. In some embodiments, a payload is a protein that has a therapeutic function. In some embodiments, a payload is a protein that does not have a therapeutic function (e.g. may aid another payload with a therapeutic function). For example, possible payloads are proteins which one may wish to screen as drugs, such as monoclonal antibodies, single domain antibodies, enzymes, bispecific antibodies or any other protein which may have therapeutic function.

In one aspect, systems and methods disclosed herein may be used for detecting a payload (e.g. protein) in a mixture. Specifically, barcodes disclosed herein tagged to a payload (e.g. barcoded payload (e.g. barcoded protein)) in a mixture and used to detect said payload in the mixture. In some embodiments, each payload is different from every other payload in a mixture. In some embodiments, each payload in a mixture is different from every other payload in a mixture by at least one amino acid. In some embodiments, each payload in a mixture is different from every other payload in a mixture by two or more amino acids. In some embodiments, a payload (e.g. in a mixture) may be tagged with a barcode. In some embodiments, each payload (e.g. in a mixture) may be tagged with a same barcode. In some embodiments, each payload (e.g. in a mixture) may be tagged with different barcode. In some embodiments, a payload (e.g. in a mixture) may be tagged with a barcode that is different from every other barcode (e.g. associated with other payloads) in a mixture by at least one amino acid. In some embodiments, a payload (e.g. in a mixture) may be tagged with a barcode that is different from every other barcode (e.g. associated with other payloads) in a mixture by two or more amino acids.

As discussed elsewhere in the specification, a payload may be tagged with different barcodes (e.g. in different mixtures, different experiments, etc.). For example, as noted above, in some embodiments, each barcode sequence may be attached to only one payload of interest within a mixture. In some embodiments, each barcode sequence may be attached to more than one payload of interest (e.g. payloads with different sequences) within a mixture. In some embodiments, multiple (e.g. two or more, three or more, four or more, etc.) barcode sequences may be attached to one payload of interest within a mixture. For example, in some embodiments, one or more barcode sequences may be attached to various different positions on a given payload—such a setup may be useful in, for example, in studying and identifying the stability of such barcoded payloads. In some embodiments, each payload in a mixture is a unique sequence (e.g. each payload has a different sequence from every other payload in the mixture). In some embodiments, each payload in a mixture is a non-unique sequence.

In some embodiments, a payload may be tagged to a specific barcode across different experiments. In some embodiments, a payload may be tagged to different barcodes in different experiments. For example, in some embodiments, a payload may be tagged to two or more, three or more, four or more, ten or more, 100 or more, 1000 or more, or 10,000 or more different barcodes across different experiments.

In some embodiments, a payload may be associated with only one barcode in a given experiment. In some embodiments, a payload may be associated with multiple barcodes in a given experiment. For example, in some embodiments, one or more barcodes (e.g. in a mixture) are associated with multiple payloads (i.e. a barcode is tagged to multiple payloads) in a mixture, such that each payload is associated with a unique set of barcodes within the mixture. That is, each payload may be associated with a unique "pattern" of barcodes in the mixture. In some embodiments, several payloads may be associated with the same barcode.

Linkers:

Among other things, systems and methods described herein may use linkers. In some embodiments, a payload as described herein and a barcode as described herein are separated by a linker. In some embodiments, linkers (L) provide distance between a payload (P) and a barcode (b). That is, structurally a barcoded payload, in some embodiments, may have a sequence of P-L-b. This, for example, may contribute to folding characteristics, payload functionality, and/or payload stability.

In some embodiments, linkers may be nucleic acids. In some embodiments, linkers may be amino acids. Linkers as described herein may have varying lengths. For example, in some embodiments, a linker may have a length of at least 3 amino acids. In some embodiments, a linker may have a length of between 1 and 50 amino acids (e.g. between 1 and 30 amino acids).

In some embodiments, linkers of the present invention may be cleaved upon treatment. For example, in some embodiments, a linker may comprise one or more motifs that may be cleaved upon treatment.

In some embodiments, linkers of the present invention may be resistant to cleavage. In some embodiments, linkers of the present invention may be resistant to cleavage in assays. In some embodiments, linkers of the present invention may be resistant to cleavage in vivo.

In one aspect, linkers may be used to tag barcodes. In some embodiments, each linker sequence is associated with a distinct barcode sequence. For example, in some embodiments, a linker sequence may be used as a unique tag associated with a distinct barcode sequence (e.g. nucleic acid sequence) in a mixture. That is, in some embodiments, such a linker may be used to amplify an associated barcode sequence. For example, in some embodiments, such a linker may be used as a primer to amplify an associated barcode sequence. Subsequently, in some embodiments, an amplified linker may be used to isolate an associated barcode sequence, allowing for retrieval of the barcode sequence (e.g. nucleic acid sequence) from a given linker-barcode pair. In some embodiments, a linker-barcode pair may be subject to DNA sequencing for identification of the barcode sequence.

In some embodiments, a nucleic acid sequence encoding for a linker-barcode pair may be used to associate (e.g. link) the linker-barcode pair to a new payload.

II. Binders and Binding Agents

Binders:

In some embodiments, a binder (i.e. a binder moiety) is or comprises a nucleic acid sequence. In some embodiments, a binder is or comprises a nucleic acid sequence that occurs in nature. In some embodiments, a binder is or comprises a nucleic acid sequence that does not occur in nature. In some embodiments, a binder is or comprises a nucleic acid sequence that is synthetic. In some embodiments, a binder comprises naturally occurring nucleic acids. In some embodiments, a binder comprises non-naturally occurring nucleic acids (e.g. modified nucleic acids).

In some embodiments, a binder nucleic acid sequence is or comprises a sequence that encodes for a polypeptide sequence. For example, in some embodiments, a binder nucleic acid sequence may contain a region, which encodes for a polypeptide sequence conferring high affinity and/or specificity for a given barcode (e.g. peptide barcode). In some embodiments, a binder nucleic acid sequence is or comprises a sequence that encodes for an antibody. In some embodiments, a binder nucleic acid sequence is or comprises a sequence that encodes for a fragment of an antibody. In some embodiments, a binder nucleic acid sequence is or comprises a sequence that encodes for a single-chain variable Fragment (scFv). As may be known to those of ordinary skill in the art, a scFv is a fusion protein of the variable regions of the heavy ($V_H$) and light chains ($V_L$) of immunoglobulins. In some embodiments, a $V_H$ and $V_L$ chain may be connected with a short linker peptide (e.g. linker of about 5-50 amino acids in length, 10-25 amino acids in length, etc.).

In some embodiments, for example, a binder is generated to have known specificity and affinity for a given barcode. In some embodiments, a binder is generated to have known specificity and affinity for one barcode. In some embodiments, a binder is generated to have known specificity and affinity for multiple (e.g. two or more, three or more, etc.) barcodes. In some embodiments, a binder is generated to have known specificity and affinity for at least one barcode. In some embodiments, a binder, for example, is expressed on the surface of a binding agent (e.g. a phage, a ribosome, etc.) using methods known to those skilled in the art.

In some embodiments, a binder associates with a barcode (e.g. with known specificity and affinity).

In some embodiments, a binder is or comprises a polypeptide sequence that occurs in nature. In some embodiments, a binder is or comprises a polypeptide sequence that does not occur in nature. In some embodiments, a binder is or comprises a polypeptide sequence that is synthetic. In some embodiments, a binder comprises naturally occurring amino acids. In some embodiments, a binder comprises non-naturally occurring amino acids (e.g. modified amino acids).

Binders of the present invention may be of varying lengths. For example, in some embodiments, a binder may have a length ranging between 5 to 1000 amino acids. In some embodiments, a binder may have a length ranging between 5 to 800 amino acids. In some embodiments, a binder may have a length ranging between 6 to 500 amino acids. In some embodiments, a binder may have a length ranging between 10 to 400 amino acids. In some embodiments, a binder may have a length ranging between 5 to 500 amino acids. In some embodiments, a binder may have a length ranging between 5 to 1000 amino acids. In some embodiments, a binder may have a length of 10 amino acids. In some embodiments, a binder may have a length of at least 5 amino acids. In some embodiments, a binder may have a length of at most 1000 amino acids.

Binders, as described herein may be available in a library in different formats. For example, in some embodiments a binder as described herein may be described as a nucleic acid sequence. In other instance, a binder as described herein may be described as an amino acid sequence. A person of ordinary skill in the art will appreciate that binders described in one format may be converted to another format using basic biological principles. Accordingly, binders described as nucleic acid sequences may be translated in to proteins, which may be used to detect the presence or absence of a payload (e.g. barcoded payload (e.g. barcoded protein)) in a mixture. Such a translated binder is referred to herein as a polypeptide binder or polypeptide binder moiety.

Accordingly, binders of the present disclosure when described using nucleic acids may have lengths different from amino acid sequence lengths disclosed in the paragraph above. For example, in some embodiments, a binder may have a length ranging between 15 to 3000 nucleotides. In some embodiments, a binder may have a length ranging between 15 to 2400 nucleotides. In some embodiments, a binder may have a length ranging between 24 to 1500 nucleotides. In some embodiments, a binder may have a length ranging between 30 to 1200 nucleotides. In some embodiments, a binder may have a length of 30 nucleotides. In some embodiments, a binder may have a length of at least 15 nucleotides. In some embodiments, a binder may have a length of at most 3000 nucleotides.

Binders of the present disclosure may have one or more specific properties. In some embodiments, a binder may be naturally occurring. In some embodiments, a binder may not be naturally occurring (e.g. synthetic). In some embodiments, a binder may not illicit an immune response (e.g. an IgG response, a complement response, etc.).

Among other things, binders (e.g. polypeptide binders, nucleic acids encoding binders) of the present disclosure, like barcodes discussed above, may be flanked by additional sequences (e.g. nucleic acid sequences, amino acid sequences, etc.). In some embodiments, a binder may be flanked by additional sequences on a binder's 5' end. In some embodiments, a binder may be flanked by additional sequences on a binder's 3' end. In some embodiments, a binder may be flanked by additional sequences on a binder's 3' and 5' end. In some embodiments, an additional sequence may be a primer binding site, a restriction endonuclease recognition sequence, a restriction enzyme site (e.g. a cleavage site), a sequence that encodes an amino acid sequence, a sequence that does not encode an amino acid sequence, an amino acid sequence, or a nucleic acid sequence.

In one aspect of the present invention, a binder nucleic acid sequence may be associated with (e.g. attached to, linked to) another nucleic acid sequence. For example, in some embodiments, a binder nucleic acid sequence may be associated with a nucleic acid sequence encoding one or more genes. In some embodiments, a binder nucleic acid sequence may be associated with a nucleic acid sequence encoding one or more genes of a phage (e.g. m13). In some embodiments, a binder nucleic acid sequence may be associated with a nucleic acid sequence encoding a polypeptide. In some embodiments, a binder nucleic acid sequence may be associated with a nucleic acid sequence encoding a polypeptide of a phage (e.g. m13 gene3 protein). The binder-gene3 protein fusion can be expressed and incorporated into m13 phage.

Among other things, binders described herein are designed to have a distinct (i.e. unique) sequence. In some embodiments, a binder is designed to have a distinct sequence (e.g. distinct from another binder). For example, each binder is designed to be distinct (e.g. unique) from every other binder used in an experiment.

In one aspect of the present invention, binders bind to barcodes or barcoded payloads, as described herein, with high specificity and high affinity. In some embodiments, a barcode or barcoded payload (e.g. barcoded protein to be measured) binds to one binder, and each binder (e.g. binder with a specific sequence) binds to one barcode or barcoded payload. In some embodiments, a barcode or barcoded payload (e.g. barcoded protein to be measured) binds to at least one binder. In some embodiments, each binder (e.g. binder with a specific sequence) binds to at least one barcode or barcoded payload. In some embodiments, multiple binders (e.g. with different sequences (e.g. polypeptide sequences)) bind to a single barcode. In some embodiments, multiple barcodes (e.g. with different sequences (e.g. peptide sequences)) bind to a single binder.

Example of binders according to various embodiments of the present disclosure are listed in Tables 1 and 2. In some embodiments, a binder (e.g. polypeptide binder) is or comprises an amino acid sequence selected from SEQ ID NOs: 4200-5346. In some embodiments, a binder (e.g. polypeptide binder) is encoded by a sequence that is or comprises a nucleic acid sequence selected from SEQ ID NOs: 1-1147.

Binding Agents:

Methods described herein relate to the detection of one or more barcodes using a binding agent. In some embodiments, a binding agent is associated with or comprises a detectable nucleic acid. In some embodiments, a binding agent expresses a detectable nucleic acid. In some embodiments, a binding agent expresses a detectable nucleic acid on its surface (e.g. a binder). In some embodiments, a binding agent expresses an antibody on its surface.

In some embodiments, for example, to detect the presence of a specific (e.g. distinct) barcode, the present invention envisions the association of a distinct detectable nucleic acid (e.g. a DNA sequence, an RNA sequence, etc.) to a specific barcode. This is achieved through contacting a barcode with a binding agent. In some embodiments, one or more barcodes may be contacted with a binding agent. In some embodiments, one or more binding agents may be contacted with a barcode.

In some embodiments, a binding agent may be or comprises a phage, a ribosome, mRNA, DNA etc. In some embodiments, a binding agent is a phage. In some embodiments, a binding agent is may be a M13 phage, T4 phage, T7 phage, Lambda phage, or filamentous phage. In some embodiments, a binding agent is may be a M13 phage.

Binders as disclosed herein may be expressed on binding agents using methods known in the art. For example, a person of ordinary skill in the art may be able to express a nucleic acid encoding a polypeptide binder on (e.g. on a surface) of a phage using techniques and methods available in the art.

III. Production

Production of Barcodes:

Disclosed herein are methods and systems for the production of barcodes for use in systems and methods of the present disclosure. In some embodiments, barcodes, as described herein, may be generated rapidly (e.g. in about a week, about 2 weeks, about 3 weeks, about 4 weeks, about 1 month, about 2 months, about 3 months, about 4 months, about 5 months, about 6 months, or about 1 year). In some embodiments, for example, between about 100 to about 1,000 barcodes may be generated rapidly. In some embodiments, between about 10 to about 1000 barcodes may be generated rapidly. In some embodiments, between about 10 to about 10,000 barcodes may be generated rapidly. While large numbers of barcodes, as described herein, may be generated rapidly, such barcodes are also robust, in that barcodes generated using the methods disclosed herein may bind specifically and with different affinities to a known set of binders.

In accordance with various embodiments, barcodes as described herein may be synthesized using a nucleic acid (e.g. oligonucleotide) array. In some embodiments, barcodes as described herein may be synthesized using a DNA array. In some embodiments, nucleic acids (e.g. oligonucleotides) of a nucleic acid array are expressed in to barcodes. In some embodiments, barcodes as described herein may be synthesized using nucleic acid library. In some embodiments, a nucleic acid library is synthesized using a nucleic acid array. In some embodiments, nucleic acids (e.g. oligonucleotides) of a nucleic acid library are expressed in to barcodes.

In some embodiments, a barcode nucleic acid library comprises about 1 or more, about 2 or more, about 3 or more, about 4 or more, about 5 or more, about 10 or more, about 50 or more, about 100 or more, about 200 or more, about 300 or more, about 400 or more, about 500 or more, about 600 or more, about 700 or more, about 800 or more, about 900 or more, about 1000 or more, about 2000 or more, about 3000 or more, about 4000 or more, or about 5000 or more potential barcodes. In some embodiments, a nucleic acid library comprises one or more potential barcode sequences. Such potential barcode sequences may be screened for functionality as peptide barcodes (i.e. after translation of potential barcode nucleic acid sequences) using one or more methods described herein.

Barcodes of the present disclosure may be screened for one or more specific properties. In some embodiments, a barcode may be screened for specific binding (e.g. specificity, binding affinity) to a binder. In some embodiments, a barcode may be screened for specific binding to one or more binders. In some embodiments, a barcode may be screened for specific binding to at least a binder. In some embodiments, a barcode may be screened for specific binding to at most a binder. In some embodiments, a barcode may be screened for specific binding to multiple binders.

As may be understood by a person of ordinary skill in the art, a barcode is designed to be distinct (i.e. unique (e.g. have a unique sequence)) in a pool of barcodes. Such distinction may be achieved, in some embodiments, by changing one or more amino acids in a barcode. In some embodiments, a barcode is distinct from other barcodes in a pool of barcodes by 1 amino acid. In some embodiments, a barcode is distinct from other barcodes in a pool of barcodes by at least 1 amino acid. In some embodiments, a barcode is distinct from other barcodes in a pool of barcodes by at most 1 amino acid. In some embodiments, a barcode is distinct from other barcodes in a pool of barcodes by 2, 3, 4, 5, 6, 7, 8, 9, 10, 11, 12, 13, 14, 15, 16, 17, 18, 19, 20, 21, 22, 23, 24, or 25 amino acids. In some embodiments, a barcode is distinct from other barcodes in a pool of barcodes by at least 2 amino acids. In some embodiments, a barcode is distinct from other barcodes in a pool of barcodes by at most 50 amino acids.

Production of Barcoded Payloads:

Barcoded payloads in accordance with the present invention may be produced in various ways. In some embodiments, payload-barcode nucleic acid sequence pairs may be inserted into a plasmid to allow for expression in different expression systems (e.g. protein expression systems). In some embodiments, at least one payload-barcode nucleic acid sequence pair is inserted into a plasmid. In some embodiments, at least two payload-barcode nucleic acid sequence pairs are inserted into a plasmid. In some embodiments, at least three payload-barcode nucleic acid sequence pairs are inserted into a plasmid. In some embodiments, one or more payload-barcode nucleic acid sequence pairs are inserted into a plasmid.

In some embodiments, a payload-barcode nucleic acid sequence may comprise additional sequences. In some embodiments, a payload-barcode nucleic acid sequence may comprise additional nucleic acid sequences. In some embodiments, a payload-barcode nucleic acid sequence may comprise a universal motif sequence. In some embodiments, a payload-barcode nucleic acid sequence may comprise at least one universal motif sequence. In some embodiments, a payload-barcode nucleic acid sequence may comprise at least two universal motif sequences. In some embodiments, a payload-barcode nucleic acid sequence may comprise two or more universal motif sequences.

In some embodiments, at least one payload-barcode nucleic acid sequences in a pool of payload-barcode nucleic acid sequences may comprise a universal motif sequence. In some embodiments, all payload-barcode nucleic acid sequences in a pool of payload-barcode nucleic acid sequences may comprise a universal motif sequence.

Different plasmids may be used to produce technologies described herein. In some embodiments, a plasmid is a DNA plasmid. In some embodiments, a plasmid is an RNA plasmid. In some embodiments, a plasmid is a fertility F-plasmid. In some embodiments, a plasmid is a resistance plasmid. In some embodiments, a plasmid is a virulence plasmid. In some embodiments, a plasmid is a degradative plasmid. In some embodiments, a plasmid is a Col plasmid.

Different hosts (e.g. host cell, host cell line, etc.) may be used to produce technologies described herein. In some embodiments, a host is a mammalian host. In some embodiments, a host is a non-mammalian host. In some embodiments, a host is an insect. In some embodiments, a host is a bacteria. In some embodiments, a host is *E. coli*.

In some embodiments, a payload-barcode pair is expressed in vitro. In some embodiments, a payload-barcode pair is expressed in vivo. In some embodiments, a payload-barcode pair is expressed from RNA. In some embodiments, a payload-barcode pair is expressed from transcribed RNA. In some embodiments, a payload-barcode pair is expressed from DNA. In some embodiments, a payload-barcode pair is expressed using protein components (e.g. required for protein translation).

After expression of barcoded payload constructs, the constructs may be purified from the pool. In some embodiments, purification may be performed using a universal motif. In some embodiments, purification may be performed using HIS tag, FLAG tag, HALO tag, SNAP tag, Avitag, Twin strep tag, or any other tag based method of protein purification known in the art.

Production of Binders:

Disclosed herein are methods and systems for the production of binders for use in systems and methods of the present disclosure. In some embodiments, binders, as described herein, may be generated rapidly (e.g. in about a week, about 2 weeks, about 3 weeks, about 4 weeks, about 1 month, about 2 months, about 3 months, about 4 months, about 5 months, about 6 months, or about 1 year). In some embodiments, for example, between about 100 to about 1000 binders may be generated rapidly. In some embodiments, between about 10 to about 1000 binders may be generated rapidly. In some embodiments, between about 10 to about 10,000 binders may be generated rapidly. While large numbers of binders, as described herein, may be generated rapidly, such binders are also robust, in that binders generated using the methods disclosed herein may bind specifically and with different affinities to a known set of barcodes.

In some embodiments, a binder nucleic acid library comprises about 1 or more, about 2 or more, about 3 or more, about 4 or more, about 5 or more, about 10 or more, about 50 or more, about 100 or more, about 200 or more, about 300 or more, about 400 or more, about 500 or more, about 600 or more, about 700 or more, about 800 or more, about 900 or more, about 1000 or more, about 2000 or more, about 3000 or more, about 4000 or more, or about 5000 or more potential binders. In some embodiments, a nucleic acid library comprises one or more potential binder sequences. Such potential binder sequences may be screened for functionality as polypeptide binders (i.e. after translation of potential nucleic acid binder sequences) using one or more methods described herein.

Binders in accordance with the present invention may be produced in various ways. In some embodiments, a binder nucleic acid sequence may be inserted into a plasmid to allow for expression in different expression systems. In some embodiments, at least one binder nucleic acid sequence is inserted into a plasmid. In some embodiments, at least two binder nucleic acid sequences are inserted into a plasmid. In some embodiments, at least three binder nucleic acid sequences are inserted into a plasmid. In some embodiments, one or more binder nucleic acid sequences are inserted into a plasmid.

In some embodiments, a binder nucleic acid sequence is attached to one or more genes. In some embodiments, a binder nucleic acid sequence is attached to one or more genes prior to insertion in to a plasmid. In some embodiments, a binder nucleic acid sequence is attached to one or more genes after insertion in to a plasmid. In some embodiments, a binder nucleic acid sequence is attached to a bacteriophage gene. In some embodiments, a binder nucleic acid sequence is attached to an m13 bacteriophage gene. In some embodiments, a binder nucleic acid sequence is attached to gene 3 (i.e. that encodes for gene 3 protein) of m13 bacteriophage.

In some embodiments, plasmids (e.g. containing binder sequences, containing binder and bacteriophage sequences, etc.) may be transformed in to a host. In some embodiments, plasmids may be transformed in to a host and expressed. In some embodiments, plasmids are transformed in to a bacterium. In some embodiments, plasmids are transformed in to *E. coli*.

In some embodiments, expression of plasmids results in phage production. In some embodiments, expression of plasmids results in display of a binder on a surface of a phage. In some embodiments, expression of plasmids results in display of two binders on a surface of a phage. In some embodiments, expression of plasmids results in display of at least one binder on a surface of a phage. In some embodiments, expression of plasmids results in display of one or more binders on a surface of a phage. In some embodiments, expression of plasmids results in display of one or more binders on one or more surfaces of a phage. In some embodiments, expression of plasmids results in display of at least one binder on one or more surfaces of a phage.

Following phage production, the resulting pool may be purified to determine the presence of one or more polypeptide binders. In some embodiments, purification may be performed using a universal motif. In some embodiments, purification may be performed using HIS tag, FLAG tag, HALO tag, SNAP tag, Avitag, Twin strep tag, or any other tag based method of protein purification known in the art.

In some embodiments, a purified binder pool may be highly diverse. In some embodiments, a purified binder pool may not be highly diverse. In some embodiments, a purified binder pool is subjected to screening methods to select binders of interest.

Binders of the present disclosure may be screened for one or more specific properties. In some embodiments, a binder may be screened for specific binding to a barcode. In some embodiments, a binder may be screened for specific binding to one or more barcodes. In some embodiments, a binder may be screened for specific binding to at least a barcode. In some embodiments, a binder may be screened for specific binding to at most a barcode. In some embodiments, a binder may be screened for specific binding to multiple barcodes.

As may be understood by a person of ordinary skill in the art, a binder is designed to be distinct (i.e. unique (e.g. have a unique sequence)) in a pool of binders. Such distinction may be achieved, in some embodiments, by changing one or more amino acids in a binder. In some embodiments, a binder is distinct from other binders in a pool of binders by 1 amino acid. In some embodiments, a binder is distinct from other binder in a pool of binders by at least 1 amino acid. In some embodiments, a binder is distinct from other binder in a pool of binders by at most 1 amino acid. In some embodiments, a binder is distinct from other binder in a pool of binders by 2, 3, 4, 5, 6, 7, 8, 9, 10, 0.1, 12, 13, 14, 15, 16, 17, 18, 19, 20, 21, 22, 23, 24, or 25 amino acids. In some embodiments, a binder is distinct from other binder in a pool of binders by at least 2 amino acids. In some embodiments, a binder is distinct from other binder in a pool of binders by at most 1000 amino acids.

IV. Characterization

Samples:

As described elsewhere in the present disclosure, a sample may be a biological sample. In some embodiments, a sample may contain one or more barcoded payloads. In some embodiments, a sample may contain one or more barcoded proteins.

In some embodiments, a sample is derived from an organism. In some embodiments, a sample is derived from an animal. In some embodiments, a sample is derived from an animal model of disease. In some embodiments, a sample is derived from a non-mammal. In some embodiments, a sample is derived from a mammal (e.g., a rodent, a mouse, a rat, a rabbit, a monkey, a dog, a cat, a sheep, cattle, a primate, and/or a pig). In some embodiments, a sample is derived from a mouse. In some embodiments, a sample is derived from a human. In some embodiments, a sample is derived from cells (e.g. in vitro). In some embodiments, a sample is a human cell line.

In some embodiments, a sample may be purified. In some embodiments, a sample may not be purified.

In some embodiments, a sample is obtained from cells that was treated with barcoded payloads. In some embodiments, a sample is obtained from cells that was not treated with barcoded payloads. In some embodiments, a sample is obtained from an animal that was treated with barcoded payloads. In some embodiments, a sample is obtained from an animal that was not treated with barcoded payloads. For example, in some embodiments, a sample is obtained from a human that was treated with barcoded proteins.

In some embodiments, a sample is obtained from cells that was genetically modified. In some embodiments, a sample is obtained from cells that was modified by gene therapy. In some embodiments, a sample is obtained from cells that was genetically modified to include one or more barcoded payloads. In some embodiments, a sample is obtained from cells that was genetically modified to express a barcoded payloads. In some embodiments, a sample is obtained from cells that was genetically modified to include one or more barcodes. In some embodiments, a sample is obtained from cells that was genetically modified to express a barcodes. In some embodiments, a sample is obtained from cells that was genetically modified to include one or more binders. In some embodiments, a sample is obtained from cells that was genetically modified to express a binders.

In some embodiments, a sample is obtained from an animal that was genetically modified. In some embodiments, a sample is obtained from an animal that was modified by gene therapy. In some embodiments, a sample is obtained from an animal that was genetically modified to include one or more barcoded payloads. In some embodiments, a sample is obtained from an animal that was genetically modified to express a barcoded payloads. In some embodiments, a sample is obtained from an animal that was genetically modified to include one or more barcodes. In some embodiments, a sample is obtained from an animal that was genetically modified to express a barcodes. In some embodiments, a sample is obtained from an animal that was genetically modified to include one or more binders. In some embodiments, a sample is obtained from an animal that was genetically modified to express a binders.

Fingerprints:

Among other things, systems and methods described herein identify the advantages of nucleic acid sequencing techniques and apply them effectively to protein detection and measurement methods. For example, methods described herein may use several binders, with known binding specificities and affinities to different barcodes, that can be expressed on binding agents and mixed together in a single pool. Upon mixing with a pool of barcoded proteins (i.e. proteins, each associated with a barcode as described herein), each binder expressed on a binding agent binds to a one or more barcodes in the pool with known but varying affinities. Such a spectrum of affinities for a given barcode to one or more binders results in a distinct distribution of binder counts for a given barcode that can be determined through NGS, and is termed herein a "Barcode Fingerprint". In some embodiments, the collective barcode fingerprints for a set of barcodes is termed herein a "Fingerprint Matrix". Analogously, a spectrum of affinities of a binder to various (e.g. one or more) barcodes is termed herein as a "Binder Fingerprint". In some embodiments, using the provided technologies the presence of a barcoded protein(s) can be detected, for example, in a complex solution, by extracting and sequencing the associated nucleic acid (e.g. detectable nucleic acid (e.g. DNA sequence, RNA sequence, etc.)) of the population of binding agents (e.g. phage) that bind to the barcoded protein(s). That is, for example, in some embodiments, the presence of a protein in a complex solution is determined not through a single binder, but through a specific combination of multiple binders that bind to a barcode associated with said protein in fixed, known proportions.

Fingerprints, as disclosed herein, have many advantages. In some embodiments, a fingerprint approach of detection allows for reduction of noise. For example, the use of multiple binders to detect a barcode in a complex solution introduces a redundancy into the detection methods that in turn reduces signal noise. Additionally, another advantage of the "fingerprint" approach is that partial non-specificities in the binders (e.g. to barcodes other than the barcode of interest to be detected) can be tolerated and compensated for by the computational prediction methods.

In some embodiments, binder sequences may be modified in order to change a fingerprint. In some embodiments, binder sequences may be modified in order to improve a fingerprint.

A barcode fingerprint, as described herein, for a given barcode may include affinity information of a given barcode to one or more binders. In some embodiments, a barcode fingerprint may include affinity information of a given barcode to one binder. In some embodiments, a barcode fingerprint may include affinity information of a given barcode to at least one binder. In some embodiments, a barcode fingerprint may include affinity information of a given barcode to 2, 3, 4, 5, 10, 20, 25, 50, 100, 200, 300, 400, 500, 600, 700, 800, 900, 1000, 2000, 3000, 4000, 5000, 6000, 7000, 8000, 9000, or 10,000 or more binders. In some embodiments, a barcode fingerprint may include affinity information of a given barcode to at most 10,000 binders.

A binder fingerprint, as described herein, for a given binder may include affinity information of a given binder to one or more barcodes. In some embodiments, a binder fingerprint may include affinity information of a given binder to one barcode. In some embodiments, a binder fingerprint may include affinity information of a given binder to at least one barcode. In some embodiments, a binder fingerprint may include affinity information of a given binder to 2, 3, 4, 5, 10, 20, 25, 50, 100, 200, 300, 400, 500, 600, 700, 800, 900, 1000, 2000, 3000, 4000, 5000, 6000, 7000, 8000, 9000, or 10,000 or more barcodes. In some embodiments, a binder fingerprint may include affinity information of a given binder to at most 10,000 barcodes.

As discussed herein, in some embodiments, multiple barcode fingerprints for a set of barcodes may be grouped together and is termed herein a "Fingerprint Matrix". In some embodiments, a fingerprint matrix may comprise one barcode fingerprint. In some embodiments, a fingerprint matrix may comprise at least one barcode fingerprint. In some embodiments, a fingerprint matrix may comprise 2, 3, 4, 5, 10, 20, 25, 50, 100, 200, 300, 400, 500, 600, 700, 800, 900, 1000, 2000, 3000, 4000, 5000, 6000, 7000, 8000, 9000, or 10,000 or more barcode fingerprints. In some embodiments, a fingerprint matrix may comprise at most 10,000 barcode fingerprints.

The technologies described herein allow for the generation and characterization of unique fingerprints for each barcode. This allows, for example, availability of methods of payload (i.e. target (e.g. protein)) detection that may not require orthogonality between barcode-binder pairs. In some embodiments, barcode-binder pairs may be orthogonal. In some embodiments, barcode-binder pairs may not be orthogonal. As may be evident to a person of ordinary skill in the art, barcode-binder pairs as described herein provide the advantage of being more robust, as the availability of unique fingerprints makes non-specific binding less of a concern, a major advantage in complex environments (e.g. serum, blood, etc.).

Decoding:
Analysis

A key component of the invention is the method used to deduce relative or absolute protein concentrations from the DNA sequencing of binders. In the invention, the DNA sequences are translated in silico into amino acid sequences corresponding to each binder and tabulated to yield a table of binder counts. The binder count table measured for any given barcode in isolation is henceforth known as a "fingerprint" of a barcode. When applying the invention to an unknown mixture of barcoded payloads, the relative or absolute abundance of individual barcodes is determined by comparing the binder count table to the predetermined fingerprints of the individual barcodes and applying a computational prediction method described below. In some embodiments, the binder count table of a mixture of m unknown barcodes is assumed to be a linear combination of their respective fingerprints; the coefficients of the linear combination are inferred through least-squares fitting of the equation $Ax=b$, where A is an n-by-m matrix of fingerprints, b is a length-n vector of binder counts, and x is an undetermined length-m vector of the abundances of each of the barcodes. In some embodiments, the abundances of each of the barcodes is inferred using a Bayesian method, whereby a suitable prior probability distribution over the barcode abundances is assumed, a likelihood ratio of the observed count table given barcode abundances is calculated from a model of the uncertainties in the experimental system, and a posterior probability distribution is inferred the product of the prior with the likelihood ratio. In some embodiments, the posterior distribution is estimated using Monte Carlo sampling methods. In some embodiments, the maximum of the posterior distribution is determined with a computational optimization procedure. In some embodiments, the binder count table is assumed to be a non-linear function of the abundances of various barcodes to account for saturation of particular barcode-binder interactions or competition between distinct barcodes or distinct binders.

In some embodiments, relative proportions of binder counts are compared directly in order to determine relative proportions of barcodes. In some embodiments, sequences of known abundance are mixed into the experiment, and utilized to determine the absolute abundance of a given binder, which is used to estimate an absolute concentration for a barcode.

V. Use

Assessing Payloads:

Technologies described herein may be used to detect, assess, and/or characterize payloads (e.g. proteins). In some embodiments, provided technologies may be used, for example, to assay payloads in complex environments (e.g. serum, blood, tissue, etc.). In some embodiments, payloads may be proteins. In some embodiments, payloads may be therapeutic proteins.

As described herein, a payload may be associated with a barcode (i.e. a barcoded payload). In some embodiments, a barcoded payload may be assayed using binding agents (e.g. phages with binders expressed on them) using methods as described herein. In some embodiments, a barcoded payload may be captured (e.g. using affinity reagents) on a surface (e.g. beads or plates). In some embodiments, a barcoded payload may be immobilized for barcode assaying. In some embodiments, a barcoded payload is contacted with one or more binders and subject to decoding as described herein.

In some embodiments, payloads may be detected, assessed, and/or characterized in vitro. In some embodiments, payloads may be detected, assessed, and/or characterized in vivo.

Kits:

Technologies as described herein may be provided in the form a composition. For example, in some embodiments, a composition may comprise one or more elements (e.g. nucleic acid, amino acid, etc.) to produce or generate one or more barcodes and/or binders as described herein. In some embodiments, a composition may comprise one or more elements to produce or generate a set of barcodes. In some embodiments, a composition may comprise one or more elements to produce or generate a set of binders. In some embodiments, a composition may comprise one or more elements to produce or generate a pool of barcode-binder pairs. In some embodiments, a composition may comprise one or more elements to produce or generate binding agents (e.g. phage expressing binders). In some embodiments, a composition may be a barcode composition. In some embodiments, a composition may be a binder composition. In some embodiments, a composition may be a barcode-binder composition. In some embodiments, a composition may be a binding agent composition. In some embodiments, a composition may comprise one or more of barcodes, binders, binding agents, and/or components thereof. In some embodiments, a composition may comprise one or more sets/pools of barcodes, binders, binding agents, and/or components thereof.

Provided herein are compositions comprising barcodes, binders, binding agents, or components thereof. In some embodiments, a composition comprises barcodes, binders, binding agents, components thereof and/or combinations thereof, which have been assessed, identified, characterized or assayed using methods as described herein. In some embodiments, a composition provided herein comprises one or more, two or more, three or more, four or more, five or more, six or more, seven or more, eight or more, nine or more, or ten or more barcodes, binders, binding agents, components thereof and/or combinations thereof, which have been assessed, identified, characterized or assayed using methods as described herein.

In some embodiments, a composition provided herein comprises two or more, three or more, four or more, five or more, six or more, seven or more, eight or more, nine or more, or ten or more nucleic acid sequences or amino acid sequences as listed in Tables 1 or 2.

A composition as described herein may be formulated in various forms. For example, in some embodiments, a composition as described herein may be formulated in a powder form (e.g. lyophilized). In some embodiments, a composition as described herein may be formulated in a liquid form.

In some embodiments, compositions for use in accordance with the present disclosure are pharmaceutical compositions, e.g., for administration (e.g., topical, oral, subcutaneous, intravenous, intramuscular, intracerebral, intrathecal, rectal (e.g. rectal intubation), opthalmical, intravitreal, or suprachoroidal administration) to a subject (e.g. a mammal (e.g., a human)). In some embodiments, such compositions are administered to a subject to detect, characterize, and/or assess one or more attributes of one or more payloads administered or to be administered to the subject. Pharmaceutical compositions typically include an agent to be administered (e.g., barcodes, binders, binding agents, and/or components thereof), and a pharmaceutically acceptable carrier. Certain exemplary pharmaceutically acceptable carriers include, for instance saline, solvents, dispersion media, coatings, antibacterial and antifungal agents, isotonic and absorption delaying agents, and the like, compatible with pharmaceutical administration. Pharmaceutical compositions are typically formulated to be compatible with its intended route of administration. Examples of routes of administration include topical, oral, subcutaneous, intravenous, intramuscular, intracerebral, intrathecal, rectal, (e.g. rectal intubation), opthalmical, intravitreal, or suprachoroidal administration.

In some embodiments, pharmaceutically compatible binding agents, and/or adjuvant materials can be included as part of a pharmaceutical composition. In some particular embodiments, a pharmaceutical composition can contain, e.g., any one or more of the following inactive ingredients, or compounds of a similar nature: a binder, an excipient, a lubricant, a glidant, or some similar such compound.

Compositions can be included in a kit, container, pack, or dispenser, together with instructions for administration (e.g. to a subject) or for use in a method described herein. In some embodiments, instructions may include methods to reconstitute a powder form composition to a liquid form composition for further use. In some embodiments, a kit may include instructions that allows a user to generate new set of binders for a new set of barcodes. In some embodiments, a kit comprises a set of instructions to perform sequencing of one or more phage particles bound to one or more barcodes.

In some embodiments, a kit comprises information designating peptide barcodes for each binder. In some embodiments, a kit comprises a computer readable program for decoding sequencing data.

In some embodiments, a kit comprises reagents to express a binder on a phage particle. In some embodiments, a kit comprises nucleic acids that encode one or more barcodes. In some embodiments, a kit comprises nucleic acids that encode one or more binders.

Those skilled in the art, reading the present disclosure, will appreciate that, in some embodiments, a composition (e.g., a binder composition, a barcode composition, a binding agent composition, etc.) as described herein may be or comprise one or more cells, tissues, or organisms (e.g., plant or microbe cells, tissues, virus, or organisms) that produce (e.g., have produced, and/or are producing) a relevant binder, barcode, and/or binding agent as described herein.

nose skilled in the art will appreciate that, in some embodiments, technologies for preparing compositions and/ or preparations, and/or for preparing (and particularly for preparing pharmaceutical compositions) may include one or more steps of assessing or characterizing a compound, preparation, or composition, e.g., as part of quality control. In some embodiments, if an assayed material does not meet pre-determined specifications for the relevant assessment, it is discarded. In some embodiments, if such assayed material does meet the pre-determined specifications, then it continues to be processed as described herein.

In some embodiments, a composition is tailored to a specific subject (e.g. a specific mammal, e.g. a patient). In some embodiments, a composition is specific for a payload to be assessed for an individual subject (e.g., mammal (e.g. human, mouse, etc.)). In some embodiments, a composition is specific for payloads to be assessed for an individual subject (e.g., mammal (e.g. human, mouse)). In some embodiments, a composition is specific for payloads of a population of subjects (e.g. mammals (e.g., humans, mice, etc.)). Populations of subjects can include, but are not limited to, families, subjects in the same regional location (e.g., neighborhood, city, state, or country), subjects with the same disease or condition, subjects of a particular age or age range, subjects that consume a particular diet (e.g., food, food source, or caloric intake).

EXEMPLIFICATION

Example 1: Identification of Barcodes, Corresponding Binding Agents, and Determining Fingerprints The present Example demonstrates methods for identifying barcodes, corresponding binding agents (e.g. binders expressed on binding agents), and determining fingerprints (e.g. barcode fingerprints) and using the information to determine the proportion of a barcode in a given mixture. The resulting materials can then be used to measure and quantify different payloads.

Design and Synthesis of a Barcode Library:

Barcode sequences were designed which contain specific sequence motifs thought to fold into a given helical or loop structure. All sequences from the Protein Data Bank (PDB) were downloaded, along with their corresponding secondary structure predictions. Sequences were selected and subsetted from the full sequence if they met the criteria of: being a contiguous helix or loop sequence for a length of 8-25 amino acids. A random subset of 100,000 of the peptide sequences matching this criteria were then ordered as an oligo pool, containing constant overhangs and type IIS sites for cloning into a vector (see FIG. 1B).

Cloning Barcode Library into Expression Plasmid:

The designed pool of barcodes was cloned into a pET expression vector to yield a barcode attached to a payload protein. A plasmid was constructed containing 6×HIS-HALO-TEV-LN-IIS-LC, allowing for direct cloning of the oligo pool via golden gate assembly. LN and LC represent the constant overhangs in the oligo pool used for ligation (FIG. 1B). 1 µg of vector was predigested with BsaI at 37° C. and purified. Oligo pools were amplified via Polymerase Chain Reaction (PCR). A 1:10 molar ratio of purified vector and insert were added to a golden gate assembly reaction using NEB golden gate assembly mix (Cat: E1601S), and incubated at 37° C. for 1 hour, then heat killed at 70° C. for 5 min. This material was then purified, drop dialyzed into pure $H_2O$ for 60 min, and electroporated into electrocompetent BL21 bacteria (lucigen). Serial dilution were plated to recover individual colonies. Colonies were then picked, grown in media containing 1% glycerol and 100 µg/ml carbenicillin, and glycerol stocked in 20% glycerol at −80°

Figure 1B:
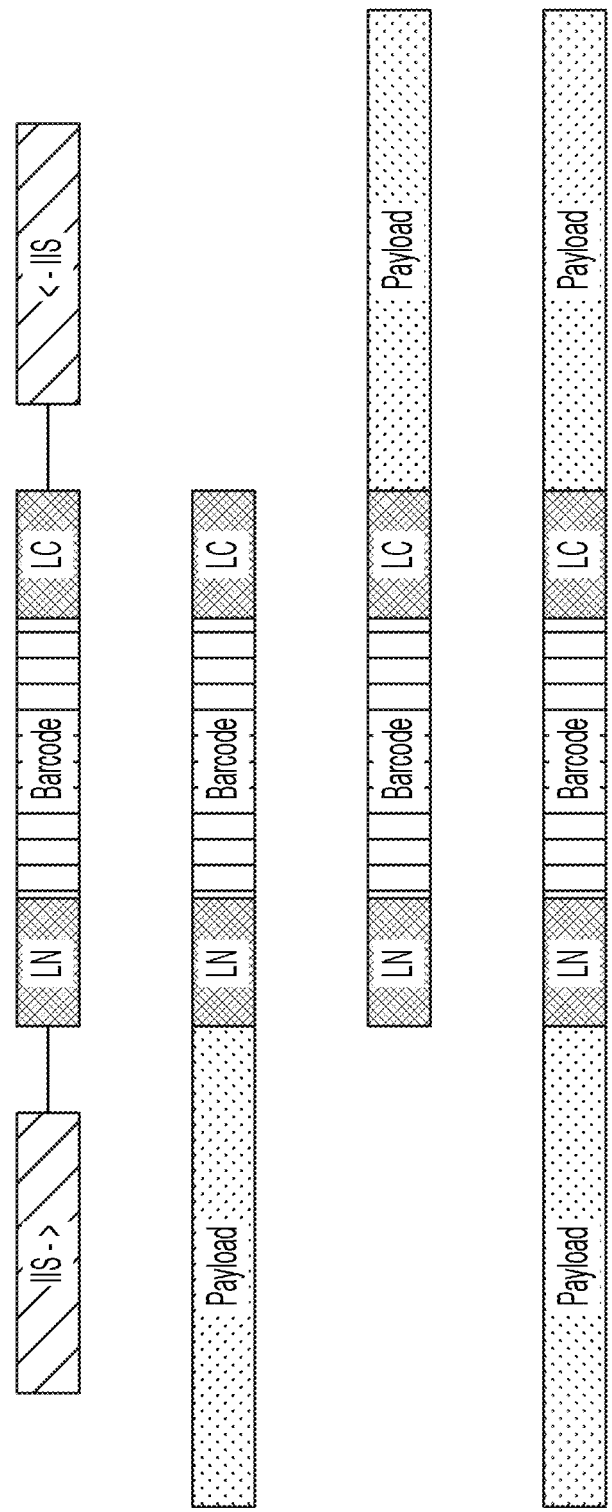
FIG. 1B is a schematic of barcoded payload as described herein, according to an illustrative embodiment. It illustrates a nucleic acid sequence encoding a barcode and/or a barcoded payload. LN refers to "linker N terminus" and LC refers to "linker C terminus". In some embodiments, LN and LC sequences are constant and encode amino acids that connect the payload to the barcode. In some embodiments, LN and LC sequences are constant and are nucleic acid sequences used for modular cloning of barcodes with different payloads. In some embodiments, LN and LC sequences are flanked by Type IIS restriction site sequences.
Figure 2:
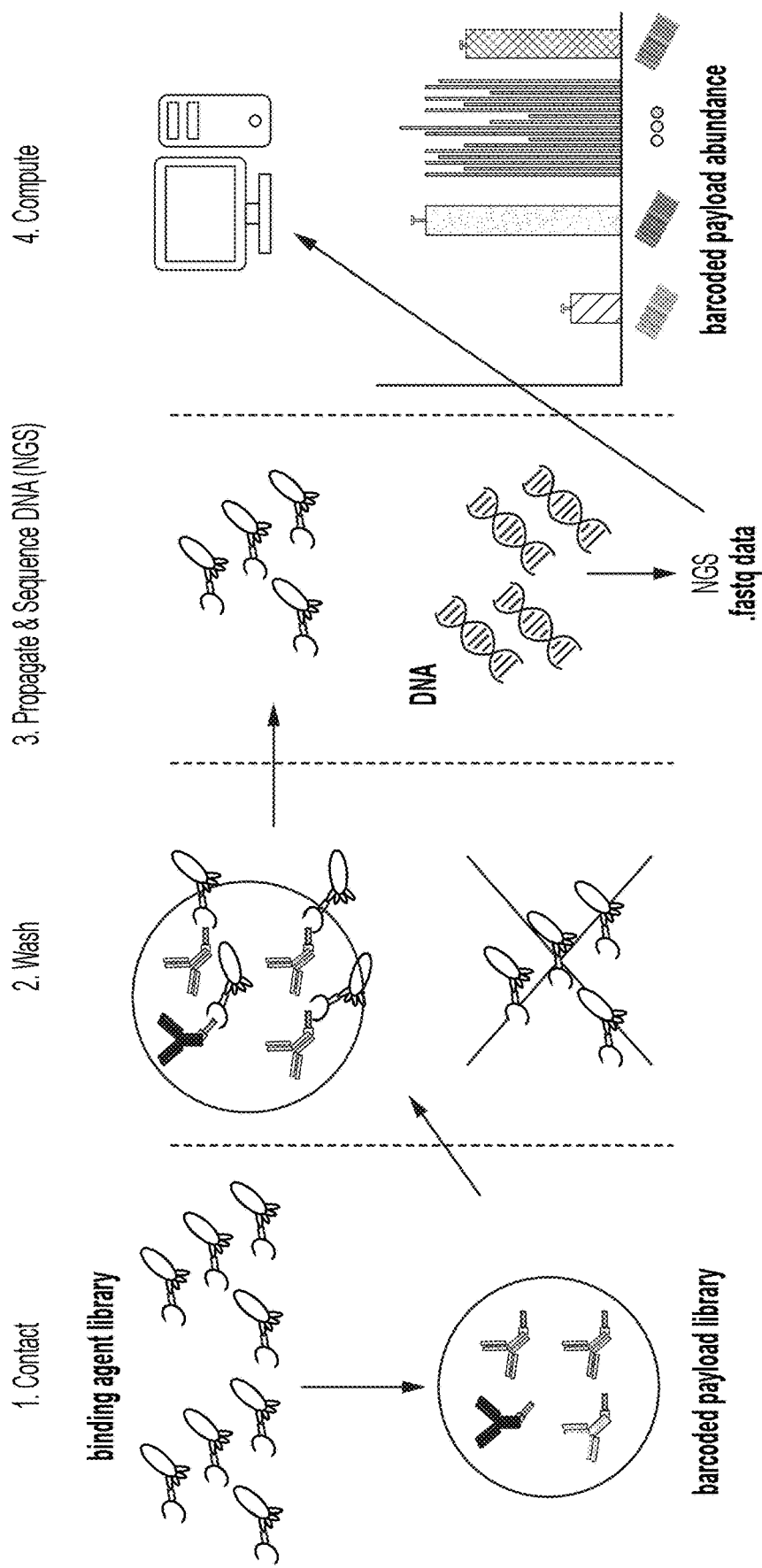
FIG. 2 is a schematic of a method to detect and/or quantify payloads (e.g. proteins) in a pool using barcodes and binding agents as described herein, according to an illustrative embodiment. A library of barcoded payload proteins is contacted with a library of binding agents containing identifying DNA. A wash step is applied that removes binding agents that do not associate (e.g. link (e.g. form strong linkages)) to any of the barcoded payload proteins, while leaving only binding agents that associate with barcodes. Following the wash, a process of DNA sequencing is applied to associated binding agents. In some embodiments, sequencing may be performed using next-generation sequencing (NGS) (e.g. as operated by an Illumina sequencer). The relative abundances of DNA sequences are reported as a computer file (e.g. .fastq data). A computer algorithm is applied on the .fastq data combined with prior biophysical characterization of the binding agents to infer the abundance of each of barcoded payload proteins in a pool.

C. After cloning, a construct is generated containing a barcode attached to a protein using a linker (FIG. 1A).

Expression of Individual Barcodes:

Expression was performed either using in vitro transcription-translation (IVTT) or BL21 induction. For IVTT, PCR was performed directly from glycerol stock by adding primers specific for T7 and T7 terminator sequences in BL21. The resulting amplicon contains T7 and T7 terminator for expression, and makes the protein 8xHIS-HALO-TEV-LN-Barcode-LC. 1 µL of PCR product, containing approximately 50 ng of DNA was added to a 10 µL IVTT reaction using NEBPure (cat no: E6800S) assembled according to the manufacturer's instructions. The reaction was then incubated for 4 hours at 37° C. For *Escherichia coli* (*E. coli*) expression, cultures were grown to an OD of 0.5 at 37° C., then induced using Isopropyl β-d-1-thiogalactopyranoside (IPTG) and grown overnight at 25° C. Cells were lysed the next day using sonication in the lysis buffer, and the lysed material separated from the inclusion bodies via centrifugation, taking the supernatant containing protein. Supernatant was purified using affinity chromatography Ni-NTA resin, and stored for future use.

Figure 3A:
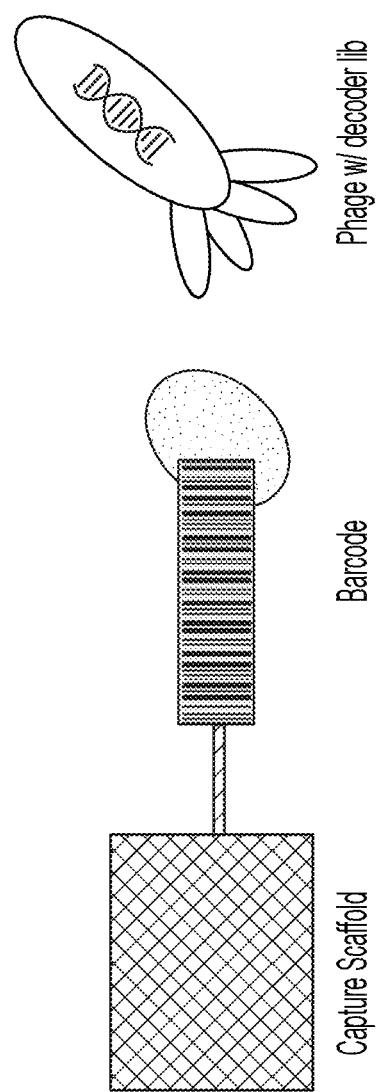
FIG. 3A is a schematic for capturing a barcode as described herein, so that it may be contacted by a binding agent as described herein, according to an illustrative embodiment. It illustrates a capture scaffold that may have a barcode associated with it (e.g. immobilized on its surface), and a binding agent (e.g. phage with binder expressed on its surface (e.g. with binder DNA in phage)) is contacted to characterize biophysical interaction. In some embodiments, the biophysical characterization is a measure of dissociation constant (Kd) between the binding agent and the protein barcode.
Figure 3B:
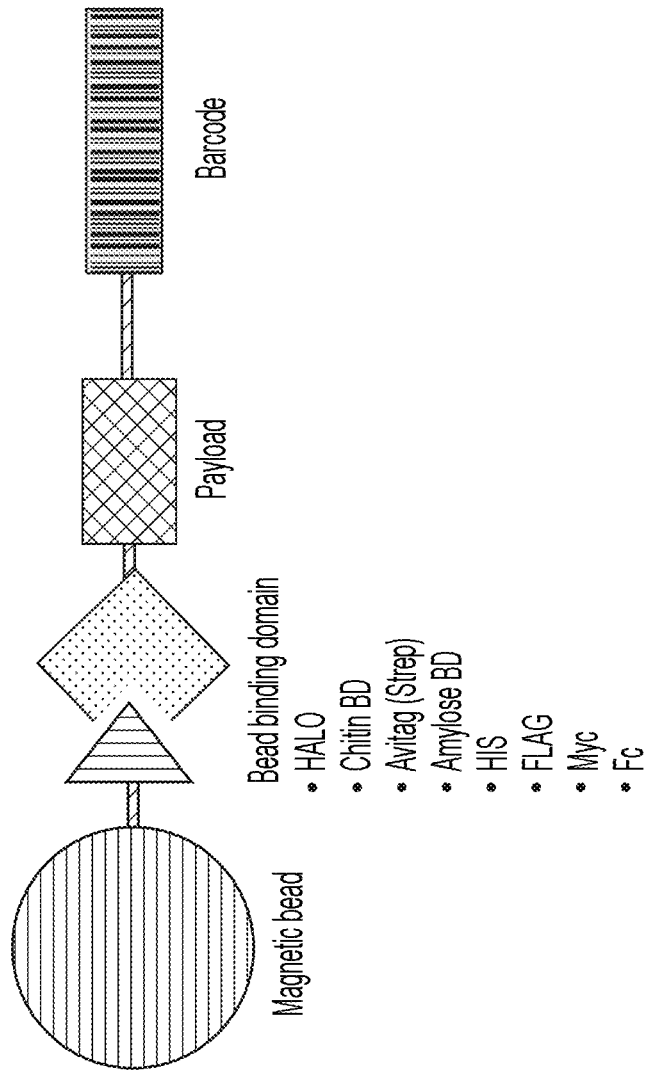
FIG. 3B is a schematic for capturing a barcode as described herein, so that it may be contacted by a binding agent as described herein, according to an illustrative embodiment. It is a schematic of a barcode-binder platform as described herein, according to an illustrative embodiment. The schematic shows a magnetic bead with a bead binding domain conjugated to a universally tagged (e.g. HALO, Chitin BD, Avitag (Strep), etc.) barcoded payload. To detect the captured barcoded payload, a binding agent (e.g. phage expressing a binder on its surface (e.g. phage with binder DNA/lib)) with known affinity to the barcode is bound to the immobilized payload. The DNA within the phage that encodes for the binder is then amplified and subjected to NGS to detect the payload.

Capture of Individual Barcodes on HALO Magnetic Beads:

10 µL of IVTT was diluted to 50 µL in PBS supplemented with BSA at 1 mg/ml. To this mixture, 30 µL of Halo tag magnetic beads (cat: G7281) were added, and incubated with shaking at 400 rpm for 2 hours, then 4° C. with shaking overnight. Beads were captured on magnetic stand, and the supernatant removed. The beads were then washed 2× with PBS-T with 0.1% Tween 20 (PBS-T). A schematic of a captured barcode is shown in FIG. 3B.

Construction of a Phage Display Library Containing Binders with Varying Affinities to Barcodes:

Binders with strong affinities to at least one barcode were generated via methods known to those skilled in the art (e.g. phage display, hybridoma, etc.). These binders were then displayed on phage as scFv fragments fused to m13 gene 3 protein (g3). Briefly, oligos containing the scFv binding sequences were generated via DNA synthesis. The oligo were cloned into a plasmid containing the constant regions of the scFv connected to G3 via a G4S linker (SEQ ID NO.: 8399) and myc tag. 30 µg of the library was electroporated into TG1 (lucigen) and plated on several 25 mm plates containing carbenicillin at 100 µg/ml and glucose 1%. Dilutions of electroporation were plated for diversity analysis. The Q trays were scraped and glycerol stocked. To produce phage, a 2L culture was inoculated at ~OD 0.05 and grown to OD 0.5 at 37° C. with 100 µg/ml carbenicillin and 1% glycerol. At OD 0.5, helper phage was added at a 10:1 phage:cell ratio, and incubated with shaking at 250 rpm. After 1 hour, shaking was reduced to 150 rpm and temperature to 30° C., and incubated overnight. The next day, phage was prepared via PEG precipitation (Barbas et al. 2001), resuspended in 10 mL, and titered. Phage was stored at 4° C. until use.

Figure 3C:
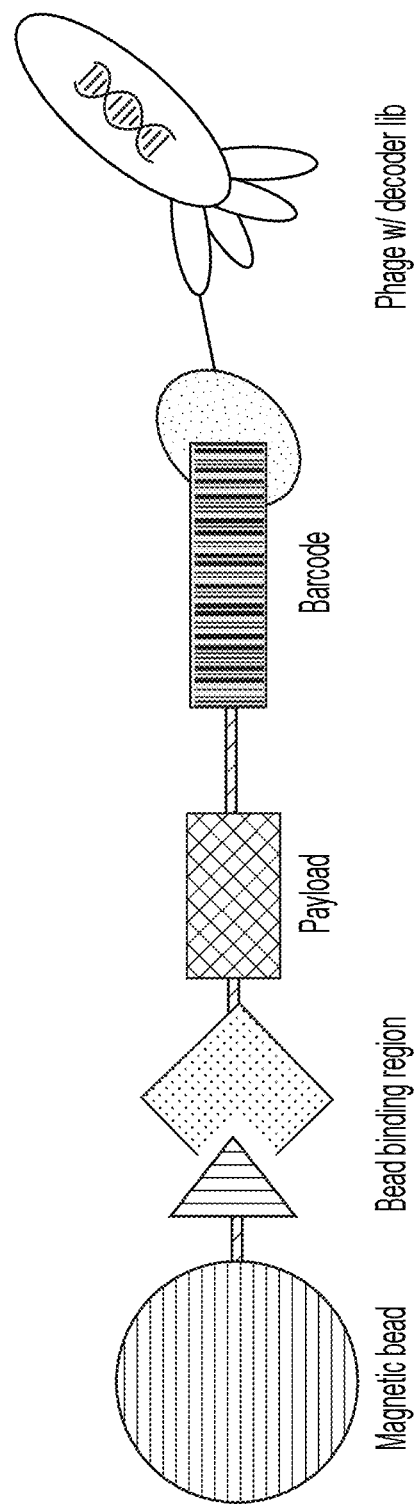
FIG. 3C is a schematic for capturing a barcode as described herein, so that it may be contacted by a binding agent as described herein, according to an illustrative embodiment. It is a schematic of a barcode-binder platform as described herein, according to an illustrative embodiment. The schematic shows a magnetic bead with an Fc/Protein A conjugated barcoded payload. To detect the captured barcoded payload, a binding agent (e.g. phage expressing a binder on its surface (e.g. phage with binder DNA/lib) with known affinity to the barcode is bound to the immobilized payload. The DNA within the phage that encodes for the binder is then amplified and subjected to NGS to detect the payload.

Assessment of Phage-Binder-Barcode Interaction:

10 µL of the phage library prepared using methods described above was added to the captured barcode and incubated at room temperature for 2 hours, to allow binding of the phage to the barcode (FIG. 3C). After incubation, the mixture was washed by successive transfers of the magnetic beads to fresh PBS-T 3 times. Phage were eluted from beads by resuspension in PBS containing TEV protease+0.1% DTT and incubation at 37° C. for 30 min. Beads were collected on a magnetic stand, and the supernatant collected. To the supernatant, trypsin was added and further incubated for 30 min. To propagate phage, the supernatant was added to 50 mL of TG1 *E. coli* grown at 37° C. to an OD of 0.5 in 2×YT and incubated with shaking at 37° C. for 1 hour. Then 100 µg/ml carbenicillin and 1% glucose were added with incubation under the same conditions for 1 hr. Helper phage (cat: PH050L) was added and further incubated for 1 hour at 37° C. The culture was centrifuged and placed into new media containing 100 µg/ml carbenicillin and 50 µg/ml kanamycin, and incubated overnight at 30° C. Following this, centrifugation at 4000 g for 20 minutes was performed, and the supernatant containing phage was collected.

Analysis and Establishment of a Fingerprint for a Given Barcode:

After selection was performed from the original phage pool against each barcode individually, phage-scfv (i.e. phage-binder) selectivity was analyzed via NGS. Phage were lysed via heating at 98° C. for 10 minutes, and the resulting genomes were PCRed using primers which flank the CDR regions of both the heavy CDR3 (5 prime) and light chain CDR3 (3 prime). A second round of PCR was performed to add required illumina sequences (i5/i7, sequencing primer binding region) for NGS. The result DNA was pooled, quantified and subject to NGS using an Illumina instrument. This process is shown in FIG. 2 and FIGS. 3A-3C.

Figure 4:
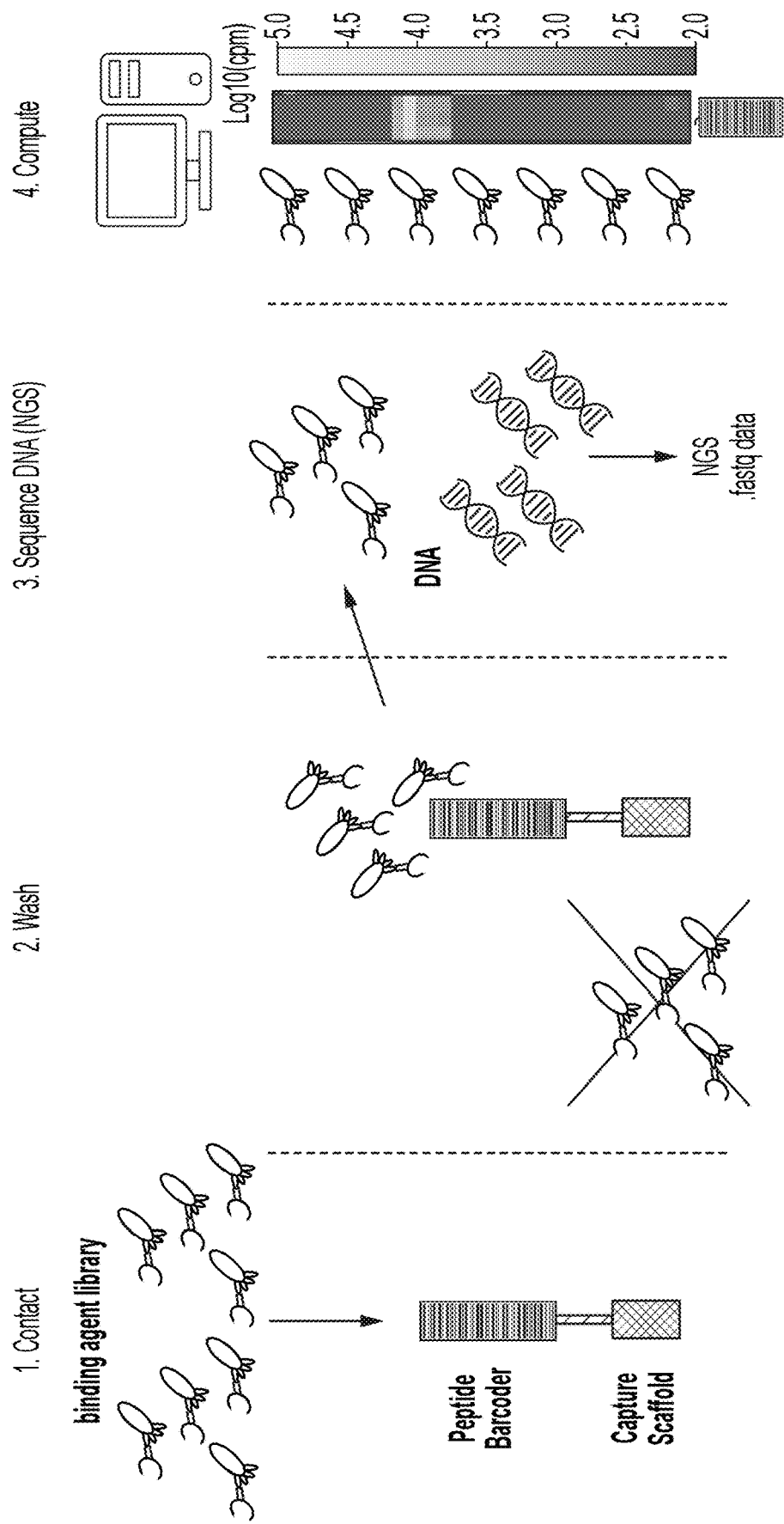
FIG. 4 is a schematic of a method to learn the barcode fingerprint of a given barcode as described herein, according to an illustrative embodiment. A peptide barcode displayed on a capture scaffold is contacted with a library of binding agents containing identifying DNA. A wash step is applied that removes binding agents that do not associate (e.g. link (e.g. form strong linkages)) with any of the barcodes, while leaving only binding agents that do associate with barcodes. After the wash, a process of DNA sequencing is applied to associated binding agents. In some embodiments, sequencing may be performed using next-generation sequencing (NGS) (e.g. as operated by an Illumina sequencer). The relative abundances of DNA sequences are reported as a computer file (e.g. in .fastq format). A computer algorithm is applied on the .fastq data to computer a barcode fingerprint. This is a vector of the relative counts of the members of the binding agent library. The method of learning a barcode fingerprint can be repeated for any barcode to identify a unique fingerprint. In some embodiments, steps 1-4 of FIG. 4 may be repeated, each time starting with a focused binding agent library in order to improve the fingerprint, for a barcode with an existing fingerprint or a new barcode. In some embodiments, the focused binding agent library is made by oligonucleotide library synthesis.

NGS reads are demultiplexed using the illumina software bcl-convert, such that each final .fastq contains the DNA sequences from a given phage CDR3 pair which correspond to the output from a given barcode well. The corresponding CDR3 sequences are then counted using a computer program, revealing the distribution of binders present for a given barcode. The fingerprint of a barcode corresponds to the vector of counts for each scFv binder within the given pool. Each fingerprint is the median of n=3 individual barcode replicates. The process and resulting fingerprint for a single barcode using the pool of phage binders is shown in FIG. 4.

Determination of Proportion of Barcodes in a Given Mixture Using a Fingerprint Matrix:

Once the fingerprints of each barcode of a set of barcodes have been determined, the proportions of barcodes in an unknown sample were measured in the following manner. The binder-barcode interactions were assessed as described above, and the resulting NGS readout was fit to a linear combination of the known fingerprints via least squares. That is, the coefficients of the linear combination are chosen by minimizing the sum of squares of the differences between the measured NGS count and the expected NGS count for all binding species as described in Example 8. The expected NGS count is given by the matrix product of the fingerprint matrix with a set of barcode abundance coefficients. Once the coefficients have been obtained, they are normalized to sum to 1 to obtain proportions.

Figure 5:
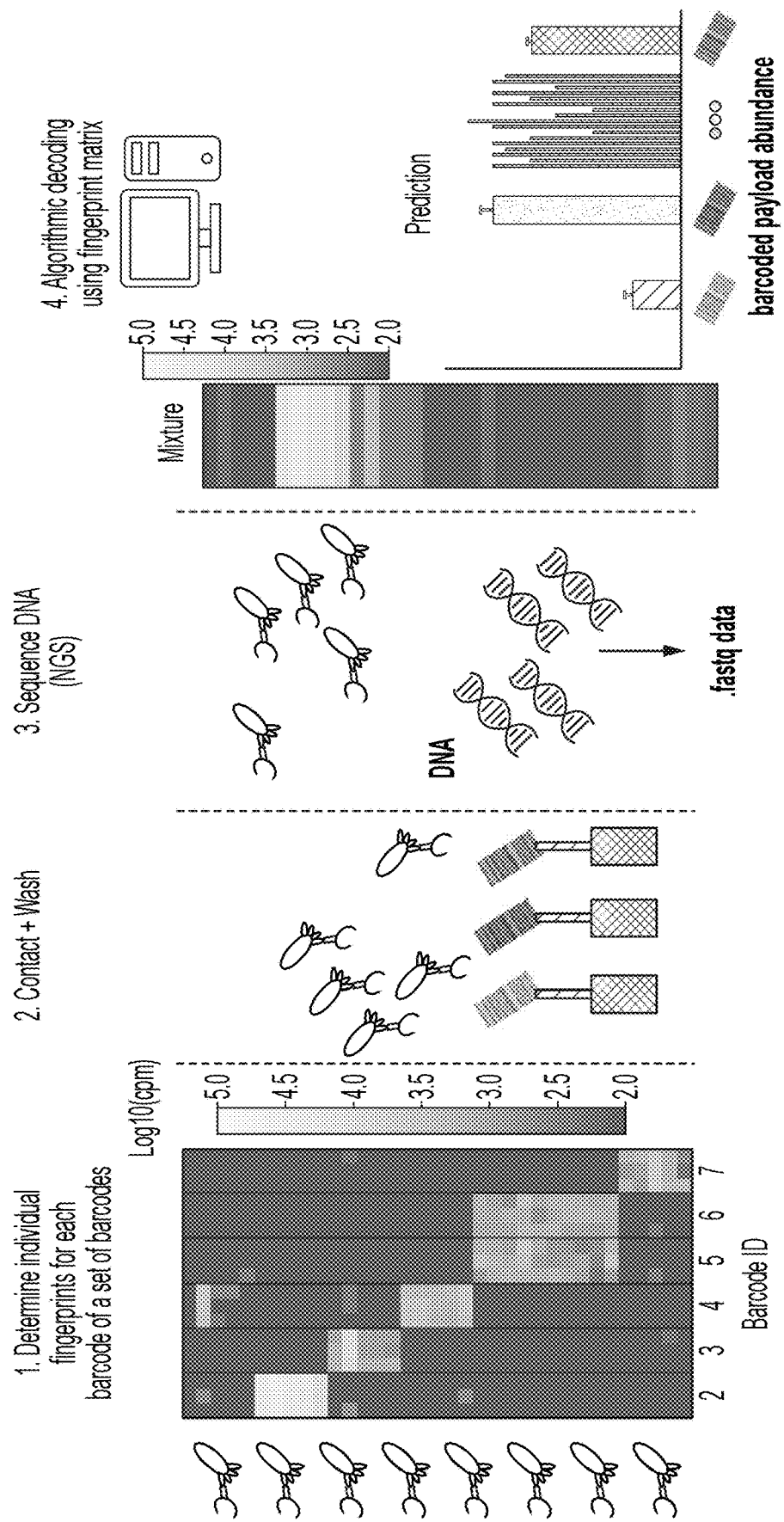
FIG. 5 is a schematic of a method to use a fingerprint matrix of a set of barcodes to determine the relative abundance of a mixture of barcodes, according to an illustrative embodiment. A set of barcodes for which individual fingerprints have been determined are combined together in a known ratio and displayed (e.g. on a scaffold) for subsequent contact with a binding agent library. A binding agent library is contacted with the set of barcodes and non-specific binding agents are washed away. The specific binding agents are quantified by NGS and reported as a mixed measurement computer file (e.g. in .fastq format). This data is provided to a computer algorithm that uses the mixed measurement to learn the relative scalings of readouts relative to the original fingerprints, and assembles the scaled fingerprints together into a scaled matrix. This scaled fingerprint matrix can then be used in further applications of quantifying relative abundance of barcoded payloads using these barcodes in which the computer algorithm is applied to the NGS reads from contacting a sample with a binding agent library.

Decoding of Equal Proportion Barcode Mixture to Asses Fingerprint Scaling:

In order to determine any scaling issues that may arise due to varying affinities between binders and barcodes, a scaling factor is generated via a measurement of barcodes mixed in equal proportions. Briefly, all barcodes validated are mixed at even concentrations after production. Phage binder interactions were assessed as described above, and the resulting phage was subject to NGS. Using the fingerprints determined for individual barcodes above, the proportion of barcodes in the mixture was estimated via least squares regression as described in Example 8. The proportions predicted using the least squares form the basis for scaling factors (sf) where sf=1/p, where p=proportion predicted. The process is described in FIG. 5.

Assessment of Mixtures of Barcodes of Known Proportions:

Barcodes produced above were mixed at known proportions and subject to assessment to determine their accuracy. Barcodes where mixed at different proportions (FIG. 6A), and then analysis of phage binder (i.e. binding agent) interactions was performed as described above. The NGS counts for each binder within the pool were counted. Least squares was used to determine the proportion of barcodes given the fingerprint constructed above using single barcodes. Predictions from the least squares analysis were then rescaled using the established scaling factor by $p'=p*sf$, where p' is the new prediction, p is the original prediction and sf is the established scaling factor. The new predictions are then re-normalized to sum to 1.

Figure 6:
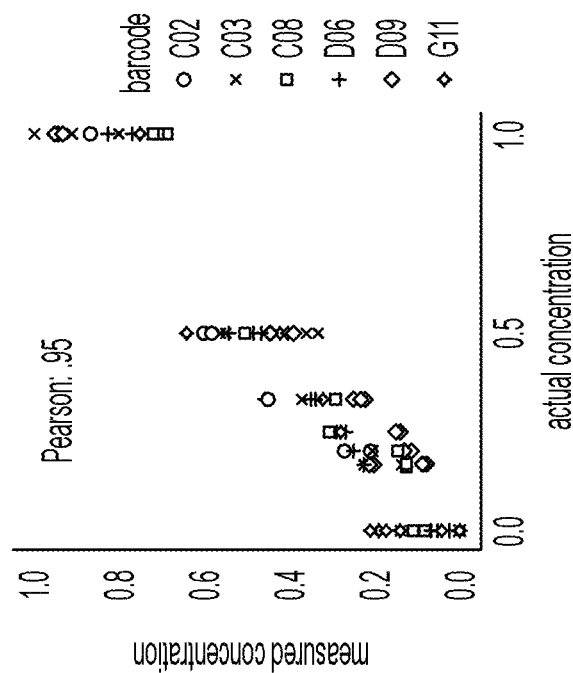
FIG. 6 shows results of quantifying a complex mixture of barcodes. Up to 6 barcodes were pooled and then measured using the decoding method described herein. (A) shows the actual relative proportion of a given barcode (left panel) and the measured relative proportion of a given barcode (right panel). Rows are individual experimental conditions, columns are barcodes, color is measurements (100% barcode=white, 0% barcode=black). (B) shows a plot of measured concentration of barcodes against actual concentration of barcodes for all experiments compared across all barcodes. Across all experiments and mixtures, a pearson of 0.95 between measured and actual proportions was calculated. (C) shows a plot of NGS count values, normalized to counts per million, for each single barcode measurement as well as mixture that were used to predict the relative abundance of each barcode within the mixture. Rows are experiments, thus all values in a row are generated from a single .fastq file and columns are binding agents.
Figure 6:
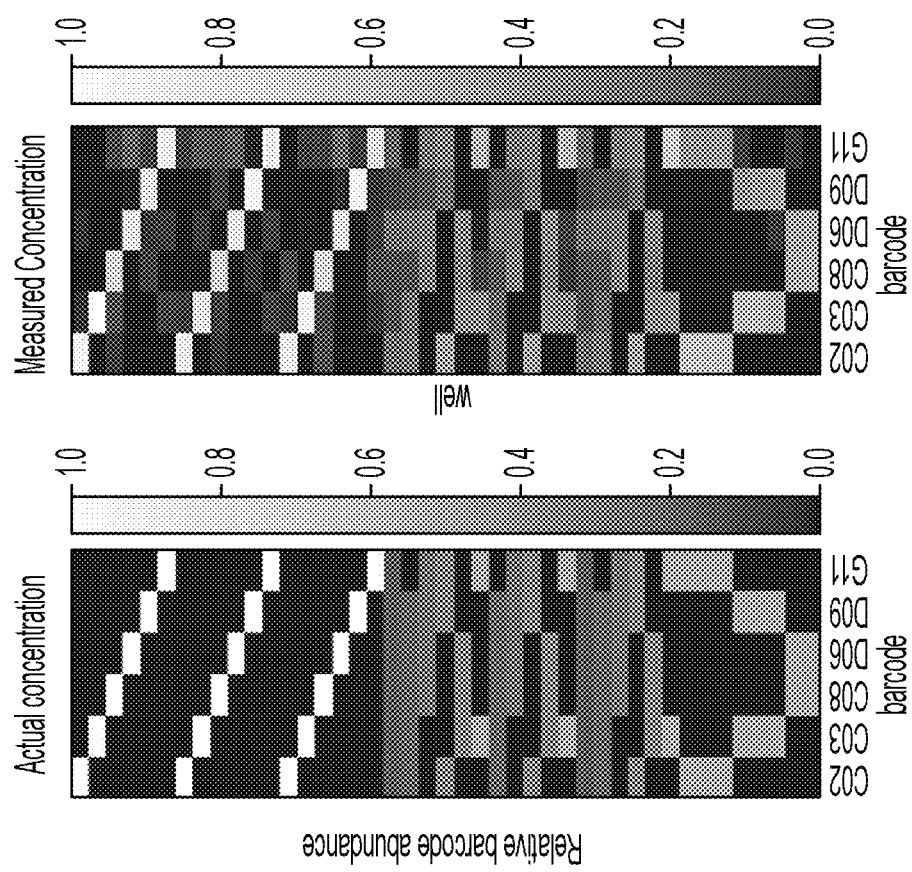
Figure 6C:
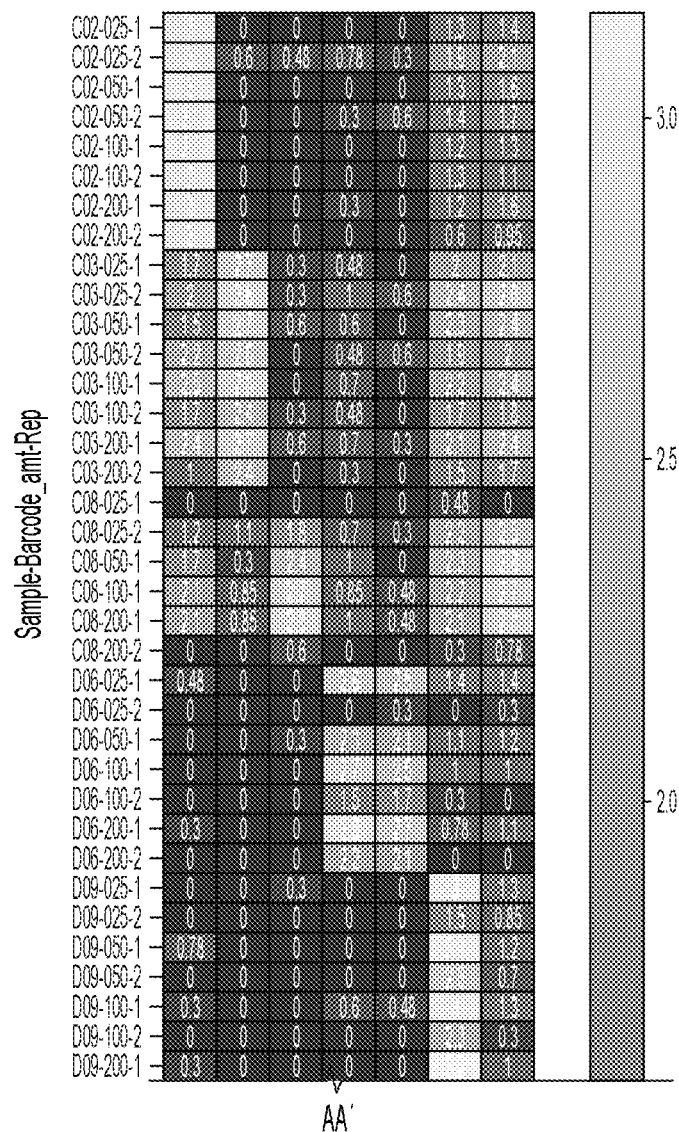
FIG. 6C discloses SEQ ID NOS. 8400-8413, respectively, in order of appearance.
Figure 6C:
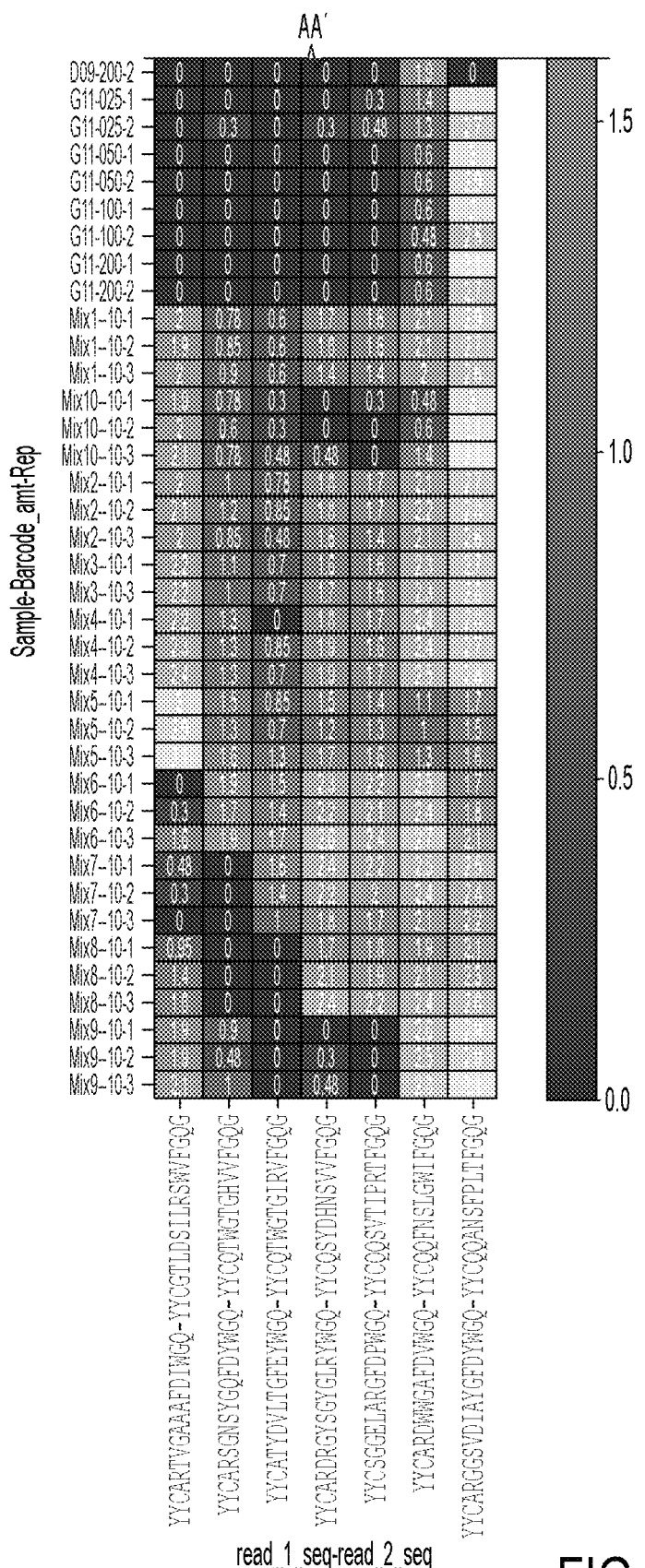

FIG. 6B shows the accuracy of proportion measurement for this method. Six (6) different barcodes were measured, normalized via a scaling factor, and relative barcode proportions were estimated with a global pearson correlation of 0.95 across all measurements made. Measurements were across a 100 fold gradient of barcodes. FIG. 6C shows a plot of NGS count values, normalized to counts per million, for each single barcode measurement as well as mixture that were used to predict the relative abundance of each barcode within the mixture. Rows are experiments, thus all values in a row are generated from a single .fastq file and columns are binding agents.

Example 2: In Vitro Detection of a Payload in a Mixture Using Binder-Barcode Platform The present example demonstrates a method of measuring the presence or absence of a given payload in a mixture using a binder-barcode platform as described herein.

Figure 9:
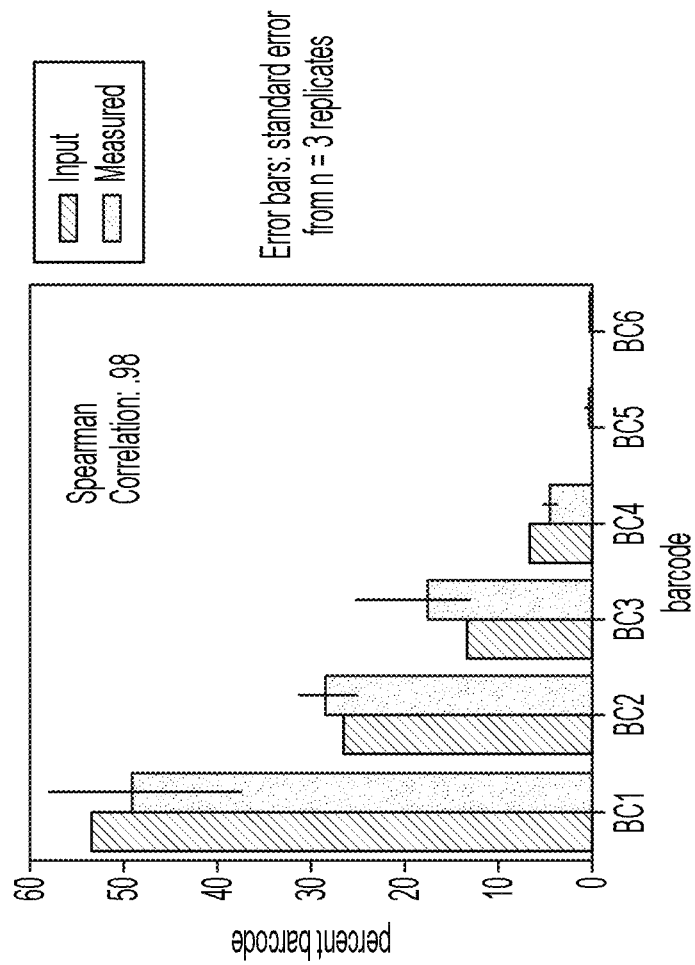
FIG. 9 (A) shows schematic of description of experiment provided in Examples 1, 2, and 8. Six unique barcodes (BC1, BC2, BC3, BC4, BC5, and BC6) were mixed at known proportions, contacted with binding agents, and subjected to decoding as described herein. Two barcodes were experimentally held out as negative controls, but prediction for these barcodes was allowed, thus allowing determination of background prediction. (B) and (C) show data on accuracy of decoding procedure across a 10-fold range of concentrations for the 6 unique barcodes. (B) shows plot of actual data (input) and measured data obtained after decoding for one mixture of known barcode concentrations. Input known concentrations (left bar) are shown next to predictions/measured data (right bar) for each barcode across 3 replicates. (C) shows plots of actual data (input) and measured data obtained after decoding for five different mixtures (i.e. pools 1-5) of known barcode concentrations. Input known concentrations (left bar) are shown next to predictions/measured data (right bar) for each barcode across 3 replicates.
Figure 9:
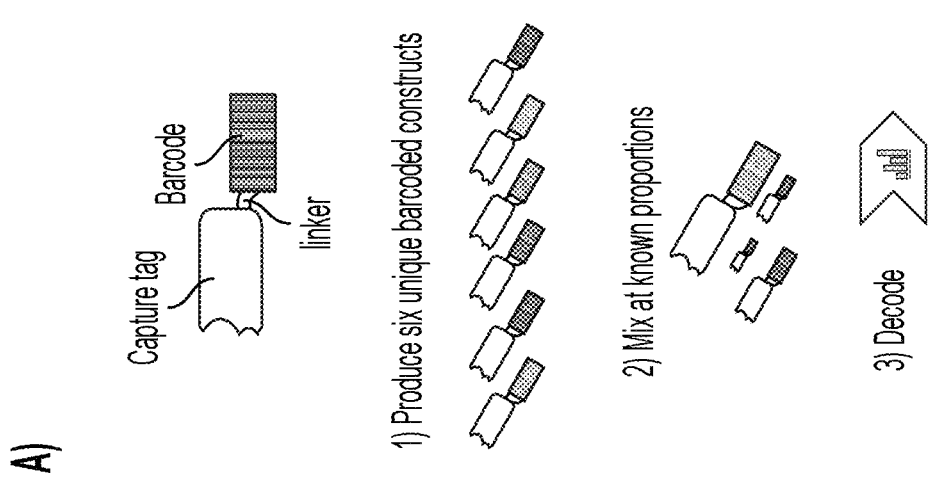
Figure 12:
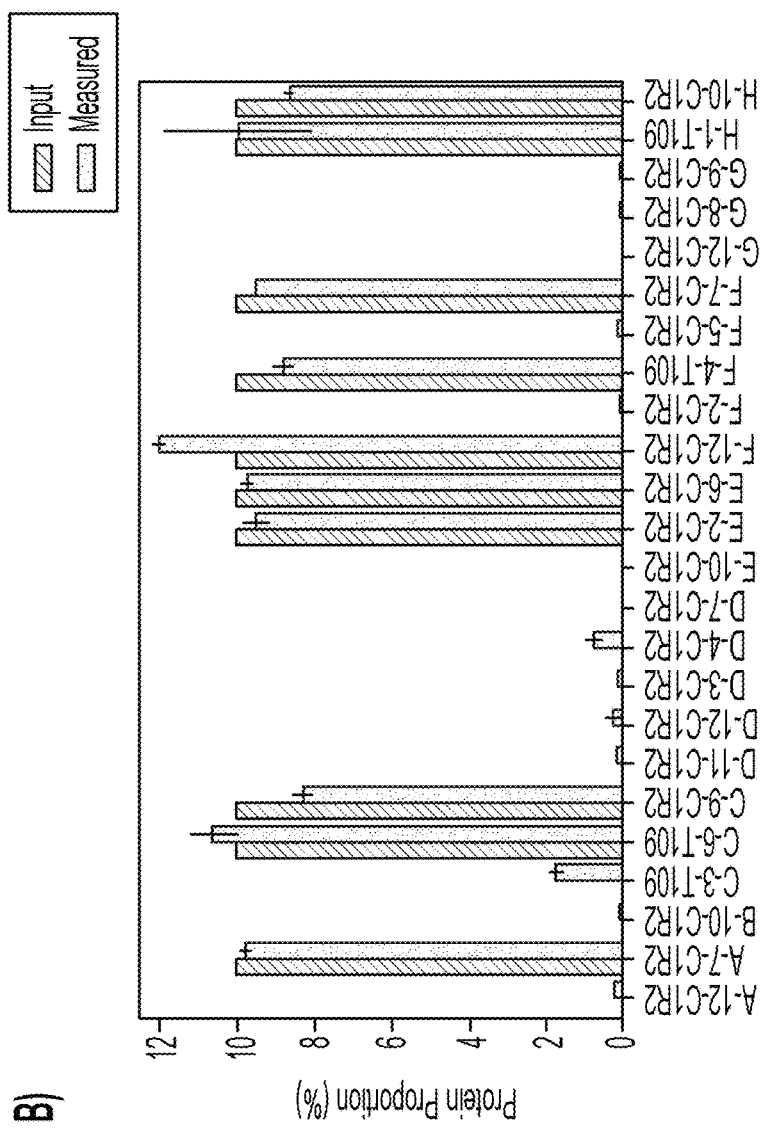
FIG. 12 shows determination of up to 24 barcodes contained within a single mixture. (A) shows a graphical depiction of the experiment. Of 24 total barcodes the algorithm can predict, 10 were present within a mixture at equal concentrations. The rest were held out from the pool, but prediction was computationally allowed. Three (3) separate pools, which cover all possible barcodes were measured in replicate. (B) shows prediction for the first pool. Input concentration (left bar) and measured concentration (right bar) are displayed. (C) shows predictions across all three pools. As in B, input concentration is left bar and measured is right bar. (D) shows the barcode fingerprint for the 24 barcodes used to computationally determine the relative abundance of the barcodes within the 3 pools. Columns represent barcode fingerprints, and rows represent binding agent fingerprints.
Figure 12:
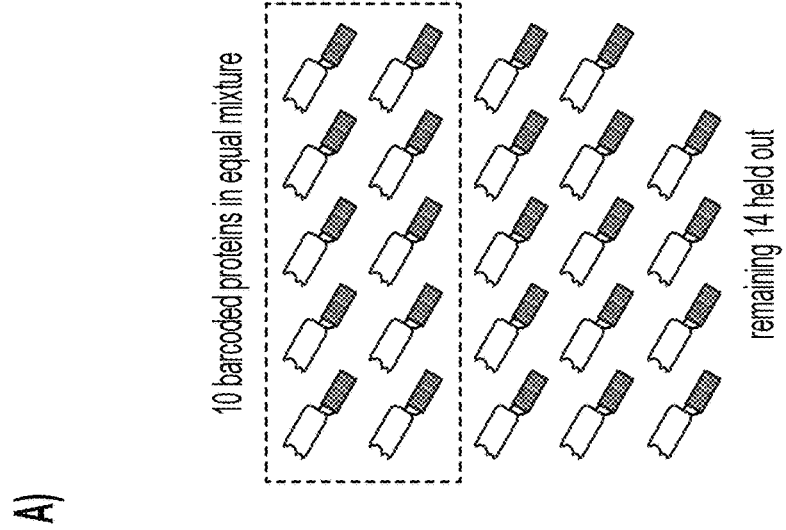

Barcodes generated in Example 1 were transferred onto a novel payload using DNA cloning. Briefly, barcodes were amplified out of the pET 6xHIS-HALO-TEV-LN-Barcode-LC such that the LN-Barcode-LC part is amplified. The barcode insert was cloned using gibson into a new pET vector containing 6xHIS-Payload-LN-Barcode-LC, where payload was a novel protein of interest. Payload-barcodes were produced in *E. coli* as described above. Barcoded payload proteins are then purified via affinity chromatography using Ni NTA, washed in 500 mM NaCl, 50 mM Tris-HCl, 50 mM imidazole, and eluted using 500 mM imidazole. Barcoded payload proteins were then subject to decoding using the phage binder library described in Example 1. FIGS. 6, 9, and 12 show experimental setups to detect payload using barcodes previously generated in a different context, and results of such experiments thus showing these barcodes contain generalized detection properties across varying numbers of barcodes within a pool.

Figure 9C:
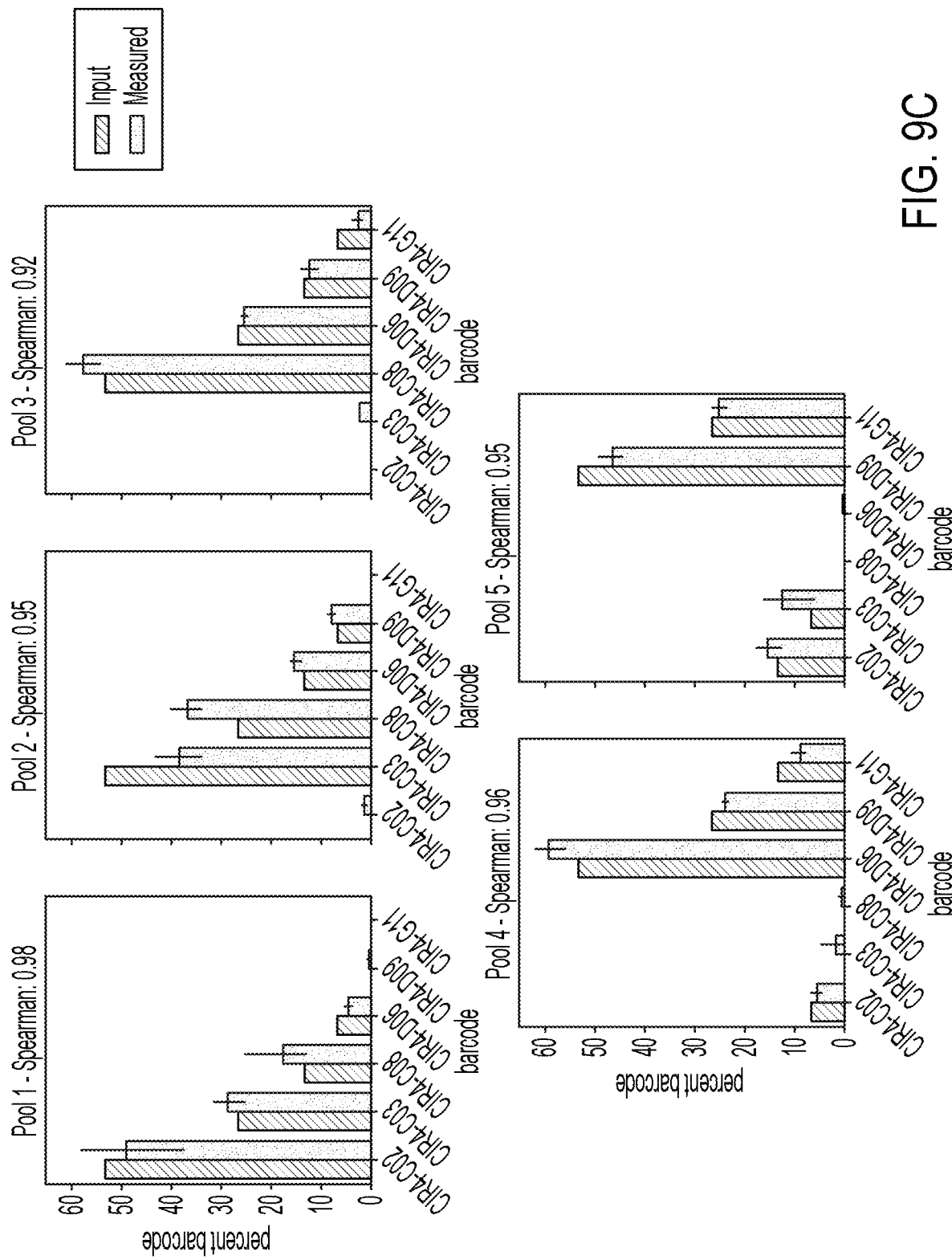

In the experiment described in FIG. 9, six unique barcodes (BC1, BC2, BC3, BC4, BC5, and BC6) were mixed at known proportions, contacted with binding agents, and subjected to decoding as described herein (FIG. 9A). Two barcodes were experimentally held out as negative controls, but prediction for these barcodes was allowed, thus allowing determination of background prediction. FIGS. 9B and 9C show data on accuracy of decoding procedure across a 10-fold range of concentrations for the 6 unique barcodes. FIG. 9B shows plot of actual data (input) and measured data obtained after decoding for one mixture of known barcode concentrations. Input known concentrations (left bar) are shown next to predictions/measured data (right bar) for each barcode across 3 replicates. FIG. 9C shows plots of actual data (input) and measured data obtained after decoding for five different mixtures (i.e. pools 1-5) of known barcode concentrations. Input known concentrations (left bar) are shown next to predictions/measured data (right bar) for each barcode across 3 replicates.

Figure 12C:
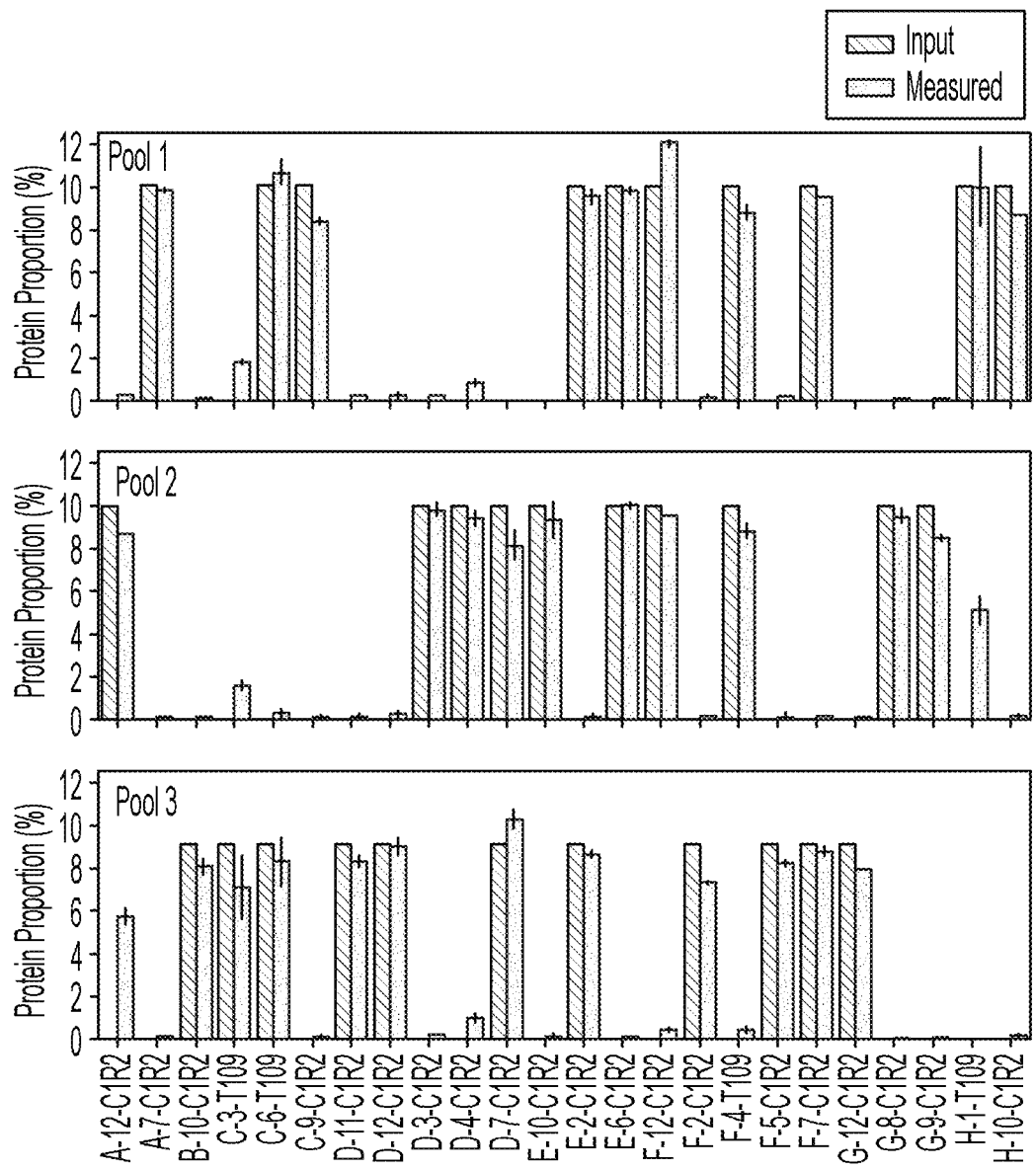
FIG. 12D discloses SEQ ID NOS. 8414, 8415, 8414, 8416, 8414, 8413, 8414, 8417, 8414, 8418, 8414, 8419, 8414, 8420-8425, 8422, 8426, 8427, 8426, 8428-8431, 8430, 8432, 8433, 8432, 8434, 8432, 8435, 8432, 8430, 8432, 8436-8453, 8413, 8453, 8454, 8453, 8455-8475, 8474, 8476-8480, 8479, 8481-8484, 8483, 8484-8493, 8472, 8494, 8472, 8495, 8472, 8496, 8472, 8497, 8472, 8498-8502, 8501, 8503-8505, 8504, 8506, 8504, 8507, 8504, 8508-8516, 8515, 8517, 8518, 8417, 8519, 8520, 8519, 8521-8532, 8403, 8533-8542, 8541, 8543-8545, 8544, 8546, 8544, 8547, 8544, 8548-8552, 8551, 8553, 8551, 8554-8562, respectively, in order of appearance. (E) shows the binding agent counts from the three pools, used to computationally determine the proportion of the pools. Rows are the binding agent counts, columns are the pools, the cell is the binding agent count within a specific pool.
FIG. 12E discloses SEQ ID NOS. 8414, 8415, 8414, 8416, 8414, 8413, 8414, 8417, 8414, 8418, 8414, 8419, 8414, 8420-8425, 8422, 8426, 8427, 8426, 8428-8431, 8430, 8432, 8433, 8432, 8434, 8432, 8435, 8432, 8430, 8432, 8436-8453, 8413, 8453, 8454, 8453, 8455-8475, 8474, 8476-8480, 8479, 8481-8484, 8483, 8484-8493, 8472, 8494, 8472, 8495, 8472, 8496, 8472, 8497, 8472, 8498-8502, 8501, 8503-8505, 8504, 8506, 8504, 8507, 8504, 8508-8516, 8515, 8517, 8518, 8417, 8519, 8520, 8519, 8521-8532, 8403, 8533-8542, 8541, 8543-8545, 8544, 8546, 8544, 8547, 8544, 8548-8552, 8551, 8553, 8551, 8554-8562, respectively, in order of appearance.
Figure 12D:
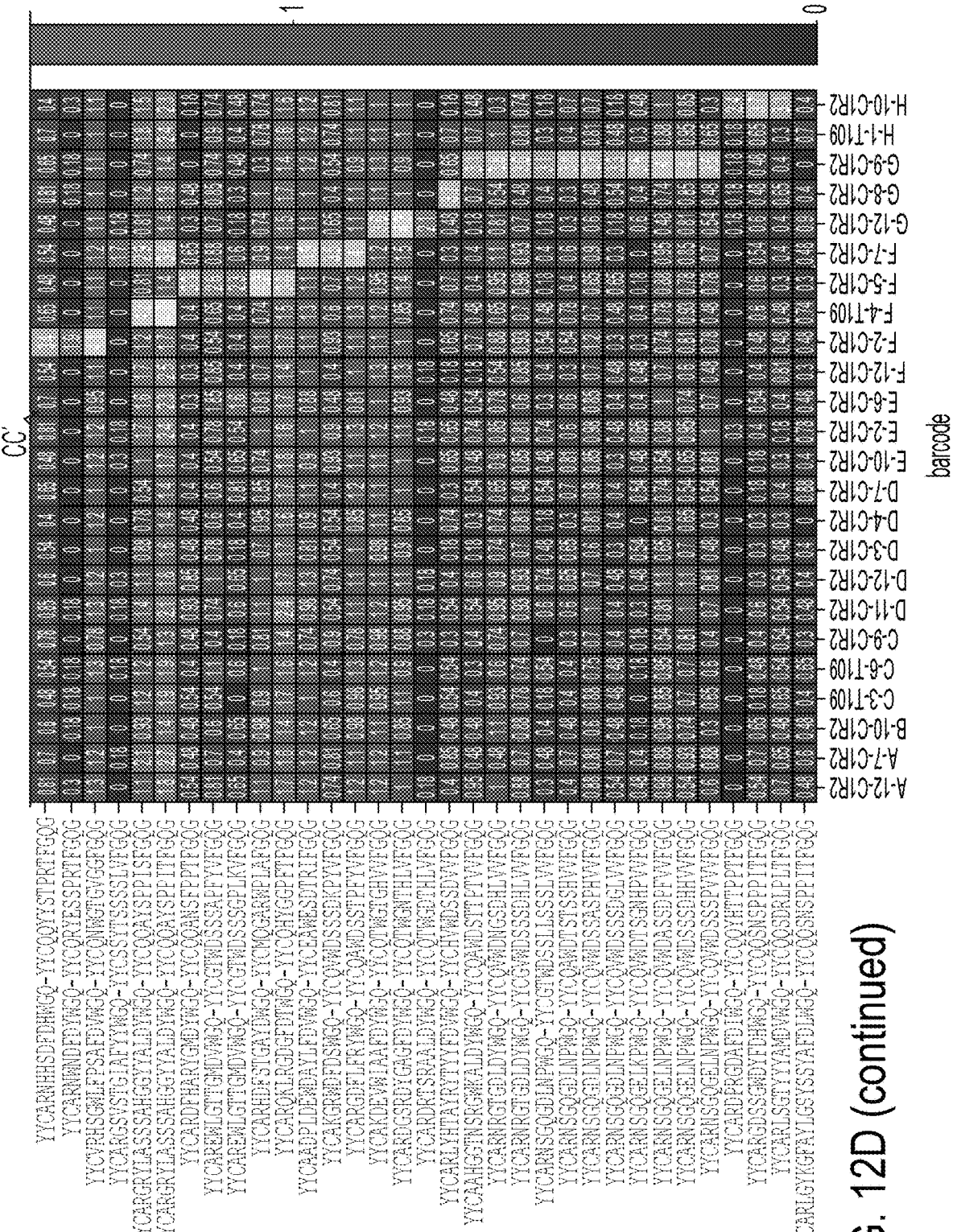
Figure 12E:
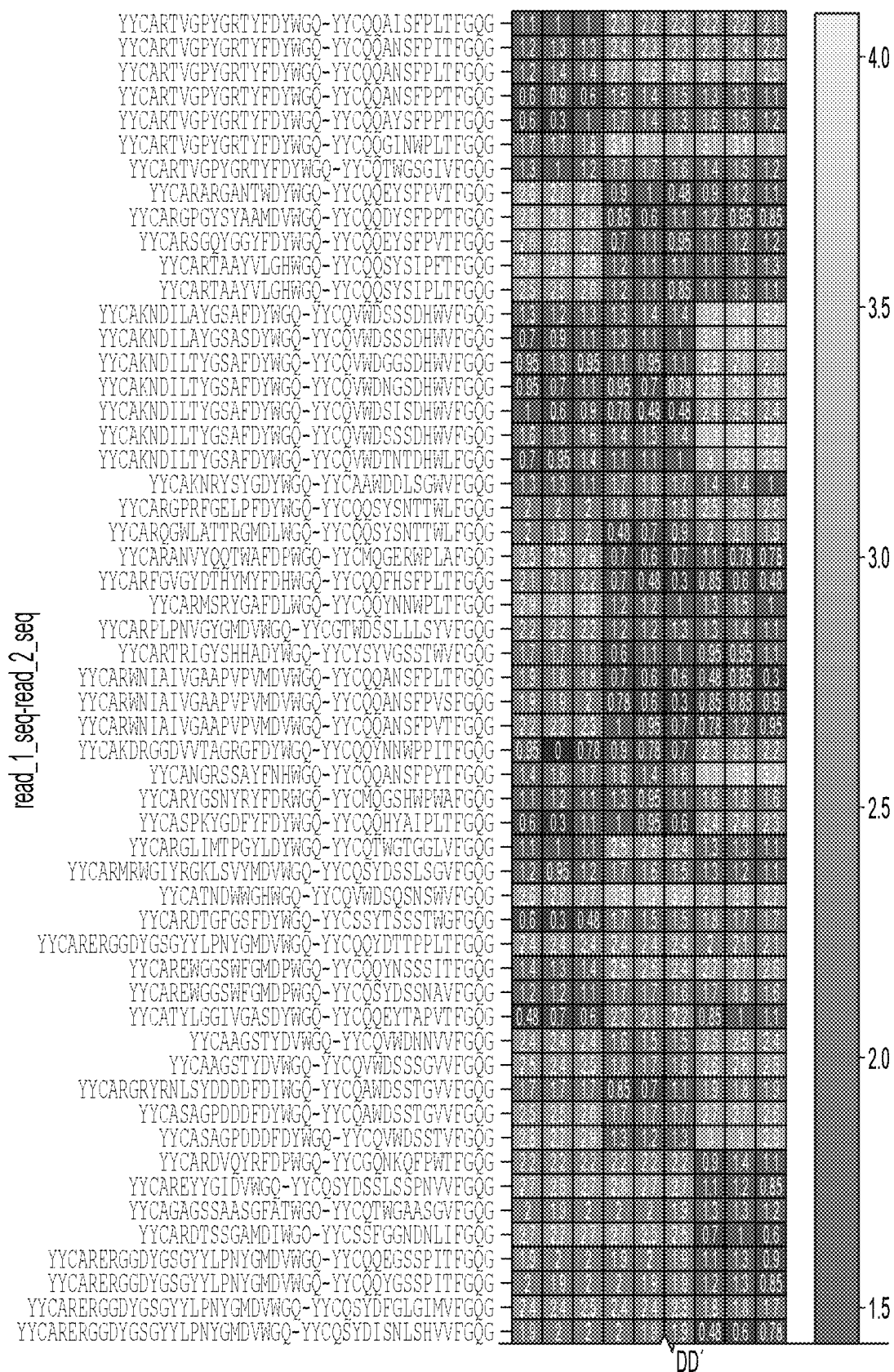
Figure 12E:
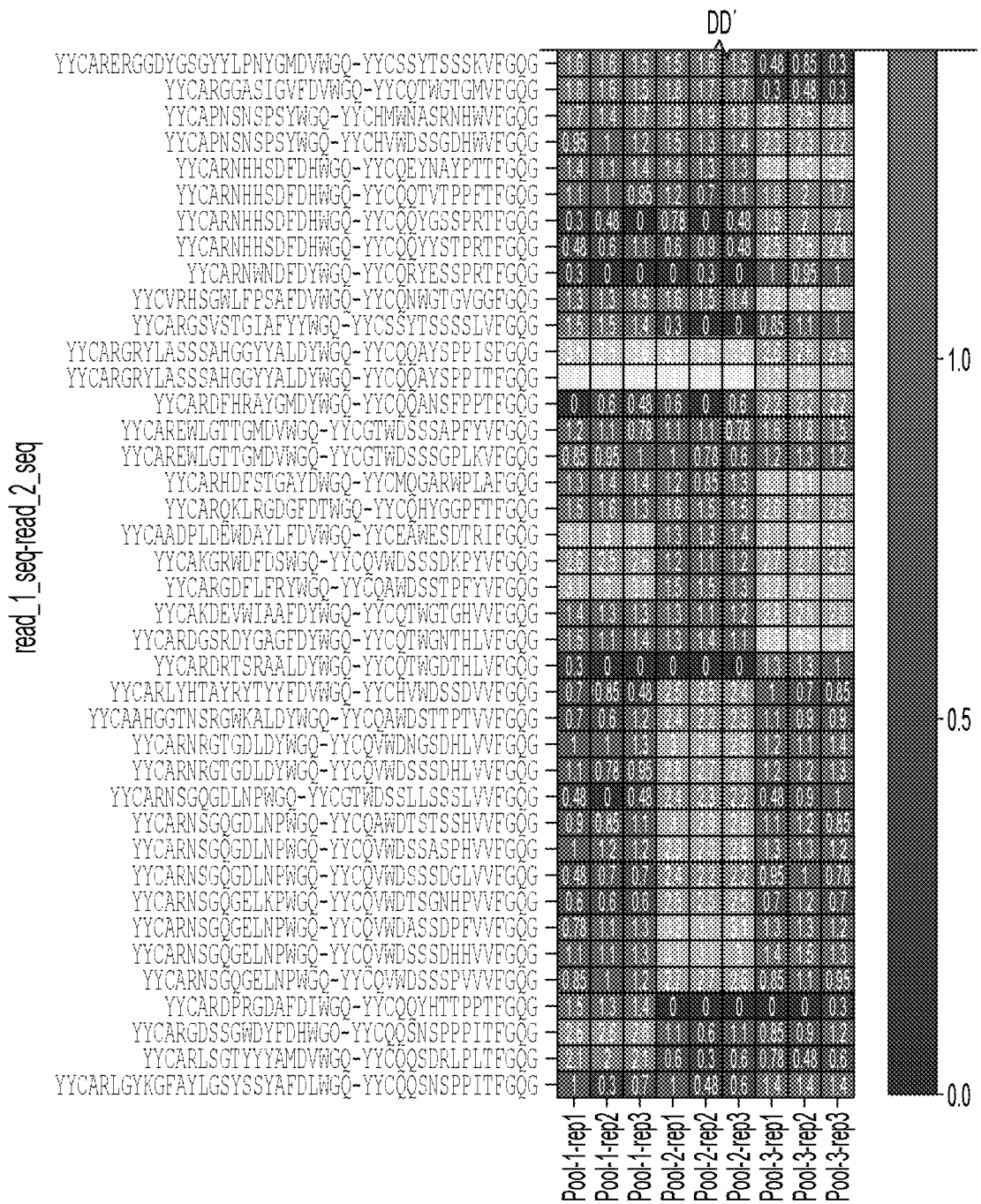

In the experiment described in FIG. 12, the quantification of up to 24 barcodes contained within a single mixture was determined. FIG. 12A shows a graphical depiction of the experiment. Of 24 total barcodes the algorithm can predict, 10 were present within a mixture at equal concentrations. The rest were held out from the pool, but prediction was computationally allowed. Three (3) separate pools, which cover all possible barcodes were measured in replicate. These pools were mixed, then captured on HALO beads, described in Example 1. The immobilized barcoded payload was then contacted with a pool of binding agents (i.e. binding agents with binders expressed on them), and decoded to CDR3 sequence counts as described in Example 1. The CDR3 sequence counts, determined via NGS, were then utilized to determine the presence and total concentration of each barcoded payload in the sample via decoding (see Example 8). FIG. 12B shows prediction for the first pool; the input concentration (left bar) and measured concentration (right bar) are plotted for each barcode in the pool. FIG. 12C plots predictions for each of the three pools. As in FIG. 12B, the bar graphs plot input concentration on the left and measured concentration on the right. FIG. 12D shows the barcode fingerprint for each of the 24 barcodes used to computationally determine the relative abundance of the barcodes within each of the 3 pools. Columns represent barcode fingerprints, and rows represent binding agent fingerprints. FIG. 12E shows the binding agent counts from the three pools, used to computationally determine the proportion of the pools. Rows are the binding agent counts, columns are the pools, and each cell is the binding agent count within a specific pool.

Example 3: In Vitro Assessment of Payload Stability within a Pool of Payloads Using Binder-Barcode Platform The present example demonstrates a method to determine the general aggregative tendencies of several payloads in a pool using barcode decoding.

A purified pool of barcoded payloads is generated using the method described in Example 2. The purified pool is then subject to size exclusion chromatography using standard methods. Different fractions are collected—corresponding to monomeric vs aggregated payloads. The general presence or absence of a given barcoded payload within the purified pool is not known. The separated fractions, containing an unknown abundance of each barcoded payload, are then immobilized on beads or immunosorbent assay plates, contacted with a pool of binders (i.e. binding agents with binders expressed on them), and decoded to CDR3 sequence counts as described in Example 1. The CDR3 sequence counts, determined via NGS, are then utilized to determine the presence and total concentration of barcoded payloads in each fraction. The concentration of barcoded payloads in the different fractions are then compared to determine the percent of each barcoded payload which is monomeric vs aggregated within the purified pool.

Figure 11:
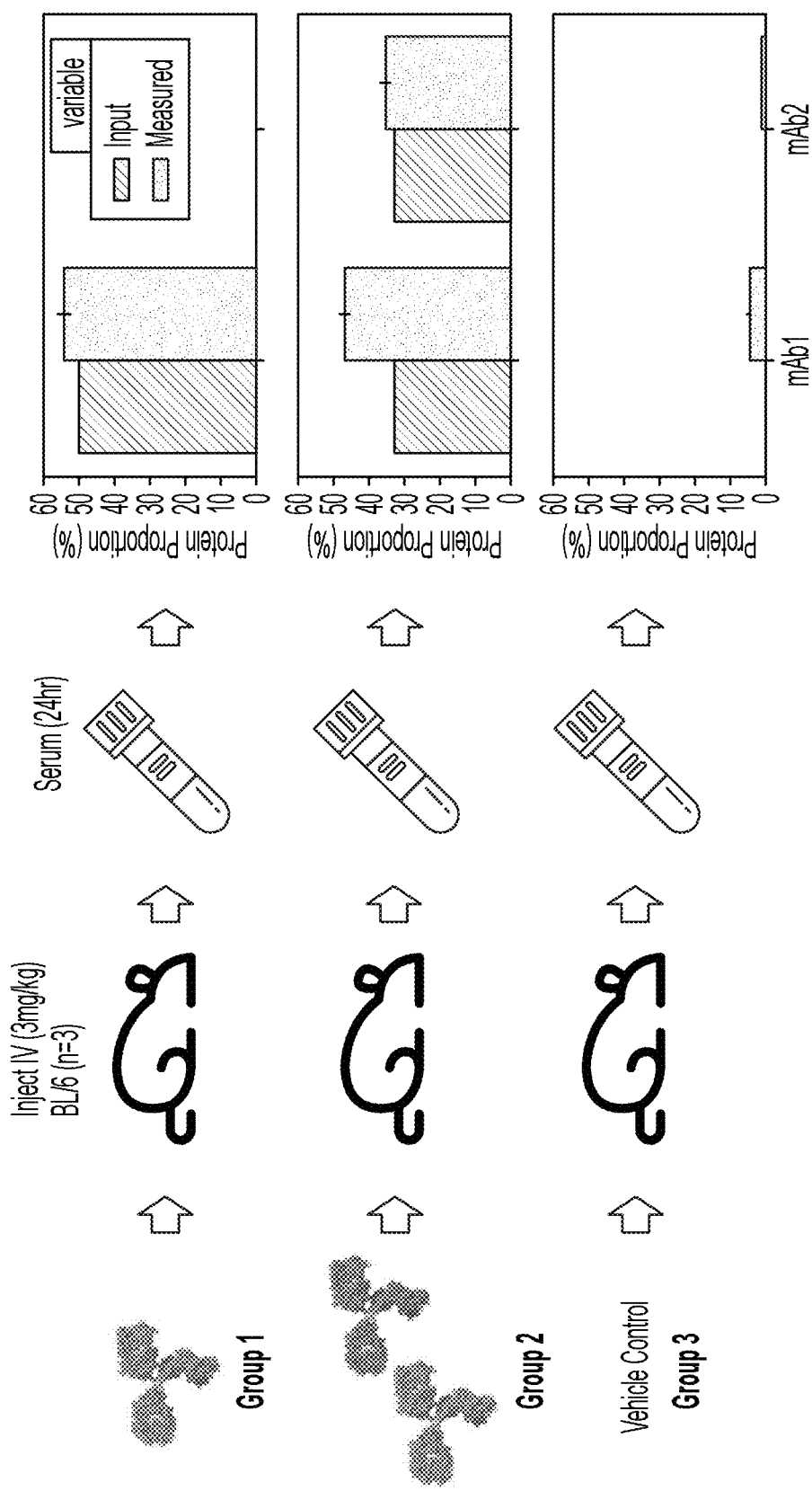
FIG. 11 shows a method for determining the relative abundance of two proteins after injection in vivo, using the binder-barcode system described herein according to an illustrative embodiment. The figure shows a graphical depiction of experimental setup. In group 1 (top), mice were injected with 1 barcoded payload. In group 2 (middle), 2 barcoded payloads were injected. In group 3 (bottom), no barcoded payloads were injected. For each of the three groups, at 24 hours, a serum sample was taken; the barcoded payload(s) captured using binding agents as described herein, and subjected to decoding. The measured barcoded payload concentrations (right bar) compared to known input concentrations (left bar) for each group are shown.

Example 4: In Vivo Assessment of Payload Pharmacokinetics within a Pool of Payloads Using Binder-Barcode Platform The present example demonstrates a method to determine the overall residence and clearance time of a given payload, contained within a pool of payloads, using a mouse model, as demonstrated in FIG. 11.

Three pools of barcoded payloads were injected into three different groups (pool 1 in to group 1; pool 2 in to group 2, and pool 3 in to group 3) of mice (n=3). Pool one contained a single barcoded antibody at 10 mg/kg. Pool two contained two barcoded antibodies pooled at equal concentrations and injected at 20 mg/kg. Pool three contained PBS only. Injection volumes were held constant at 100 μL per pool. At 24 hours after injection, blood was collected from each mouse and serum separated. 10 μL of serum was diluted 1:10 in PBS and captured using anti-human IgG magnetic beads (Ray biotech cat #801-101-1) by incubation overnight at 4° C. with mixing at 700 rpm. The immobilized barcoded payloads were washed using PBS-T three (3×) times, to remove all serum proteins not associated with the affinity reagent. The immobilized barcoded payload was then contacted with a pool of binding agents (i.e. binding agents with binders expressed on them), and decoded to CDR3 sequence counts as described in Example 1. The CDR3 sequence counts, determined via NGS, were then utilized to determine the presence and total concentration of each barcoded payload in the sample via decoding (see Example 8). The proportion of barcoded payloads measured at 24 hours was compared to the injected concentration to determine the relative rate of clearance for each barcoded payload from the organism. In each of the groups, only the injected barcoded antibody was detected by decoding as evidenced by the graph plotted in FIG. 11, with high accuracy. In group 2 mice, which were injected with pool 2 that contains both antibodies at equal concentrations, slightly differing amounts are measured via decoding in the serum at 24 hours. It is hypothesized that this difference is due to differences in clearance rates between the two barcoded antibodies. As expected, the control group showed almost no antibody.

Example 5: In Vivo Assessment of Payload Biodistribution Using Binder-Barcode Platform The present example demonstrates a method to determine the overall distribution of a barcoded payload across a diverse set of tissues using a mouse model.

A pool of purified payloads is injected intravenously into a BALB-6 mouse. After at least 24 hours, different tissue samples, such as liver, lung, and brain, are taken from the organism. The tissues are then processed into a single-cell suspension via vigorous shaking with beads. The suspension is then lysed using a lysis buffer to liberate the barcoded payloads (e.g. barcoded proteins) contained within the tissues. The lysed suspension is then purified using a universal tag affinity reagent contained within the payloads to separate the barcoded payloads. Purified barcoded payloads are then immobilized, and barcode decoding is performed according to method described in Example 1. The CDR3 sequence counts, determined via NGS, are then utilized to determine the presence and total concentration of each barcoded payload in each sample. Payload abundance across different tissue samples is then compared, to determine the percent of each payload which is contained within each tissue. This data may then be used to select the best payload with specific biodistribution properties.

Example 6: In Vitro Demonstration of Recovering Known Mixture of Unmodified Antibodies The present example demonstrates how a known mixture of antibody proteins with no barcode attached was quantified using the protein quantitation invention described herein.

Figure 7:
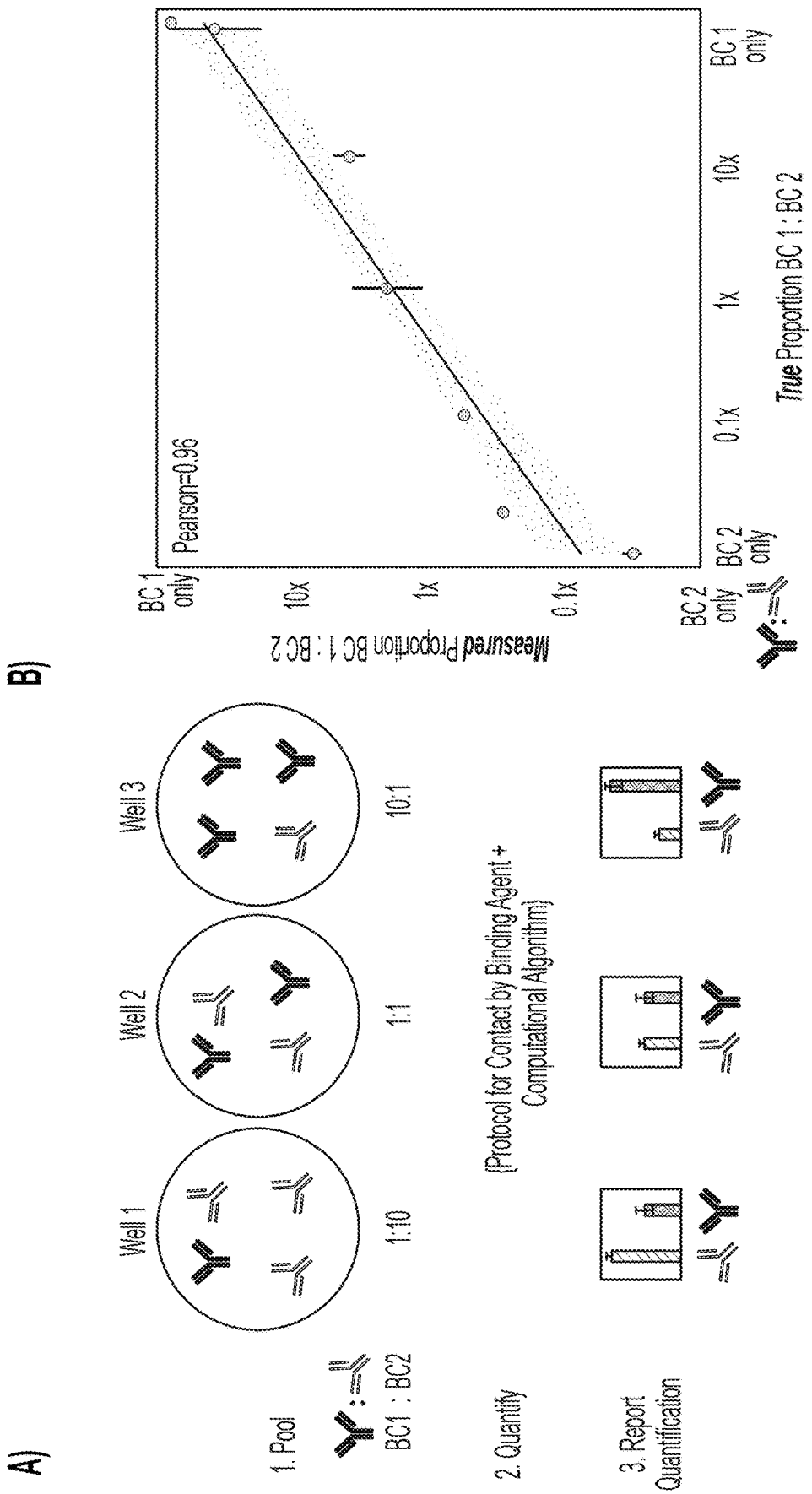
FIG. 7 shows a schematic of a method and data obtained using the decoding method on payload proteins with barcodes contained within internal regions of the protein sequences (i.e. endogenous barcodes). The schematic shows results from a synthetic pooled barcode measurement assay. (A) shows two barcoded payloads (BC1 and BC2) were combined together at various known concentrations in different wells of a 96-well plate. Each mixture was subjected to contact with the same pool of binding agents and decoded as described herein. Each mixture was quantified and then compared to the known values of the barcoded payloads. (B) shows relative actual proportions (X axis) of each barcode correlate to relative measured proportions (Y axis) with a pearson of 0.96

Briefly, scFv binders to the antibodies were generated using methods known to those skilled in the art. The binder were then cloned and displayed on phage as described in Example 1. The two antibodies of interest were expressed in CHO cells and purified from the media using Protein A affinity chromatography. Antibodies were mixed together in known proportions (FIG. 7A). Antibodies were then captured using 50 μL anti-Human Fc magnetic beads and incubated in PBS. The antibodies were then subject to phage assessment as described in Example 1, and the relative abundance of each antibody estimated using the algorithm described in Example 8. An accuracy of pearson 0.96 at determining the relative concentration of these two antibodies in varying proportion mixtures was calculated (FIG. 7B).

Example 7: In Vitro Demonstration of Recovering Known Mixture of Antibodies in Presence of Serum The present example demonstrates how a known mixture of antibody proteins with barcodes contained within internal regions of the protein sequences was quantified in mouse serum using the protein quantitation technology described herein.

Figure 8:
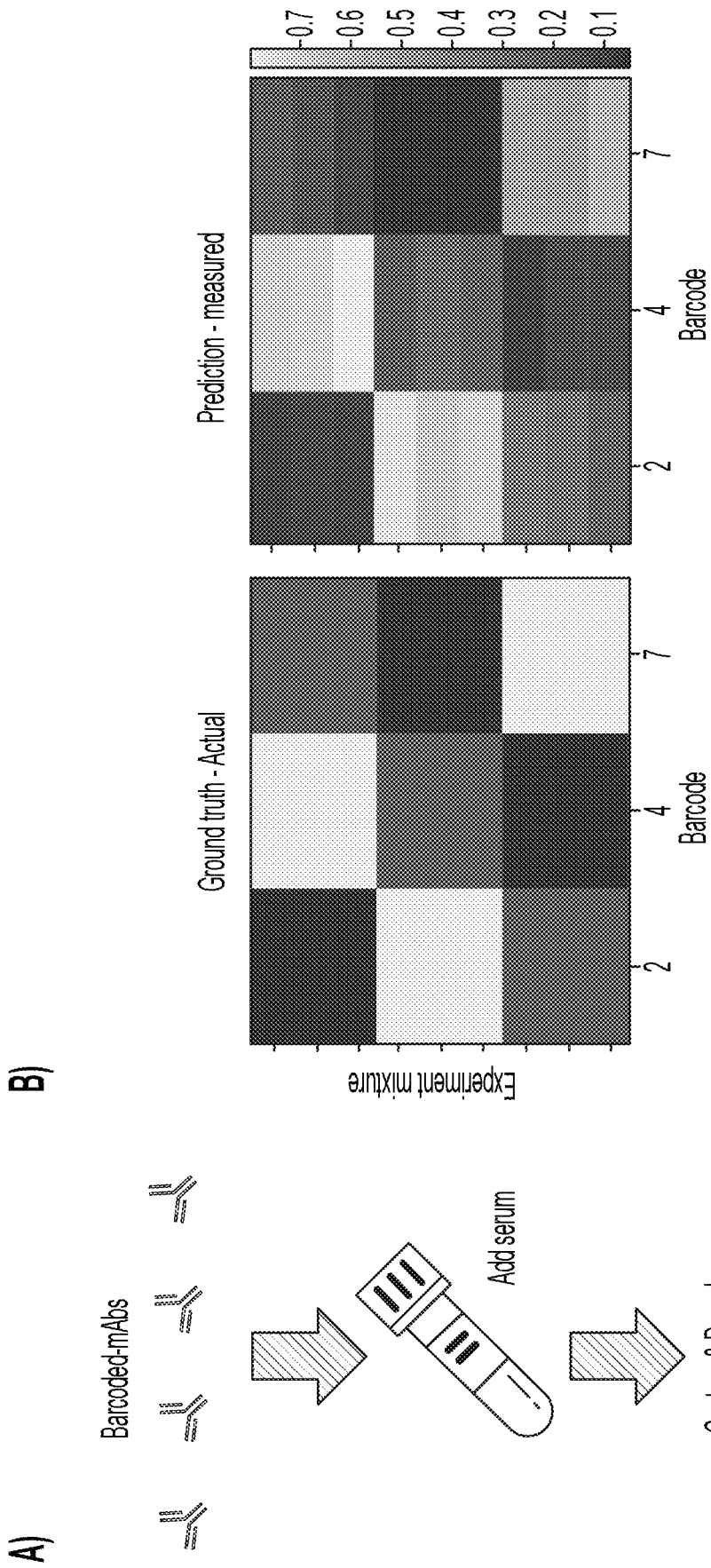
FIG. 8 shows a schematic of a method to detect protein payloads in serum using the barcode-binder platform as described herein, according to an illustrative embodiment. The payload proteins have barcodes contained within internal regions of the protein sequences (i.e. endogenous barcodes). (A) shows the barcoded therapeutic antibody agents of interest (barcoded-mAbs) were mixed at known concentrations and then added to serum. The barcoded payloads were then purified, contacted with binding agents, and subjected to decoding. (B) shows the relative actual barcoded antibody proportion (left) and the relative measured antibody proportion (right) for 3 experimental conditions, with 3 replicates each. Rows correspond to experimental condition, columns to barcodes, and color of heat-map cell is a measure of the proportion of barcoded antibody present. (C) shows a scatterplot of all the data across all experimental conditions for all barcodes with a Spearman correlation of 0.926 across all experimental measurements.
Figure 8C:
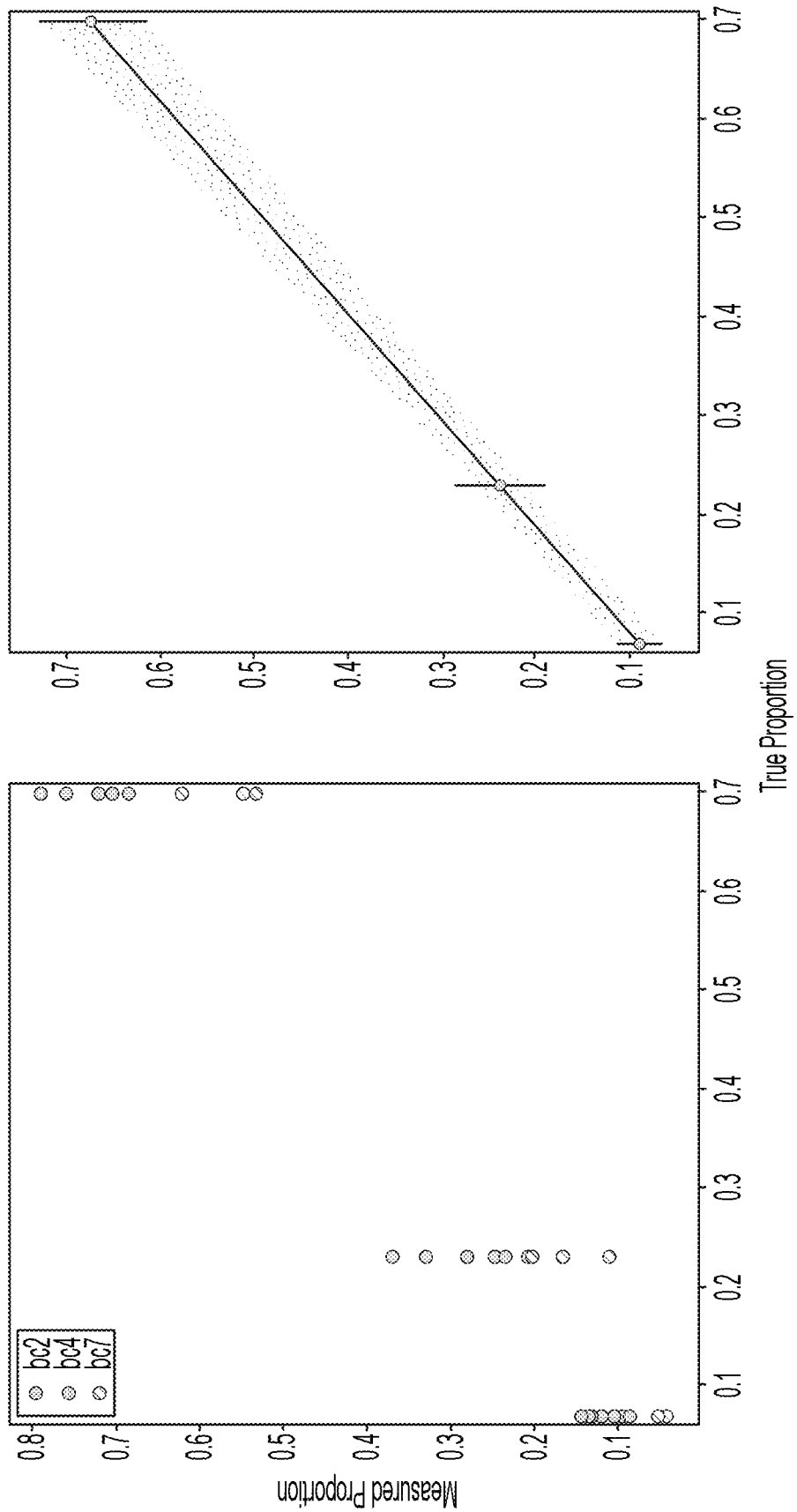

Briefly, antibodies were produced as described in example 6, and a similar experiment was performed, except after production, the antibodies were mixed with mouse serum, incubated at 37° C. for 30 minutes, and then captured using anti-Fc magnetic beads (FIG. 8A). The immobilized barcoded antibodies were then contacted with a pool of binding agents (i.e., binding agents with binders expressed on them), and decoded to CDR3 sequence counts as described in Example 1. The CDR3 sequence counts, determined via NGS, were then utilized to determine the presence and total concentration of each barcoded antibodies in the sample via decoding (Example 8). The relative concentration of three antibodies was estimated with a spearman of 0.926 across 3 mixtures of antibody concentration as shown in FIG. 8B and FIG. 8C. These results show the ability using technologies described herein to rank the antibodies present in a sample with high accuracy after incubation with serum i.e. in a complex environment.

Example 8: Detailed Description of the Decoding Algorithm Used to Infer Barcode Abundance Method of Inferring Barcode Amounts:

Before decoding an unknown sample, a set of barcodes and its interaction with a binder pool (i.e. phage binder pool) must first be characterized. This is done by decoding a set of known samples under known conditions. The binder pool and experimental conditions is held fixed between all samples.

To characterize a set of barcodes, we measure a set of fingerprints, one for each barcode. A fingerprint represents the ideal readout of an individual barcode. Roughly speaking, it is the spectrum of affinities between a given barcode and all the binder species in the pool. A fingerprint can be estimated by decoding multiple identical samples containing purely one barcode, averaging together the readouts of the replicates, and rescaling accordingly. Alternatively, fingerprints can be learned by decoding samples containing known mixtures of barcodes and deconvoluting appropriately to isolate individual fingerprints. Together, the fingerprints of a set of barcodes is known as a "fingerprint matrix".

Once the fingerprint matrix of a set of barcodes is determined, it can be used to infer the barcode composition in an unknown sample. The decoding algorithm accomplishes this by fitting the readout of the unknown sample to a linear combination of fingerprints. This is described in further detail in the algorithmic section described herein. A key assumption of the algorithm is that the decoding process is linear: if a sample contains two barcodes mixed in equal proportions, it is assumed that its readout is equal to the sum of the fingerprints of the two barcodes (plus noise). More generally, the readout of a mixture of barcodes is assumed to be the sum of the fingerprints of each barcode, appropriately weighted by its prevalence in the mixture. This assumption has empirically been found to be true.

The task of barcode quantification has varying levels of difficulty. From easiest to hardest, these include
  Binary classification: detecting the presence or absence of a barcode in a sample
  Rank-order quantification: ranking barcodes from most to least prevalent in a sample
  Relative quantification: determining the ratios between barcodes in a sample
  Absolute quantification: determining the absolute amount of each barcode in a sample
In this Example, absolute quantification is discussed in further detail.

Mathematical Model of Decoding:

The decoding process can be represented with the following mathematical model, where:
x is a length-n vector representing the input sample and each entry is the amount of a barcode species in units of ng; y is a length-m vector representing the bound binder fraction and each entry is the number of particles of a binder species in units of pfu; z is a length-m vector representing the NGS readout and each entry is the number of counts for a binder species.

The bound binder fraction is modelled as a linear combination of fingerprints, and the NGS readout is modelled as multiplying the bound binder fraction by a conversion factor:

$$y_j = \sum_{i=1}^{n} A_{ji} x_i + \epsilon_1$$

$$z_j = s_j y_j + \epsilon_2$$

where $A_{ji}$ is the fingerprint matrix, an m by n matrix with units of pfu bound per ng of barcode. The 'ji' entry represents the propensity for barcode i to bind binder j in the binder pool; $s_j$ is the conversion factor between pfu bound and number of NGS reads for binder species j; $\epsilon_1$ is noise associated with the binding steps; $\epsilon_2$ is noise associated with the post-binding steps.

The model assumes that binding between barcodes and binders is linear. In other words, if a sample contains a mixture of barcodes, its readout is assumed to be equal to the sum of the fingerprints of the individual barcodes, weighted by the relative barcode abundances. In Appendix A we provide a detailed biophysical model which justifies the linear assumption under one key condition: the amount of available binder cannot be significantly depleted by binding to the barcodes in the sample. Thus, as in typical immunoassays, the binding agent must be in excess and cannot be the limiting reagent.

Fingerprint Matrix $A_{ji}$:

Each column of the mn-fingerprint matrix is a fingerprint. Each fingerprint represents the ideal, properly normalized readout of a pure barcode. The entry $A_{ji}$ represents the contribution of the fth binder to the fingerprint of barcode i.

The fingerprint of a barcode depends on the binding affinity to all the binders in the pool as well as the relative abundance of each binder species in the pool. Furthermore, the fingerprint is sensitive to the binding, equilibration, and elution steps. In the simplest case, the fingerprint matrix is given by $$A_{ji} = d_j / K_{ji}$$

where $d_j$ is the concentration of binder j in the binder pool, and $K_{ji}$ is the dissociation constant of the complex between barcode i and binder j (see Appendix A). In more complicated cases, $A_{ji}$ could also include effects of adhesion to surfaces, unbinding during washing steps, etc.

The matrix product of A with a barcode mixture x gives the composition of the ideal bound binder fraction (i.e. in absence of noise), in units of number of phage particles.

The fingerprint matrix can be determined from measuring the readout of multiple known samples. Multiple replicates are performed to average over noise. In addition, the fingerprints are properly scaled, either with respect to one another or to an absolute standard (see the Normalization section).

Conversion Factors $s_j$:

The post-binding steps introduce a conversion factor between the number of bound phage particles to the number of NGS reads. This is represented by $s_j$. In the simplest case, $s_j$ is identical for all binder species and represents an overall normalization, $$s = C \Big/ \sum_{j=1}^{m} y_j$$

such that the total number of reads/counts is C. This models the situation where there is some sort of bottleneck in the processing, such as saturation of the propagation culture, such that the end result is a fixed number of reads, irrespective of the amount of bound phage. In a more complicated case, $s_j$ could depend on the binder species, reflecting amplification bias or differential phage fitness in propagation.

In the case where the conversion factor is identical for all binder species, it is a single number which must be determined on a sample-by-sample basis. This can be done by using a DNA sequence spiked in at some point of the process (as described herein).

Noise $\epsilon$:

Noise sources are represented by the terms $\epsilon_1$ and $\epsilon_2$. In the absolute simplest case, $\epsilon_1$ is absent and is $\epsilon_2$ is Gaussian noise of fixed variance, in which case prediction can be done with ordinary least-squares regression. In reality, the noise arises from multiple, non-Gaussian sources, as detailed in the sections above. These include log-normal noise involved with exponential steps, such as phage propagation and PCR amplification, Poisson noise due to finite sequencing depth (and possibly stochasticity in binding/elution at low concentrations), and Gaussian noise from all sorts of other processes, such as sample degradation, etc.

Conversion from Read Counts to Phage Counts:

One feature of the NGS is that the readout is a relative measurement: it gives the ratio of abundances between different binder species, but not necessarily the absolute concentrations of binder species. To obtain an absolute readout, the raw readout must be divided by a conversion factor between the number of phage particles bound and the NGS read count.

Without knowing the conversion factor, it is only possible to determine the relative abundances of barcode in a sample (i.e. proportions). Absolute quantification requires a reference of known concentration (either barcode or binder) to be spiked into the process.

Methods of Absolute Quantification:

Spiking in a Phage Ladder in Elute:

One method of normalizing is to add a unique binder species into the elute at a known concentration, $y_{spike-in}$. This reference species should be distinct from the existing binders in the pool. In the subsequent steps (where the eluted phage are propagated. DNA extracted, PCR'ed, and sequenced), the reference phage will be amplified by (ideally) the same factor as the other phage in the pool, i.e.

$$z_{spike-in} = s \cdot y_{spike-in}$$

The conversion factor can be estimated by dividing the number of reads corresponding to the reference phage by the (known) concentration at which it was added, i.e.

$$\hat{s} = y_{spike-in} / z_{spike-in}$$

A generalization is to spike multiple binder species into the elute. Each reference species can be spiked in at a different concentration. If the concentrations are evenly spaced, this forms a "phage ladder", in analogy with ladders used in gel electrophoresis. To estimate the conversion factor, the number of reads of each reference sequence can be compared to the (known) concentration at which it was added to the elute. Averaging across the species then yields a more precise estimate of the conversion factor.

Spiking in Barcode into Sample:

Alternatively, a reference barcode of known concentration can be added to the sample at the beginning of the decoding process. This reference barcode should be distinct from the existing barcodes in the sample. The decoding algorithm can use the raw readout to determine the proportions of all barcodes within the sample, including the reference and the sample barcodes. By dividing the reference barcode concentration by its predicted proportion, a barcode conversion factor can be determined. Multiplying all the predicted proportions by this factor then yields the absolute abundances of barcode.

Note that this method is only applicable for decoding an unknown sample after a set of properly normalized fingerprints has been determined.

Scaling Fingerprints:

An important subtlety is that readouts have to be scaled even in the case of relative quantification. Specifically, the fingerprints of a set of barcodes must be properly scaled with respect to one another. Intuitively, this is because raw, unscaled fingerprints cannot be directly compared between barcodes, the read count of a binder has a different meaning in the context of a different barcode's fingerprint, because each barcode has a different conversion factor between bound binder count and read count. To ensure that fingerprints are measured in the same units, each unscaled fingerprint must each be scaled by (the inverse of) its conversion factor.

To illustrate this, consider a case with two barcodes. Suppose that, due to differences in binding affinity across the binder pool, the total amount of binder bound to 100 ng of barcode A is 10 times greater than that bound to 100 ng of barcode B. However, due to the nature of the method, the raw readouts end up having the same number of reads. In this example, one NGS read in barcode A's raw fingerprint corresponds to 10 reads in barcode B's raw fingerprint. The conversion factors are different. Now consider a sample containing a 1:1 mixture of the two barcodes. Due to the difference in affinity, the bound binder fraction in this sample is 10:1; consequently, the number of NGS reads corresponding to A and B would also be in a 10:1 ratio. In other words, the readout is proportional to 10a+b, where a is the raw readout of A and b is the raw readout of B. On the basis of this, one would come to the incorrect conclusion that A and B are in a 10:1 ratio. To correct for this, the raw fingerprint of barcode A must be multiplied by a factor of 10, compared to B, to obtain a correctly scaled fingerprint, a'=10a and b'=b. Now, when the two barcodes are mixed in equal proportions, the correct result is determined: the readout is an equally weighted mixture of the two correctly scaled fingerprints, a'+b'.

This example shows that the relative scaling factor between barcodes' raw fingerprints can be determined by measuring the readout of a known mixture of the barcodes. If the barcodes are mixed in equal proportions, the composition of the mixture readout will be each raw fingerprint, weighted by their scaling relative to each other. (Note that this gives only the relative conversion factor between the barcodes and not an absolute conversion factor to absolute barcode quantities)

The Decodine Algorithm:

There are two phases of the decoding algorithm:
"Training phase": Learn the fingerprint matrix $A_{ji}$ by measuring the readout of a number of known samples
"Testing phase": Predict the barcode amounts in an unknown sample by measuring the readout and comparing it to $A_{ji}$ Training Phase: Learning the Fingerprint Matrix In the training phase, the fingerprints of a set of barcodes are determined by measuring the readouts of a set of samples with known composition. The fingerprints must be correctly scaled with respect to one another. One method of measuring the fingerprint matrix is outlined below.

First, a set of samples, each containing purely a single barcode are prepared. Each sample is decoded. The fingerprint of each barcode is estimated by taking multiple replicates of a barcode and averaging together their readouts. The error is reduced if more replicates are averaged. This yields an unscaled fingerprint for each barcode.

Next, the fingerprints are correctly scaled with respect to each other. This is done by multiplying each of the unscaled fingerprints by a scaling factor. To determine the scaling factor of each barcode, a sample consisting of all barcodes mixed in equal proportion is decoded. Theoretically, this readout of this sample should be the sum of the normalized fingerprints of all the barcodes, weighted equally. However, if we fit this mixture readout to the set of unnormalized fingerprints determined from the previous step, the weights of the barcodes would not be equal. The coefficients to the linear fit are precisely the factor by which each barcode's fingerprint should be multiplied by to obtain a correctly normalized fingerprint. By averaging together multiple replicates of this, a more precise estimate of the scaling factors can be determined.

This method is detailed further below. Let $\tilde{A}$ be the unscaled fingerprint matrix obtained from averaging multiple unscaled measurements of single barcodes. Each column should sum to a fixed number of reads, so the units of $\tilde{A}$ are counts per million. The correctly scaled fingerprint matrix A is obtained by multiplying each column of $\tilde{A}$ by a rescaling factor S, such that $A = \tilde{A}S$, where S is a n×n diagonal "rescaling matrix". Here $S_{ii}$ is the scaling factor for the i'th barcode, with units of pfu eluted per count per million. Let y be the readout of a mixture of known composition x. One way to determine scaling factors is to use the unscaled fingerprint matrix to infer a set of "biased" predictions as $\tilde{x}=\tilde{A}+y=SA^+y$, where $\tilde{A}^+$ is the pseudoinverse of $\tilde{A}$ (see the prediction section below). The ratio of the "biased" prediction to the actual amount is an estimate of the scaling factor: $S_{ii} \approx \tilde{x}_i/x_i$. Multiplying each unscaled fingerprint by this scaling factor gives our best estimate of the properly scaled fingerprint $A=\tilde{A}S$.

Note that there are other methods for measuring the fingerprint matrix. This present method only uses the single-barcode samples to determine (unnormalized) fingerprints, and the mixture samples to determine the scaling factors. More sophisticated methods may use uneven mixtures to determine scaling factors and/or use the information in these samples to better estimate the fingerprint (beyond just learning its scaling factor).

Testing Phase: Predicting Barcode Amounts in Unknown Samples

In the testing phase we are supplied with the readout y of an unknown sample x and we aim to infer its composition, $\hat{x}$. This is done by fitting the readout to a linear combination of fingerprints, $y=A\hat{x}$, where A is the (properly scaled) fingerprint matrix learned from the training phase.

The fitting is done by choosing a set of coefficients $x_j$, which minimizes a loss function. The loss function measures the deviation between the expected and measured readout. The expected readout is the matrix product $A_x$, based on the determined fingerprints and proposed mixture coefficients. In the simplest case, the loss function is a sum of squared errors, $$\mathcal{L}(\hat{x}) = \sum_{j=1}^{m}\left(\sum_{i=1}^{n} A_{ji}\hat{x}_i - y_j\right)^2 = \|A\hat{x} - y\|_2^2$$

and the inferred mixture composition is the minimizer of this loss, $\hat{x}=\text{argmin } L(x)$. If the number of binders is greater than the number of barcodes, then $A_x=y$ is an overdetermined system and there is a unique minimizer of the loss. The solution is given by $$\hat{x}=A^+y$$

where $A^+=(A^TA)^{-1}A^T$ is the Moore-Penrose inverse of the fingerprint matrix. If relative abundances (proportions) are desired, the coefficients can be normalized to sum to 1.

Note that the L2 loss function above is the simplest case. It is (proportional to) the negative log likelihood in the case where $\varepsilon_1$ is absent (no noise in binding) and $\varepsilon_2$ is Gaussian noise of fixed variance. To model more realistic forms of noise, other loss functions can be chosen.

Appendix A: Biophysical Model of Binding Process

Let n be the number of barcoded protein species in a sample, and let $x_i$, i=1, . . . , n be the concentrations of each barcode species added to the decoding well. Likewise, let m be the number of decoder species in the decoder pool, and let $d_j$, j=1, . . . , m be the concentrations of each decoder species added to the decoding well. Suppose that any decoder can interact with any barcode in a one-to-one stoichiometry to form a bound complex. A total number of nm such complexes can be formed, one for each barcode-decoder pair. Let $c_{ij}$, i=1, . . . , n, j=1, . . . , m be the concentration of a complex between barcode i and decoder j, and let $K_{ij}$ be the equilibrium dissociation constant characterizing the affinity of this interaction, with $\Delta G_{binding}=-RT \ln K_{ij}$.

For any decoder species, we assume that the amount which binds to the sample and subsequently eluted is given by $$y_j \equiv \sum_{i=1}^{m} c_{ij},$$

the bound complexes of that decoder summed over all possible barcode pairs.

In the simplest case, we assume that each species is an ideal solute in a dilute solution, and that the binding between barcodes and decoders is allowed to approach thermodynamic equilibrium. At equilibrium, some fraction of the decoders will bind to the barcodes, but there will still be remaining unbound barcodes, with concentrations $\tilde{x}_i$, i=1, . . . n, as well as unbound decoders, with concentrations $\tilde{d}_j$, j=1, . . . m.

The equilibrium state is given by minimizing the overall free energy of the system. This is shown to be equivalent to solving the following set of equations:

$$x_i = \tilde{x}_i + \sum_{j=1}^{m} c_{ij} \text{ for } i = 1, \ldots n$$

$$d_j = \tilde{d}_j + \sum_{i=1}^{n} c_{ij} \text{ for } j = 1, \ldots m$$

$$K_{ij} = \tilde{x}_i \tilde{d}_j / c_{ij} \text{ for } i = 1, \ldots, n, j = 1, \ldots, m$$

The first equation ensures the conservation of mass: the total amount of a barcode species is the unbound amount plus the amounts bound in complexes with all possible decoder partners. The second equation is an analogous statement for the decoders. The last equation is the definition of an equilibrium constant of a barcode-decoder pair.

The known values are the equilibrium constants $K_{ij}$ and the $x_i$ and $d_j$, representing the total concentration of each species of barcode and decoder, respectively, added to the well. The unknown variables are $\tilde{x}$, $\tilde{d}_j$, and $\tilde{c}_{ij}$. The values of the unknown variables are determined by solving the system of equations above.

The Linear Approximation

In the decoding process, a decoder pool with fixed values of $K_{ij}$ and $d_j$ is added to a sample of unknown barcode composition, $x_i$. The observable output of the binding process is the amount of each decoder species which binds to the sample, $$y_j \equiv \sum_{i=1}^{m} c_{ij}.$$

A key question of the binding process is how the input, the barcode concentrations $x_i$, affects the output, the bound decoder amounts $y_j$.

In general, the system of equations above is non-linear, but when certain conditions are met, the binding process can be well approximated by a set of linear equations. The decoding process is greatly simplified if the underlying equations are linear. A linear system implies that, at the least:
1) If the concentration of a barcode is doubled, the decoders bound to that barcode are all correspondingly doubled. (no saturation)
2) If two barcodes are mixed together, the decoders bound to the mixture are the sum of the decoders bound to each barcode alone. (no competition)

These two criteria can be thought of as linearity of single and multiple barcode detection, respectively. They are necessary, but not sufficient conditions.

To see how these criteria play in practice, consider the following binding situations which violate one or more of the criteria. Suppose that the decoder is the limiting reagent in a one-to-one stoichiometry of barcodes and decoders. Above a certain barcode concentration, all the available decoders would become saturated; an increase in $x_i$ would not lead to a proportional increase in $y_j$. Thus, to avoid saturation, the barcode concentrations should be kept below the Kd of the interaction (or the decoder concentration, whichever is greater—see below).

As another example, consider a situation where two barcodes A and B both have affinity for a certain decoder D, but barcode A has a much stronger affinity than barcode B. In the absence of A, the binding of barcode B has a certain binding curve. However, if there is enough A to deplete much of the available D, the binding of barcode B to the remaining D will be significantly altered. This is a situation where A and B compete for available decoder D. Note, however, that if the binding of A did not deplete the amount of D remaining in the pool, then the binding between B and D would not be altered by the presence of A. The competitive behavior occurs only in situations where the available D is significantly consumed by binding to A—if A is highly abundant and/or the A-D affinity is strong. In both examples of non-linear situations, one or more decoders in the pool is significantly depleted by binding to barcodes.

These examples indicate that the binding process is linear when a small fraction of the decoding pool is bound to the sample. Indeed, if this condition is met, the equations above can be simplified into a simple linear system. Under this assumption, the amount of unbound decoder $\tilde{d}_j$ is well approximated by the total amount of decoder, $d_j$. If we further assume that the bound complexes deplete a small fraction of the available barcodes, then the system of equations simplifies to $$c_{ij} \approx x_i d_j / K_{ij}$$

and the output can be represented with a simple matrix multiplication, $$y_j = \sum_{i=1}^{n} A_{ji} x_i \text{ with } A_{ji} \equiv d_j / K_{ij}$$

Example 9: Assessment of Absolute Payload Abundance of a Single Test Barcode Using a Reference Barcode (or Spike-In Barcode)

The present example demonstrates a method to determine the absolute payload abundance of payloads in a pool using a reference barcode and barcode decoding.

Figure 10:
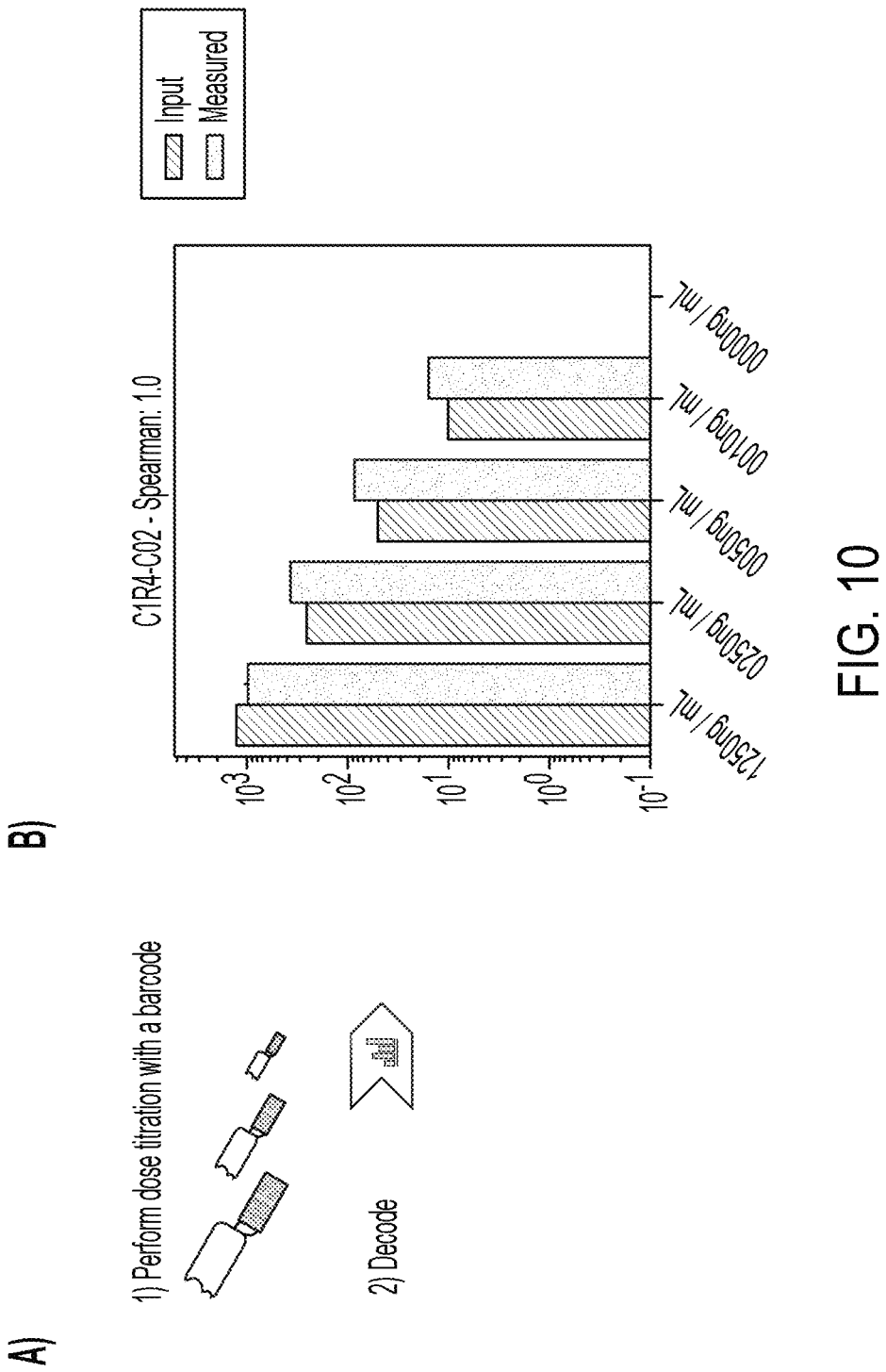
FIG. 10 shows a method and data for determining the absolute concentration of a single test barcode as described herein. (A) shows a schematic of the experiment. A single test barcode was assayed at several concentrations, while a "spike-in" barcode (i.e. a reference barcode) was added to each assay mixture at a known concentration. The various concentrations of the test barcode were contacted with binding agents and decoding was performed as described herein. The prediction of the "spike-in" barcode was used to determine the absolute amount of the test barcode being measured. (B) shows a plot of the measured absolute quantities of the test barcode (right bar) compared to known input concentrations of the test barcode (left bar) for each titration of the test barcode. The Y-axis is the logarithm of the test barcode concentration in nanograms per milliliter (ng/mL). (C) shows the results of determination of absolute concentration for 6 different barcodes. The plots show known input concentrations (left bar) and measured concentration (right bar) for six (6) different barcodes.
Figure 10C:
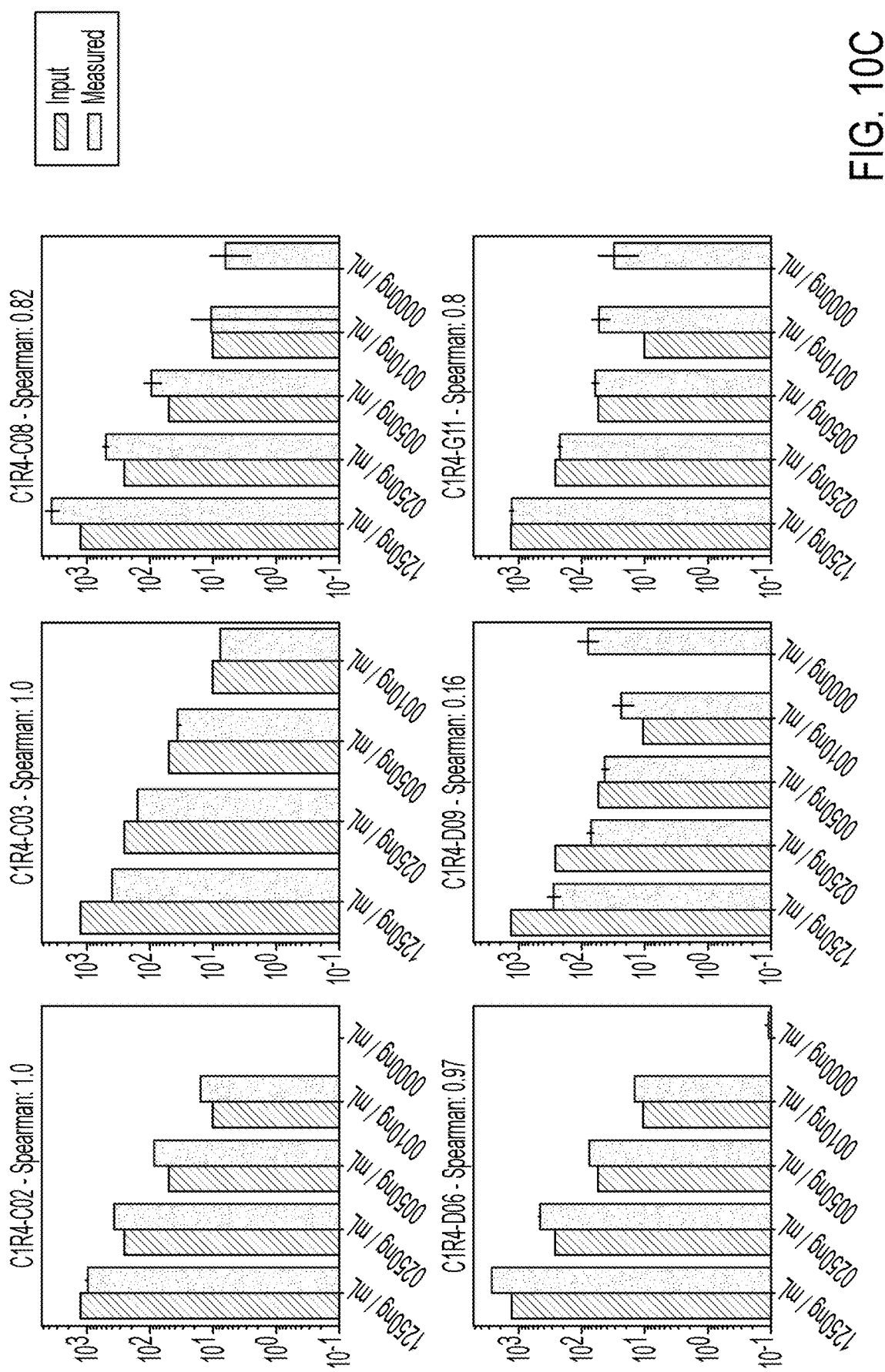

FIG. 10A shows a schematic of the experiment. A single test barcode attached to payload was assayed at several concentrations, ranging from 0 ng/mL to 1250 ng/mL. In the same sample, a "spike-in" barcode attached to a payload (i.e. a reference barcode) was added to each assay mixture at 250 ng/mL. The various concentrations of the test barcoded payload were contacted with binding agents (i.e. binding agents with binders expressed on them) and decoding was performed as described herein. The prediction of the reference or "spike-in" barcode was used to determine the absolute amount of the test barcode, and by extension the barcoded payload, being measured (see Example 8). FIG. 10B shows a plot of the measured absolute quantities of the test barcode (right bar) compared to known input concentrations of the test barcode (left bar) for each titration of the test barcode. The Y-axis is the logarithm of the test barcode concentration in nanograms per milliliter (ng/mL). FIG. 10C shows the results of determination of absolute concentration for 6 different barcoded payloads. The plots show known input concentrations (left bar) and measured concentration (right bar) for six (6) different barcoded payloads.

REFERENCES

Towbin H, Staehelin T. Gordon J. Electrophoretic transfer of proteins from polyacrylamide gels to nitrocellulose sheets: procedure and some applications. *Proc Natl Acad Sci USA*. 1979; 76(9):4350-4354. doi:10.1073/pnas.76.9.4350

Engvall E. Perlmann P. Enzyme-linked immunosorbent assay, Elisa, 3. Quantitation of specific antibodies by enzyme-labeled anti-immunoglobulin in antigen-coated tubes. J Immunol. 1972 July; 109(1):129-35. PMID: 4113792.

Elshal M F, McCoy J P. Multiplex bead array assays: performance evaluation and comparison of sensitivity to ELISA. Methods. 2006 April; 38(4):317-23. doi: 10.1016/j.ymeth.2005.11.010. PMID: 16481199; PMCID: PMC1534009.

Shendure J, Porreca G J, Reppas N B, Lin X, McCutcheon J P, Rosenbaum A M, Wang M D, Zhang K, Mitra R D, Church G M. Accurate multiplex polony sequencing of an evolved bacterial genome. Science. 2005 Sep. 9; 309 (5741):1728-32. doi: 10.1126/science.1117389. Epub 2005 Aug. 4. PMID: 16081699.

Trads J B, Tørring T, Gothelf K V. Site-Selective Conjugation of Native Proteins with DNA. Acc Chem Res. 2017 Jun. 20; 50(6):1367-1374. doi: 10.1021/acs.accounts.6b00618. Epub 2017 May 9. PMID: 28485577.

Egloff P, Zimmermann I, Arnold F M, Hutter C A J, Morger D, Opitz L, Poveda L, Keserue H A, Panse C, Roschitzki B, Seeger M A. Engineered peptide barcodes for in-depth analyses of binding protein libraries. Nat Methods. 2019 May; 16(5):421-428. doi: 10.1038/s41592-019-0389-8. Epub 2019 Apr. 22. PMID: 31011184; PMCID: PMC7116144.

Pollock S B, Hu A, Mou Y, Martinko A J, Julien O, Hornsby M, Ploder L, Adams J J, Geng H, Müschen M, Sidhu S S, Moffat J, Wells J A. Highly multiplexed and quantitative cell-surface protein profiling using genetically barcoded antibodies. Proc Natl Acad Sci USA. 2018 Mar. 13; 115(11):2836-2841. doi: 10.1073/pnas.1721899115. Epub 2018 Feb. 23. PMID: 29476010; PMCID: PMC5856557.

Mohan D, Wansley D L, Sie B M, Noon M S, Baer A N, Laserson U, Larman H B. PhIP-Seq characterization of serum antibodies using oligonucleotide-encoded peptidomes. Nat Protoc. 2018 September; 13(9):1958-1978.

doi: 10.1038/s41596-018-0025-6. Erratum in: Nat Protoc. 2018 Oct. 25; PMID: 30190553: PMCID: PMC6568263.

Barbas, C. F., Burton, D. R., Scott, J. K., & Silverman, G. J. Phage Display: A Laboratory Manual. 2001. Cold Spring Harbor Laboratory Press.

OTHER EMBODIMENTS

It is to be appreciated by those skilled in the art that various alterations, modifications, and improvements to the present disclosure will readily occur to those skilled in the art. Such alterations, modifications, and improvements are intended to be part of the present disclosure, and are intended to be within the spirit and scope of the invention. Accordingly, the foregoing description and drawing are by way of example only and any invention described in the present disclosure if further described in detail by the claims that follow.

Those skilled in the art will appreciate typical standards of deviation or error attributable to values obtained in assays or other processes as described herein. The publications, websites and other reference materials referenced herein to describe the background of the invention and to provide additional detail regarding its practice, including those listed in the above References section, are hereby incorporated by reference in their entireties.

It is to be understood that while embodiments of the invention have been described in conjunction with the detailed description thereof, the foregoing description is intended to illustrate and not limit the scope of the invention, which is defined by the scope of the appended claims. Other aspects, advantages, and modifications are within the scope of the following claims.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

Lengthy table referenced here

US12037706-20240716-T00001

Please refer to the end of the specification for access instructions.

Lengthy table referenced here

US12037706-20240716-T00002

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US12037706B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/?pageRequest=docDetail&DocID=US12037706B2). An electronic copy of the sequence listing will also be available from the USPTO upon request and payment of the fee set forth in 37 CFR 1.19(b)(3).

We claim:

1. A library comprising a plurality of nucleic acids, wherein the plurality together encodes a collection of peptide barcodes characterized in that:
   a) each peptide barcode has a length within a range of 5 to 50, 8 to 25, 9 to 25, or 9 to 15 amino acids; and
   b) each peptide barcode has been determined to bind specifically to a particular group of polypeptide binders within a set of binders, and
   wherein each nucleic acid comprises, in order from 5' to 3' or 3' to 5', one or more of:
      i) a first invariant sequence;
      ii) a variant sequence that is at least 9 nucleotides long; and
      iii) a second invariant sequence,
   wherein the collection of peptide barcodes comprises at least one peptide barcode having an amino acid sequence selected from the group consisting of SEQ ID NOs: 5347-8398, and
   wherein the plurality of nucleic acid sequences comprises at least one nucleic acid encoding sequence selected from the group consisting of SEQ ID NOs: 1148-4199.

2. The library of claim 1, further comprising one or more of:
   c) sequence contains short helical motif;
   d) sequence contains a disordered motif;
   e) an invariant sequence which links sequence to protein of interest.

3. The library of claim 1, wherein each peptide barcode of the collection binds specifically to one or more polypeptide binders within a set of binders.

4. The library of claim 1, wherein the first invariant sequence comprises or is a linker sequence or a payload sequence.

5. The library of claim 1, wherein the second invariant sequence comprises or is a linker sequence, a stop codon, or a payload sequence.

6. The library of claim 1, wherein the first invariant sequence comprises or is a first linker sequence, wherein the second invariant sequence comprises or is a second linker sequence, and wherein the first linker sequence is the same as the second linker sequence.

7. The library of claim 1, wherein the first invariant sequence comprises or is a first linker sequence, wherein the second invariant sequence comprises or is a second linker sequence, and wherein the first linker sequence is different than second linker sequence.

\* \* \* \* \*